United States Patent
Tsai et al.

(10) Patent No.: US 11,827,629 B2
(45) Date of Patent: Nov. 28, 2023

(54) CDGSH IRON SULFUR DOMAIN 2 ACTIVATORS AND USE THEREOF

(71) Applicants: National Health Research Institutes, Miaoli County (TW); National Yang Ming Chiao Tung University, Taipei (TW)

(72) Inventors: Ting-Fen Tsai, Taipei (TW); Jinq-Chyi Lee, Miaoli County (TW); Teng-Kuang Yeh, Bellevue, WA (US)

(73) Assignees: National Health Research Institutes, Miaoli County (TW); National Yang Ming Chiao Tung University, Taipei (TW)

( * ) Notice: Subject to any disclaimer, the term of this patent is extended or adjusted under 35 U.S.C. 154(b) by 0 days.

(21) Appl. No.: 17/824,547

(22) Filed: May 25, 2022

(65) Prior Publication Data

US 2022/0411418 A1 Dec. 29, 2022

Related U.S. Application Data

(60) Provisional application No. 63/193,975, filed on May 27, 2021.

(51) Int. Cl.
| | |
|---|---|
| C07D 209/44 | (2006.01) |
| C07D 417/12 | (2006.01) |
| A61P 1/16 | (2006.01) |
| C07D 401/12 | (2006.01) |
| C07D 403/12 | (2006.01) |
| C07D 409/12 | (2006.01) |
| C07D 413/12 | (2006.01) |
| C07D 413/14 | (2006.01) |
| C07D 495/04 | (2006.01) |

(52) U.S. Cl.
CPC ............. *C07D 417/12* (2013.01); *A61P 1/16* (2018.01); *C07D 209/44* (2013.01); *C07D 401/12* (2013.01); *C07D 403/12* (2013.01); *C07D 409/12* (2013.01); *C07D 413/12* (2013.01); *C07D 413/14* (2013.01); *C07D 495/04* (2013.01)

(58) Field of Classification Search
CPC .......................... C07D 209/44; A61K 31/4035
See application file for complete search history.

(56) References Cited

U.S. PATENT DOCUMENTS

| | | |
|---|---|---|
| 2007/0213321 A1 | 9/2007 | Chong et al. |
| 2012/0065200 A1 | 3/2012 | Barbosa et al. |
| 2020/0054696 A1 | 2/2020 | Chen et al. |
| 2020/0369682 A1 | 11/2020 | Meldrum et al. |

FOREIGN PATENT DOCUMENTS

| | | |
|---|---|---|
| CA | 2984407 A1 | 5/2018 |
| TW | 2022/00126 A | 1/2022 |

OTHER PUBLICATIONS

Registry RN 2759727-12-1 (Feb. 18, 2022).*
RN 2430947-43-4 Registry, RN 2329498-49-7 Registry, RN 2193732-62-4 Registry, RN 2193732-58-8 Registry, RN 1520558-85-3 Registry, RN 1446277-14-0 Registry, RN 1355843-11-6 Registry, RN 2326325-59-9 Registry, RN 1311789-50-0 Registry, (2020).
Pubchem CID 56791814, Mar. 8, 2012.
Pubchem CID 79214408, Oct. 19, 2014.
Chen et al "A Role for the CISD2 Gene in Lifespan Control and Human Disease" Annals of the New York Academy of Sciences vol. 1201, pp. 58-64, 2010.
Chen et al "CISD2 Deficiency Drives Premature Aging and Causes Mitochondria-Mediated Defects in Mice" Genes and Development vol. 23, pp. 1183-1194, 2009.
Huang et al "CISD2 Slows Down Liver Aging and Attenuates Age-Related Metabolic Dysfunction in Male Mice" Aging Cell vol. 20, pp. 1-13, 2021.
Huang et al "Comparative Proteomic Profiling Reveals a Role for CISD2 in Skeletal Muscle Aging" Aging Cell vol. 17, pp. 1-13, 2018.
Shen et al "CISD2 Haploinsufficiency Disrupts Calcium Homeostasis, Causes Nonalcoholic Fatty Liver Disease, and Promotes Hepatocellular Carcinoma" Cell Reports vol. 21, pp. 2198-2211, 2017.
Shen et al "CISD2 Maintains Cellular Homeostasis" BBA Molecular Cell Research vol. 1868, Article 118954, 2021.
Sun et al "CISD2 Plays an Essential Role in Corneal Epithelial Regeneration" EBioMedicine vol. 73, Article 103654, 2021.
Wang et al "CISD2 Modulates the Differentiation and Functioning of Adipocytes by Regulating Intracellular $Ca^{2+}$ Homeostasis" Human Molecular Genetics vol. 23, pp. 4770-4785, 2014.
Wu et al "A Persistent Level of CISD2 Extends Healthy Lifespan and Delays Aging in Mice" Human Molecular Genetics vol. 21, pp. 3956-3968, 2012.
Yeh et al "CISD2 is Essential to Delaying Cardiac Aging and to Maintaining Heart Functions" PLoS Biology vol. 17, pp. 1-24, 2019.
Yeh et al "Hesperetin Promotes Longevity and Delays Aging via Activation of CISD2 in Naturally Aged Mice" Journal of Biomedical Science vol. 29, pp. 1-21, 2022.
Yeh et al "Rejuvenation: Turning Back Time by Enhancing CISD2" International Journal of Molecular Sciences vol. 23, pp. 1-27, 2022.

* cited by examiner

*Primary Examiner* — Deepak R Rao
(74) *Attorney, Agent, or Firm* — Morse, Barnes-Brown & Pendleton, P.C.; Martin Z. Zhang, Esq.

(57) ABSTRACT

Isoindoline compounds and their pharmaceutical compositions. Also provided are methods of treating a Cisd2-insufficiency associated disorder and protecting against doxorubicin-induced cardiotoxicity.

22 Claims, No Drawings

CDGSH IRON SULFUR DOMAIN 2 ACTIVATORS AND USE THEREOF

CROSS-REFERENCE TO RELATED APPLICATIONS

This application claims the benefit of priority based on U.S. Provisional Application No. 63/193,975, filed May 27, 2021, the content and disclosure of which is incorporated herein by reference in its entirety.

BACKGROUND

CDGSH iron sulfur domain 2 (Cisd2) is an iron-sulfur transmembrane protein encoded by the Cisd2 gene. This protein localizes on the mitochondrial outer membrane, the endoplasmic reticulum (ER) membrane, and other mitochondria or ER associated membranes.

Cisd2 regulates intracellular $Ca^{2+}$ homeostasis, mitochondrial integrity, and energy metabolism.

Studies show that Cisd2 is an important regulator of aging and metabolism. It is essential for delaying cardiac aging and maintaining heart electromechanical functions. See Wu et al., *Human Molecular Genetics* 21, 3956-68 (2012).

Cisd2 insufficiency has been linked to several disorders, e.g., liver diseases, metabolic diseases, heart diseases, and aging-associated diseases.

Thus, there is a need to develop Cisd2 activators capable of increasing Cisd2 expression to treat disorders associated with Cisd2 insufficiency.

SUMMARY

It was discovered unexpectedly that certain isoindoline compounds are effective in treating a subject suffering from a disorder associated with Cisd2 insufficiency by increasing the Cisd2 level.

Accordingly, one aspect of this invention relates to isoindoline compounds of formula (I):

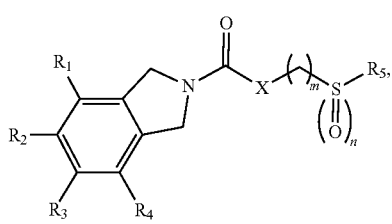

in which
  each of $R_1$, $R_2$, $R_3$, and $R_4$, independently, is H, halo, hydroxyl, $NO_2$, $NH_2$, $C_1$-$C_6$ alkoxy, $CO_2R_a$, $C_{1-10}$ heterocycloalkyl, or $OC(O)R_a$, $R_a$ being $C_1$-$C_6$ alkyl optionally substituted with one or more groups selected from halo, cycloalkyl, cycloheteroalkyl, aryl, and heteroaryl;
  $R_5$ is aryl, arylalkyl, heteroaryl, or heteroaryl alkyl, each of which is optionally substituted with one or more groups selected from halo, $C_1$-$C_6$ alkyl, $NH_2$, CN, and oxo;
  X is NH, $CH_2$, or $CF_2$;
  m is 0, 1, or 2; and
  n is 0, 1, or 2.

Preferably, each of $R_1$, $R_2$, and $R_3$, independently, is H, F, Cl, OH, $NO_2$, $NH_2$, $CH_3O$, morpholino, or $CO_2CH_3$; $R_4$ is H; and $R_5$ is

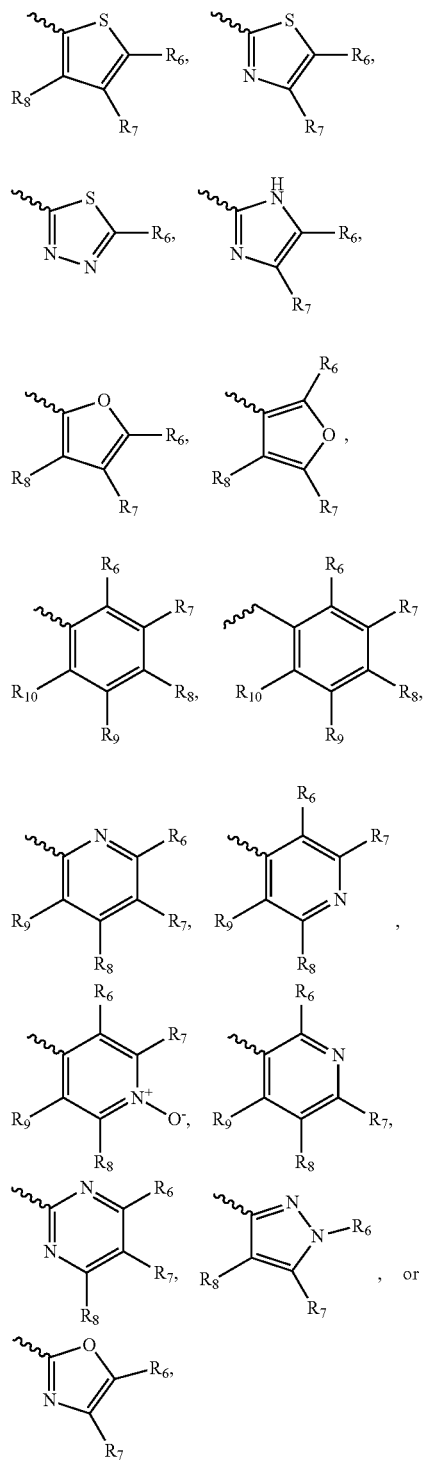

in which, each of $R_6$, $R_7$, $R_8$, $R_9$, and $R_{10}$, independently, is H, F, Cl, OH, CN, $NO_2$, $NH_2$, $NHC(O)R_{11}$, $C_1$-$C_6$ alkyl, difluoromethyl, $OR_{11}$, $CO_2CH_3$, $CO_2CH_2CH_3$, $CONHR_{11}$, $C(O)CH_3$, $C(O)CH_2CH_3$, or $CH_2OH$, $R_{11}$ being $C_1$-$C_6$ alkyl or aryl.

Examples of the R₅ group include
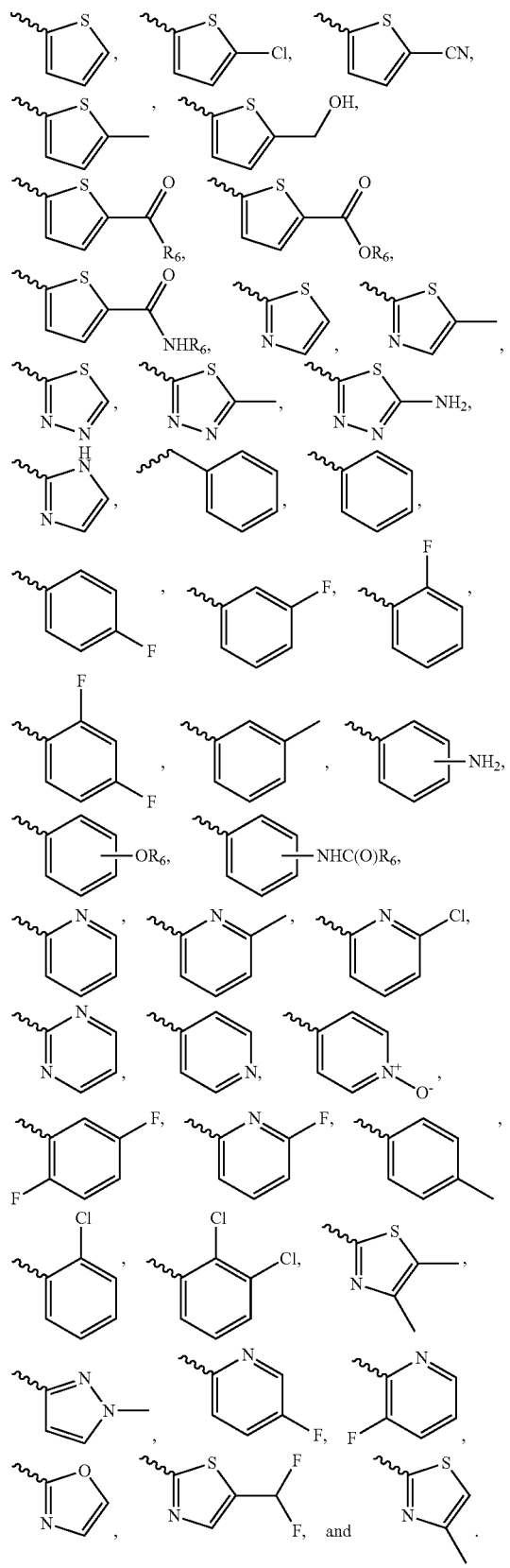
Preferably, R₅ is
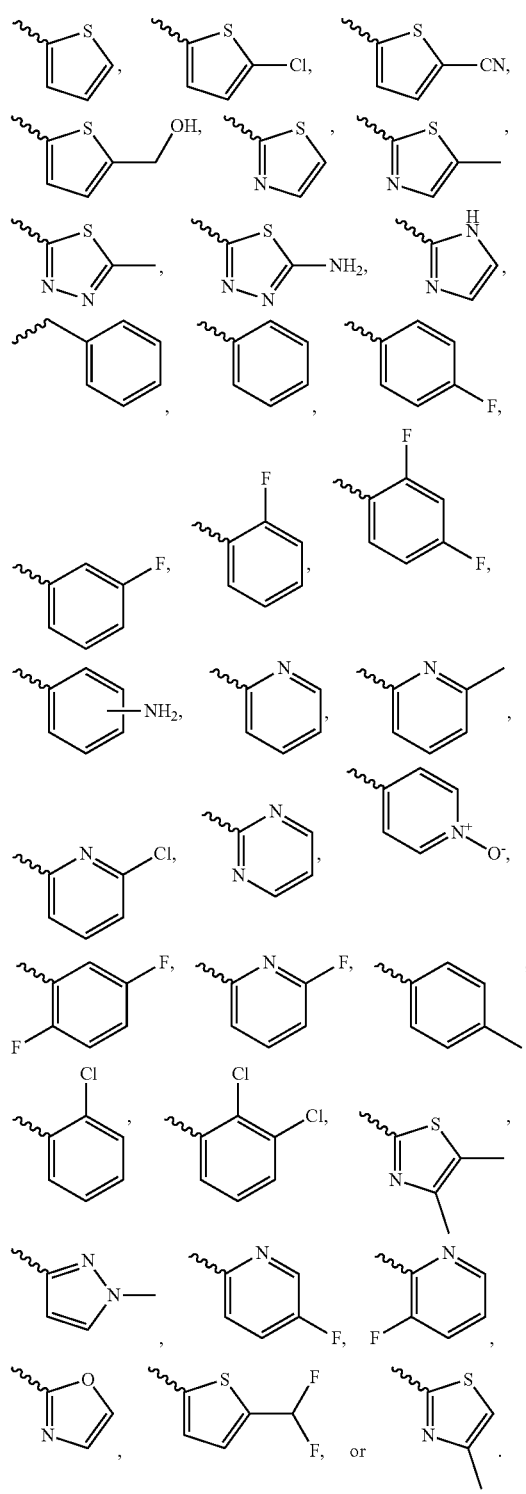
Turning to variables X, m, and n in formula (I), preferably they are selected from the following combinations: X is CH₂, m is 0, and n is 0 or 1; X is CH₂, m is 1, and n is 0 or 1; X is NH, m is 2, and n is 0; X is CF₂, m is 0 or 1, and n is 0; X is CH₂, m is 0, and n is 2; X is CH₂, m is 1, and n is 2; and X is CF₂, m is 0, and n is 1 or 2.

More preferably, compounds of formula (I) have one or more of the following features: each of $R_1$, $R_2$, and $R_3$, independently, is H or F; $R_4$ is H; X is $CH_2$; m is 0 or 1; n is 1 or 2; and $R_5$ is
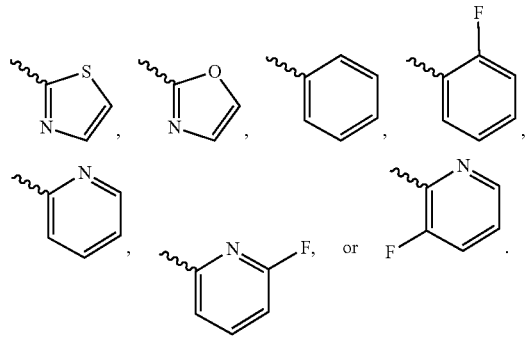
Provided in Table 1 below are 109 exemplary compounds of formula (I), i.e., Compounds 1-109.

TABLE 1-continued
| No. | Chemical Structure |
|---|---|
| 14 | 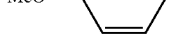 |
| 15 | 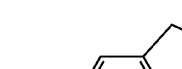 |
| 16 | 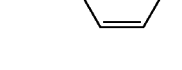 |
| 17 | 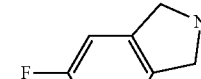 |
| 18 | 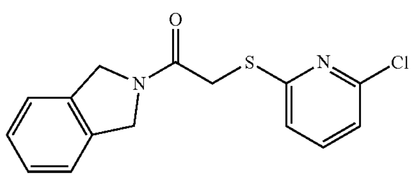 [SMILES: O=C(CSc1cccc(Cl)n1)N1Cc2ccccc2C1] |
| 19 | 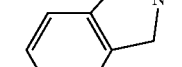 |
| 20 | 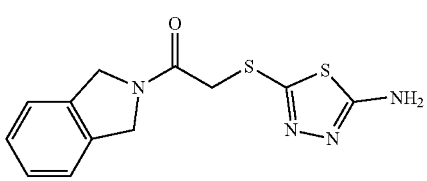 [SMILES: Nc1nnc(SCC(=O)N2Cc3ccccc3C2)s1] |
| 21 | 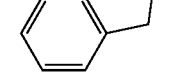 |
| 22 | 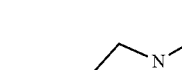 |
| 23 | 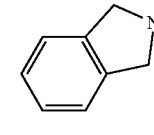 |
| 24 | 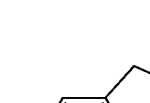 |
| 25 | 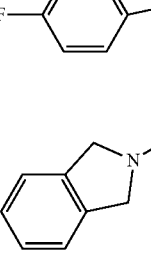 |
| 26 | 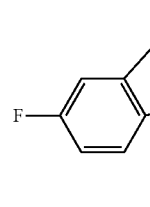 |
| 27 | 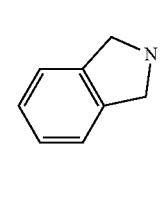 |
| 28 | 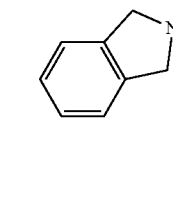 |
| 29 | 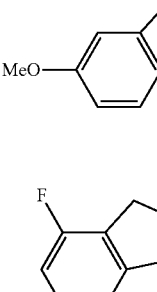 |
| 30 | |

TABLE 1-continued
| No. | Chemical Structure |
|-----|--------------------|
| 31 | 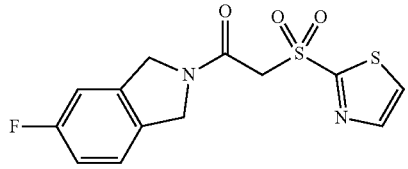 |
| 32 | 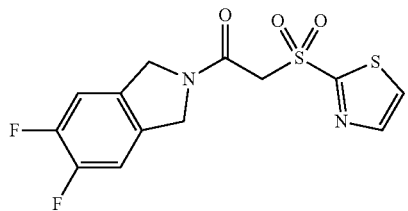 [SMILES: O=C(CS(=O)(=O)c1nccs1)N1Cc2cc(F)c(F)cc2C1] |
| 33 | 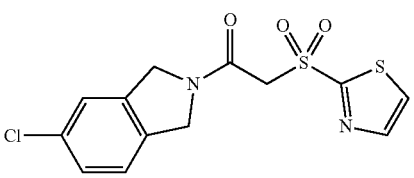 [SMILES: O=C(CS(=O)(=O)c1nccs1)N1Cc2ccc(Cl)cc2C1] |
| 34 | 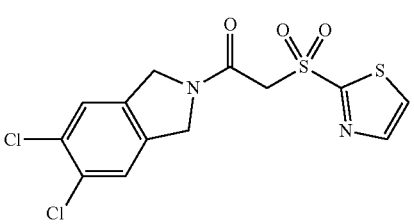 [SMILES: O=C(CS(=O)(=O)c1nccs1)N1Cc2cc(Cl)c(Cl)cc2C1] |
| 35 | 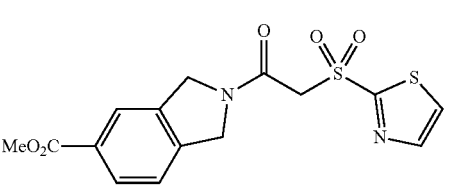 [SMILES: COC(=O)c1ccc2c(c1)CN(C(=O)CS(=O)(=O)c1nccs1)C2] |
| 36 | 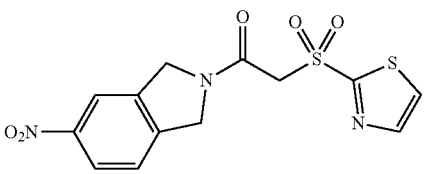 [SMILES: O=C(CS(=O)(=O)c1nccs1)N1Cc2ccc([N+](=O)[O-])cc2C1] |
| 37 | 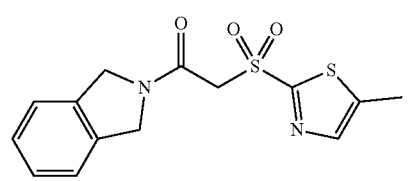 [SMILES: Cc1cnc(S(=O)(=O)CC(=O)N2Cc3ccccc3C2)s1] |
| 38 | 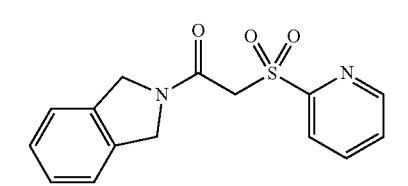 [SMILES: O=C(CS(=O)(=O)c1ccccn1)N1Cc2ccccc2C1] |
| 39 | 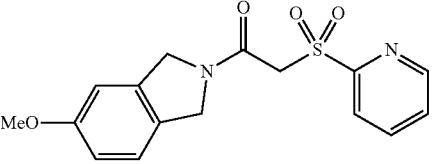 [SMILES: COc1ccc2c(c1)CN(C(=O)CS(=O)(=O)c1ccccn1)C2] |
| 40 | 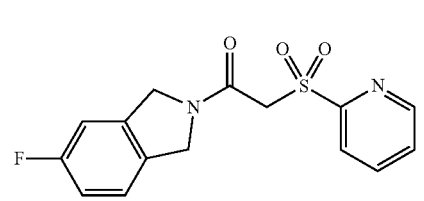 |
| 41 | 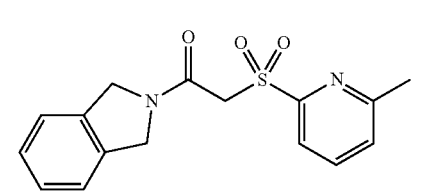 [SMILES: Cc1cccc(S(=O)(=O)CC(=O)N2Cc3ccccc3C2)n1] |
| 42 | 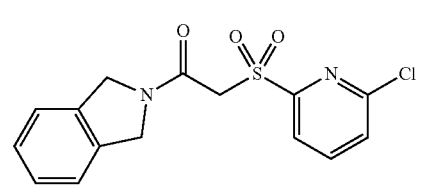 [SMILES: O=C(CS(=O)(=O)c1cccc(Cl)n1)N1Cc2ccccc2C1] |
| 43 | 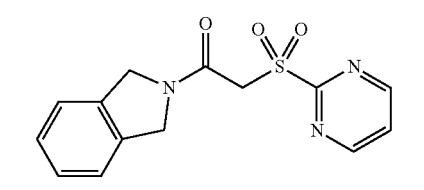 [SMILES: O=C(CS(=O)(=O)c1ncccn1)N1Cc2ccccc2C1] |
| 44 | 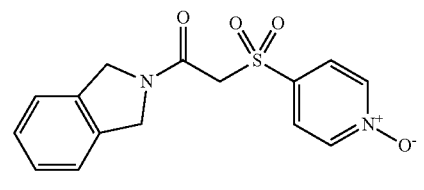 [SMILES: O=C(CS(=O)(=O)c1cc[n+]([O-])cc1)N1Cc2ccccc2C1] |
| 45 | 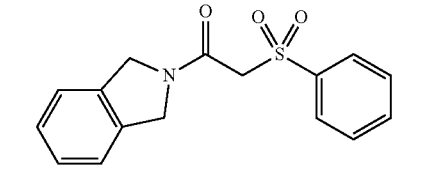 [SMILES: O=C(CS(=O)(=O)c1ccccc1)N1Cc2ccccc2C1] |
| 46 | 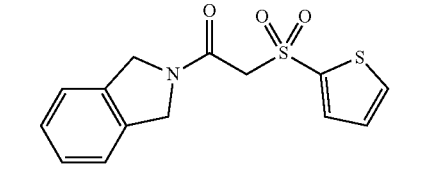 [SMILES: O=C(CS(=O)(=O)c1cccs1)N1Cc2ccccc2C1] |

TABLE 1-continued

| No. | Chemical Structure |
|---|---|
| 47 | |
| 48 | |
| 49 | |
| 50 | |
| 51 | |
| 52 | |
| 53 | |
| 54 | |
| 55 | 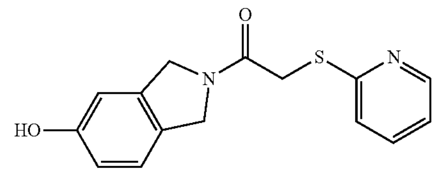 [SMILES: O=C(CSc1ccccn1)N1Cc2ccc(O)cc2C1] |
| 56 | 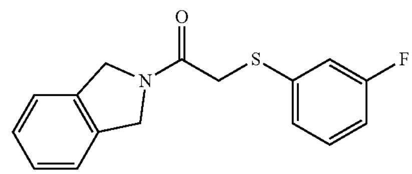 [SMILES: O=C(CSc1cccc(F)c1)N1Cc2ccccc2C1] |
| 57 | 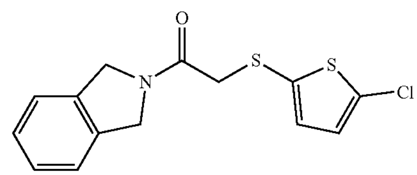 [SMILES: O=C(CSc1ccc(Cl)s1)N1Cc2ccccc2C1] |
| 58 | 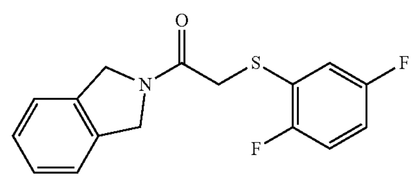 [SMILES: O=C(CSc1cc(F)ccc1F)N1Cc2ccccc2C1] |
| 59 | 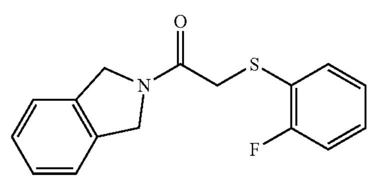 [SMILES: O=C(CSc1ccccc1F)N1Cc2ccccc2C1] |
| 60 | 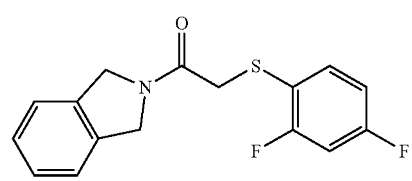 [SMILES: O=C(CSc1ccc(F)cc1F)N1Cc2ccccc2C1] |
| 61 | 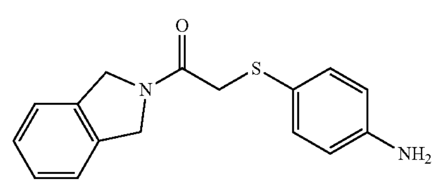 |
| 62 | 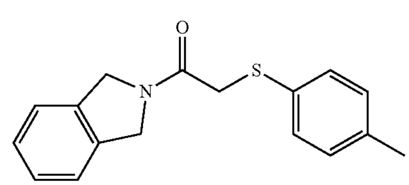 [SMILES: Cc1ccc(SCC(=O)N2Cc3ccccc3C2)cc1] |
| 63 | 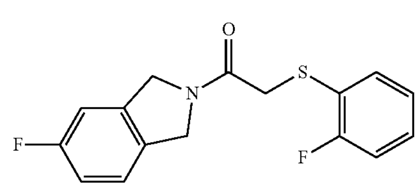 [SMILES: O=C(CSc1ccccc1F)N1Cc2ccc(F)cc2C1] |

TABLE 1-continued

| No. | Chemical Structure |
|---|---|
| 64 | 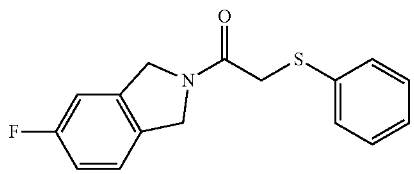 |
| 65 | 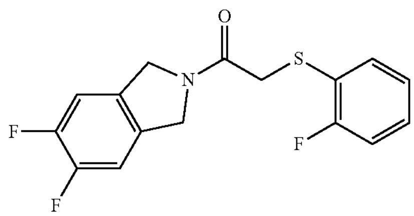 [SMILES: O=C(CSc1ccccc1F)N1Cc2cc(F)c(F)cc2C1] |
| 66 | 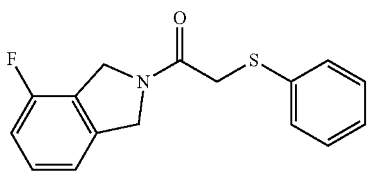 [SMILES: O=C(CSc1ccccc1)N1Cc2cccc(F)c2C1] |
| 67 | 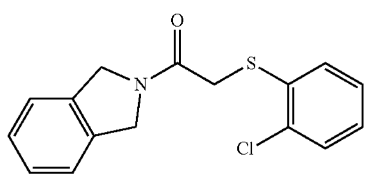 [SMILES: O=C(CSc1ccccc1Cl)N1Cc2ccccc2C1] |
| 68 | 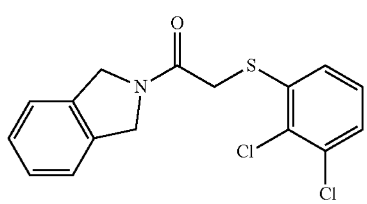 [SMILES: O=C(CSc1cccc(Cl)c1Cl)N1Cc2ccccc2C1] |
| 69 | 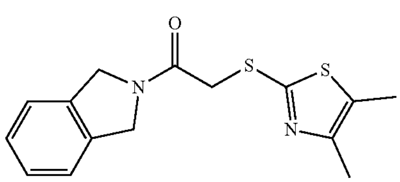 [SMILES: Cc1nc(SCC(=O)N2Cc3ccccc3C2)sc1C] |
| 70 | 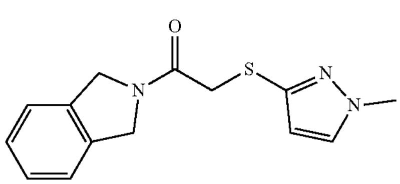 [SMILES: Cn1ccc(SCC(=O)N2Cc3ccccc3C2)n1] |
| 71 | 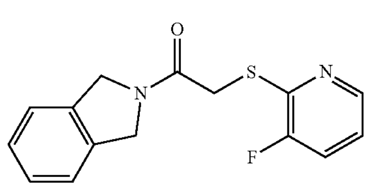 [SMILES: O=C(CSc1ncccc1F)N1Cc2ccccc2C1] |
| 72 | |
| 73 | |
| 74 | |
| 75 | |
| 76 | |
| 77 | |
| 78 | |
| 79 | |

TABLE 1-continued
| No. | Chemical Structure |
|---|---|
| 80 | 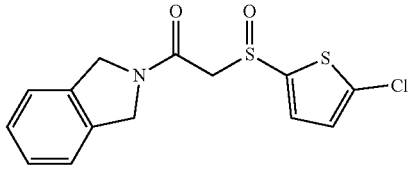 [SMILES: O=C(CS(=O)c1ccc(Cl)s1)N1Cc2ccccc2C1] |
| 81 | 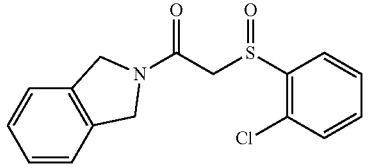 |
| 82 | 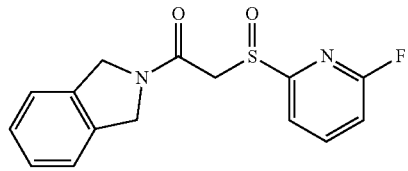 [SMILES: O=C(CS(=O)c1cccc(F)n1)N1Cc2ccccc2C1] |
| 83 | 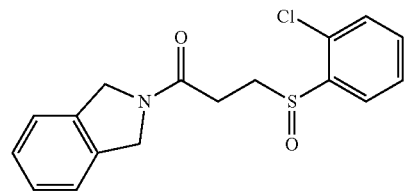 [SMILES: O=C(CCS(=O)c1ccccc1Cl)N1Cc2ccccc2C1] |
| 84 | 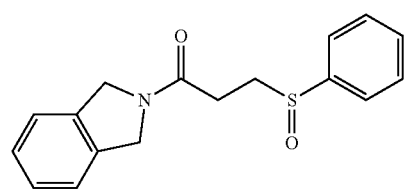 [SMILES: O=C(CCS(=O)c1ccccc1)N1Cc2ccccc2C1] |
| 85 | 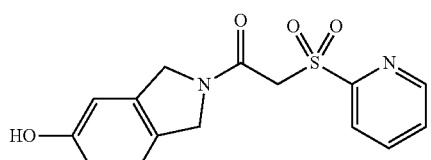 |
| 86 | 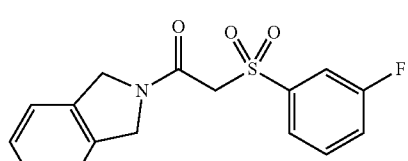 |
| 87 | 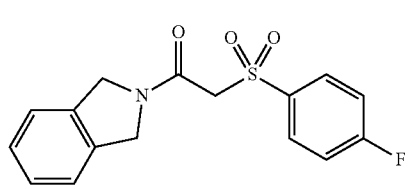 [SMILES: O=C(CS(=O)(=O)c1ccc(F)cc1)N1Cc2ccccc2C1] |
| 88 | 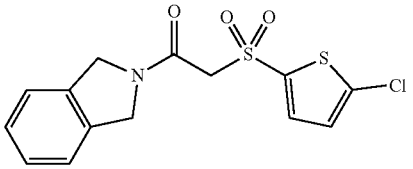 [SMILES: O=C(CS(=O)(=O)c1ccc(Cl)s1)N1Cc2ccccc2C1] |
| 89 | 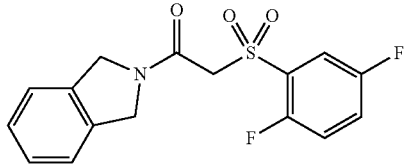 [SMILES: O=C(CS(=O)(=O)c1cc(F)ccc1F)N1Cc2ccccc2C1] |
| 90 | 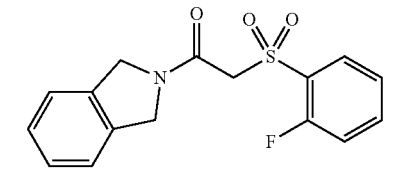 [SMILES: O=C(CS(=O)(=O)c1ccccc1F)N1Cc2ccccc2C1] |
| 91 | 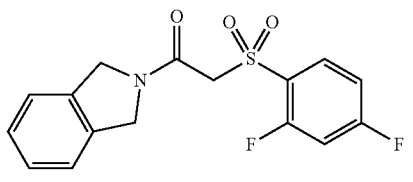 [SMILES: O=C(CS(=O)(=O)c1ccc(F)cc1F)N1Cc2ccccc2C1] |
| 92 | 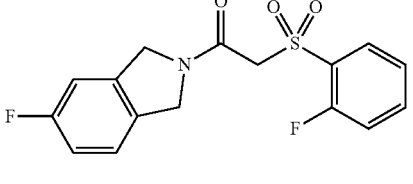 |
| 93 | 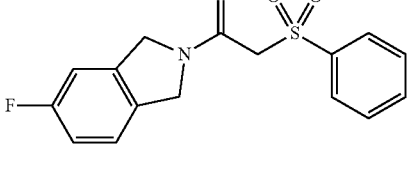 |
| 94 | 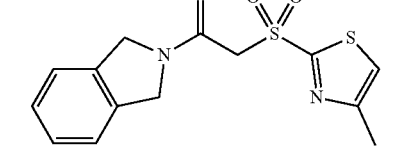 |
| 95 | 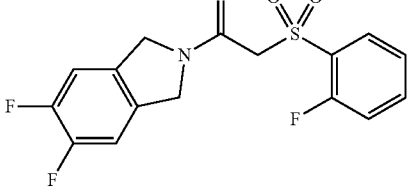 |

TABLE 1-continued

| No. | Chemical Structure |
|---|---|
| 96 | 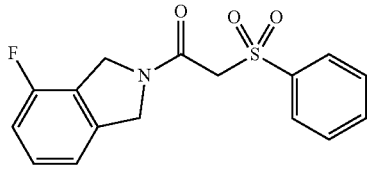 [SMILES: O=C(CS(=O)(=O)c1ccccc1)N1Cc2cccc(F)c2C1] |
| 97 | 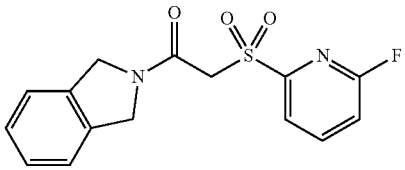 [SMILES: O=C(CS(=O)(=O)c1cccc(F)n1)N1Cc2ccccc2C1] |
| 98 | 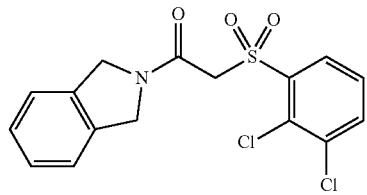 [SMILES: O=C(CS(=O)(=O)c1cccc(Cl)c1Cl)N1Cc2ccccc2C1] |
| 99 | 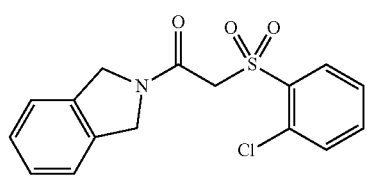 [SMILES: O=C(CS(=O)(=O)c1ccccc1Cl)N1Cc2ccccc2C1] |
| 100 | 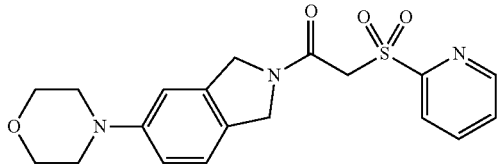 [SMILES: O=C(CS(=O)(=O)c1ccccn1)N1Cc2ccc(N3CCOCC3)cc2C1] |
| 101 | 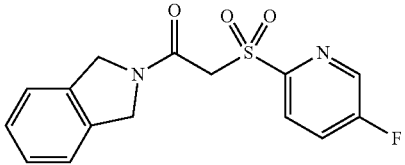 [SMILES: O=C(CS(=O)(=O)c1ccc(F)cn1)N1Cc2ccccc2C1] |
| 102 | 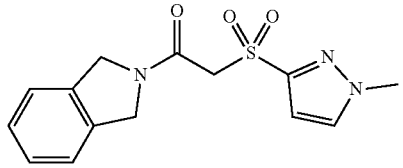 [SMILES: Cn1ccc(S(=O)(=O)CC(=O)N2Cc3ccccc3C2)n1] |
| 103 | 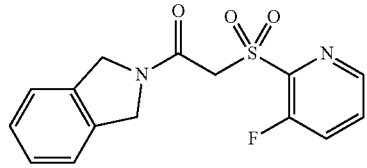 [SMILES: O=C(CS(=O)(=O)c1ncccc1F)N1Cc2ccccc2C1] |

TABLE 1-continued

| No. | Chemical Structure |
|---|---|
| 104 | 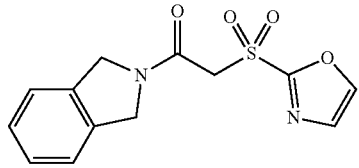 [SMILES: O=C(CS(=O)(=O)c1ncco1)N1Cc2ccccc2C1] |
| 105 | 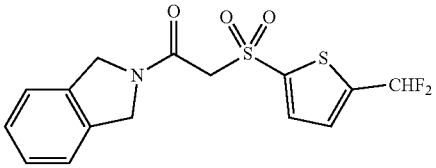 [SMILES: O=C(CS(=O)(=O)c1ccc(C(F)F)s1)N1Cc2ccccc2C1] |
| 106 | 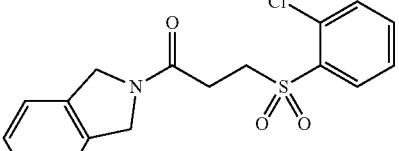 |
| 107 | 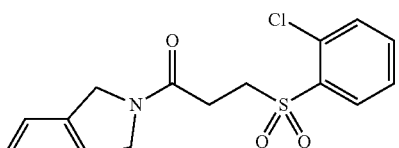 |
| 108 | 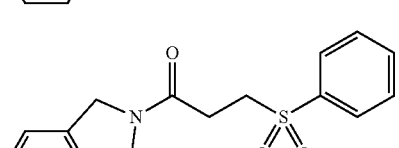 |
| 109 | 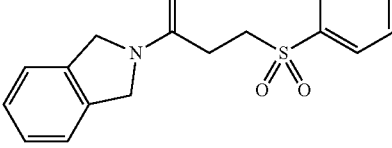 |

Preferred compounds are Compounds 28, 31, 38, 45, 48, 82, 90, 93, 103, and 104.

Another aspect of this invention relates to a pharmaceutical composition containing any of the compounds described above and a pharmaceutically acceptable carrier.

Also within the scope of this invention is a method of treating a Cisd2-insufficiency associated disorder, the method is conducted by first identifying a subject suffering from a Cisd2-insufficiency associated disorder, and then administering to the subject an effective amount of any of the compounds described above. The Cisd2-insufficiency associated disorder can be a liver disease, a metabolic disease, a heart disease, cachexia, or an aging-associated disease.

Still within the scope of this invention is a method of protecting a subject against doxorubicin-induced cardiotoxicity by administering to the subject an effective amount of a compound of this invention.

The term "alkyl" herein refers to a straight or branched hydrocarbon group, containing 1-20 (e.g., 1-10 and 1-6) carbon atoms. Examples include methyl, ethyl, n-propyl, i-propyl, n-butyl, i-butyl, and t-butyl. Alkyl includes its halo substituted derivatives, i.e., haloalkyl, which refers to alkyl substituted with one or more halogen (chloro, fluoro, bromo, or iodo) atoms. Examples include trifluoromethyl, bromomethyl, and 4,4,4-trifluorobutyl. The term "alkoxy" refers to an —O-alkyl group. Examples include methoxy, ethoxy, propoxy, and isopropoxy. Alkoxy includes haloalkoxy, referring to alkoxy substituted with one or more halogen atoms. Examples include —O—$CH_2Cl$ and —O—$CHClCH_2Cl$.

The term "cycloalkyl" refers to a saturated and partially unsaturated monocyclic, bicyclic, tricyclic, or tetracyclic hydrocarbon group having 3 to 12 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl.

The term "heterocycloalkyl" refers to a nonaromatic 5-8 membered monocyclic, 8-12 membered bicyclic, or 11-14 membered tricyclic ring system having one or more heteroatoms (e.g., O, N, P, and S). Examples of heterocycloalkyl groups include, but are not limited to, piperazinyl, imidazolidinyl, azepanyl, pyrrolidinyl, dihydrothiadiazolyl, dioxanyl, morpholinyl, tetrahydropuranyl, and tetrahydrofuranyl.

The term "aryl" refers to a 6-carbon monocyclic, 10-carbon bicyclic, 14-carbon tricyclic aromatic ring system wherein each ring may have 1 to 5 substituents. Examples of aryl groups include phenyl, naphthyl, and anthracenyl. The term "arylene" refers to bivalent aryl. The term "aralkyl" refers to alkyl substituted with an aryl group.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl. The term "heteroaryl alkyl" refers to an alkyl group substituted with a heteroaryl group.

The term "halo" refers to a fluoro, chloro, bromo, or iodo radical. The term "amino" refers to a radical derived from amine, which is unsubstituted or mono-/di-substituted with alkyl, aryl, cycloalkyl, heterocycloalkyl, or heteroaryl. The term "alkylamino" refers to alkyl-NH—. The term "dialkylamino" refers to alkyl-N(alkyl)-.

Alkyl, cycloalkyl, heterocycloalkyl, aryl, heteroaryl, aralkyl, heteroaralkyl, alkoxy, and aryloxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, and heterocycloalkyl, in which alkyl, alkenyl, alkynyl, alkyloxy, aryl, heteroaryl cycloalkyl, and heterocycloalkyl may further substituted.

The term "compound", when referring to a compound of Formula (I), also covers its salts, solvates, and prodrugs. A salt can be formed between an anion and a positively charged group (e.g., amino) on a compound; examples of a suitable anion include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. A salt can also be formed between a cation and a negatively charged group; examples of a suitable cation include sodium ion, potassium ion, magnesium ion, calcium ion, and an ammonium cation such as tetramethylammonium ion. Further, a salt can contain quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine. A prodrug refers to a compound that, after administration, is metabolized into a pharmaceutically active drug. Examples of a prodrug include esters and other pharmaceutically acceptable derivatives, which, upon administering to a subject, are capable of providing active compounds of this invention.

The details of several embodiments of the present invention are set forth in both the description and the drawings below. All features, objects, and advantages of the invention will be apparent from the description and the claims.

DETAILED DESCRIPTION

Described in detail below are isoindoline compounds of formula (I) reproduced below, as well as their syntheses and their use in treating a Cisd2-insufficiency associated disorder or protecting a subject against doxorubicin-induced cardiotoxicity.

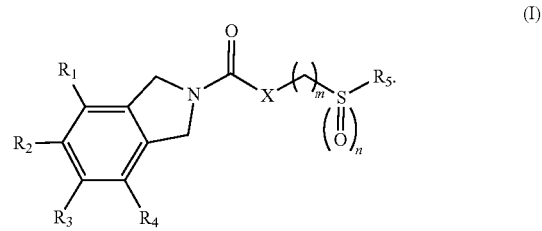

(I)

The compounds of formula (I) can be prepared by synthetic methods well known in the art. See, e.g., R. Larock, Comprehensive Organic Transformations (3$^{rd}$ Ed., John Wiley and Sons 2018); P. G. M. Wuts and T. W. Greene, Greene's Protective Groups in Organic Synthesis (4$^{th}$ Ed., John Wiley and Sons 2007); L. Fieser and M. Fieser, Fieser and Fieser's Reagents for Organic Synthesis (John Wiley and Sons 1994); and L. Paquette, ed., Encyclopedia of Reagents for Organic Synthesis (2$^{nd}$ ed., John Wiley and Sons 2009) and subsequent editions thereof.

Illustrated in Scheme 1, 2, and 3, infra, are examples how the compounds of formula (I) are prepared using various reagents.

Scheme 1 below shows synthetic routes for a sulfide compound (V) and a sulfone compound (VI) of this invention. In this scheme, R represents one or more of $R_1$, $R_2$, $R_3$, and $R_4$ groups described above. R' represents $R_5$, also described above.

Scheme 1

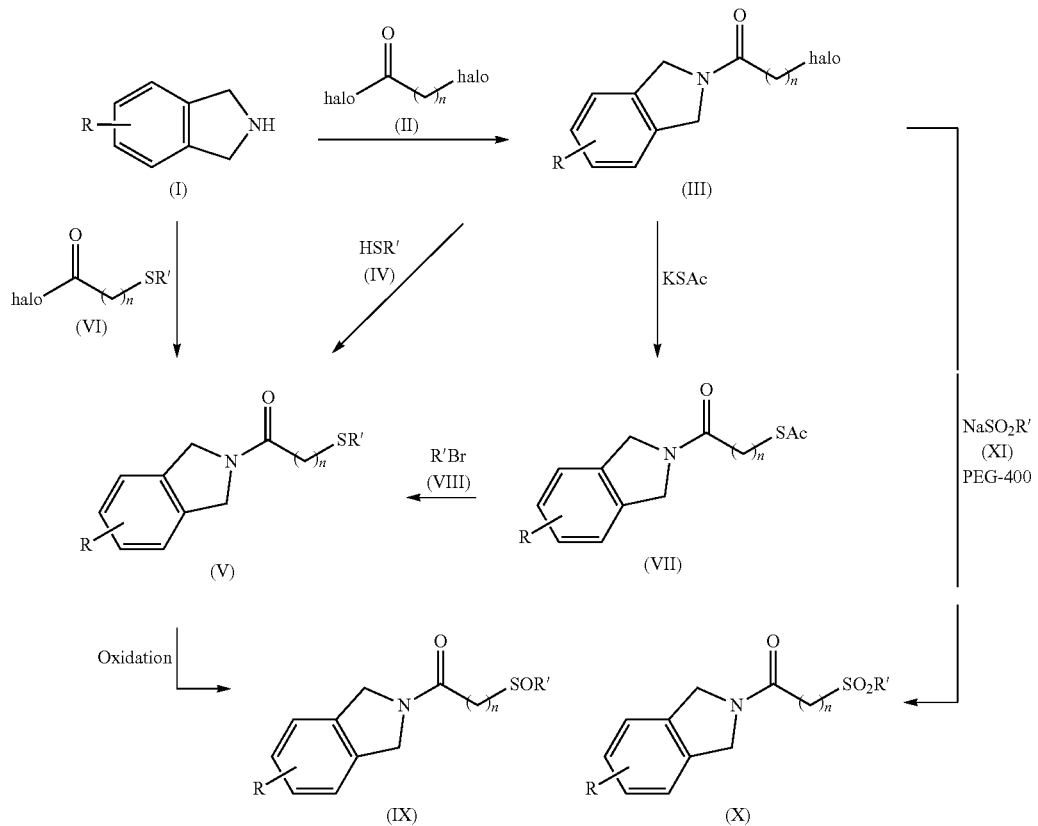

More specifically, the reaction of a commercially available or laboratory prepared isoindoline (I) with a haloacetyl halide (II) in the presence of a base (e.g., triethylamine) gives an intermediate (III), which is subsequently reacted with an appropriate thiol (IV) to afford a sulfide compound (V) of this invention.

Alternatively, a sulfide compound (V) is prepared via direct coupling of an isoindoline (I) with a heteroarylsulfanyl-containing carboxylic acid (VI), or via a palladium-catalyzed cross-coupling of a thioacetate intermediate (VII) with a heteroaryl halide (VIII).

Oxidation of a sulfide compound (V) provides a sulfoxide compound (IX) or a sulfone compound (X) of this invention. A sulfone compound (X) can also be synthesized from intermediate (III) and a sodium arylsulfinate (XI) in polyethylene glycol 400 (PEG-400).

Scheme 2 below illustrates methods of preparing a sulfide compound (XIV), a sulfoxide compound (XVI), and a sulfone compound (XVII), all of this invention.

Scheme 2

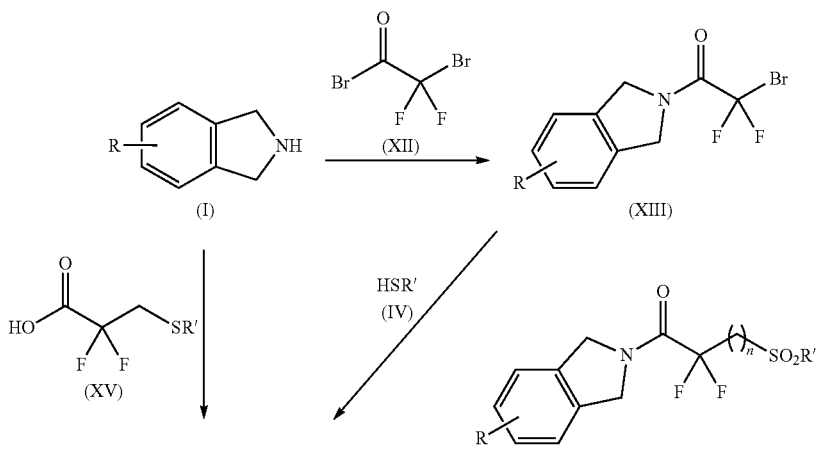

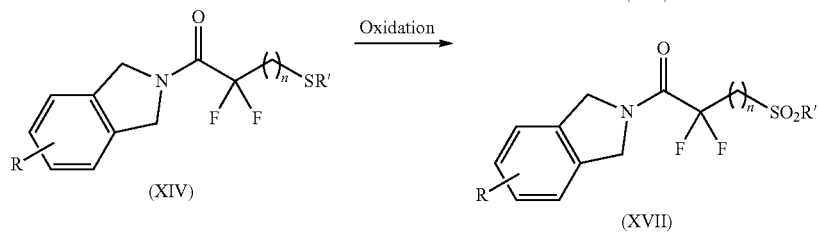

In one method, a sulfide compound (XIV) is prepared by reacting an isoindoline (I) with 2-bromo-2,2-difluoroacetyl bromide (XII), followed by a substitution reaction with a thiol (IV). In another method, a sulfide compound (XIV) is prepared in one step by coupling an isoindoline (I) with a heteroarylsulfanyl-containing carboxylic acid (XV). Oxidation of a sulfide compound (XIV) gives a sulfoxide compound (XVI) or a sulfone compound (XVII), depending on what oxidation reagent is used and its amount.

As shown in Scheme 3 below, a sulfide compound (XX) of this invention can be prepared in two steps: (i) reacting an isoindoline (I) with an isocyanate (XVIII) to obtain a urea intermediate (XIX), and (ii) coupling a thiol (IV) with the urea intermediate (XIX) to produce a sulfide compound (XX).

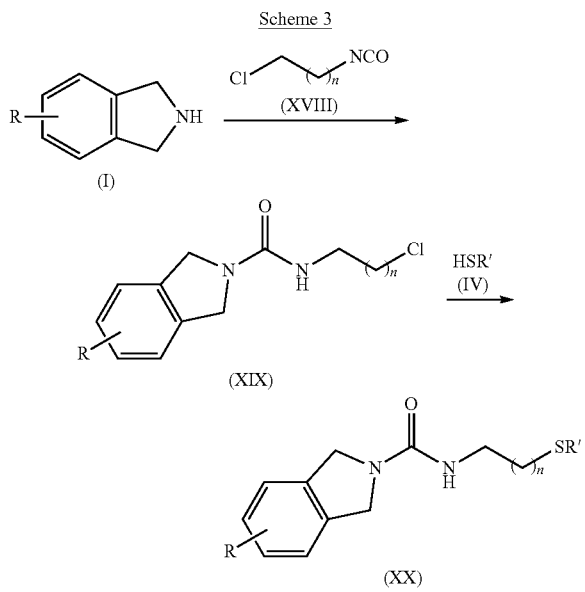

Scheme 3

The compounds thus prepared can be purified following conventional methods such as crystallization, distillation/vacuum distillation, flash chromatography over silica, and preparative liquid chromatography.

Some compounds of this invention contain a non-aromatic double bond or one or more asymmetric centers. Each of them occurs as a racemate or a racemic mixture, a single R enantiomer, a single S enantiomer, an individual diastereomer, a diastereometric mixture, a cis-isomer, or a trans-isomer. Compounds of such isomeric forms are within the scope of this invention. They can be present as a mixture or can be isolated using chiral synthesis or chiral separation technologies.

Importantly, compounds of this invention can be initially screened using an in vitro method to identify Cisd2 activation activity.

A typical in vitro screening method includes the following steps: (i) obtaining an initial level of Cisd2 in a batch of human embryonic kidney cells 293 (HEK-293 cells) that express Cisd2, (ii) treating the batch of HEK-293 cells with a compound of this invention, and (iii) analyzing the level of Cisd2 after the treatment, thereby determining the potency of the compound as a Cisd2 activator.

The compounds of this invention are effective Cisd2 activators as shown in examples below. They are useful in treating Cisd2-insufficient associated disorders, such as liver diseases, metabolic diseases, heart diseases, cachexia, and aging-associated diseases. They are also suitable for protecting a subject against doxorubicin-induced cardiotoxicity.

A compound of this invention is preferably formulated into a pharmaceutical composition containing a pharmaceutical carrier. The pharmaceutical composition is then given to a subject in need thereof to treat a Cisd2-insufficient associated disorder or protect against doxorubicin-induced cardiotoxicity.

To practice the method of the present invention, a composition having one or more of the above-described isoindoline compounds can be administered parenterally, orally, nasally, rectally, topically, or buccally.

The term "parenteral" as used herein encompasses subcutaneous, intracutaneous, intravenous, intraperitoneal, intramuscular, intraarticular, intraarterial, intrasynovial, intrasternal, intrathecal, intralesional, and intracranial injection of a sterile injectable composition. Indeed, the term refers to any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides). Fatty acid, such as oleic acid and its glyceride derivatives are useful in the preparation of injectables, as are natural pharmaceutically acceptable oils, such as olive oil and castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having an active compound can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

The term "treating" refers to application or administration of the compound to a subject with the purpose to cure, alleviate, relieve, alter, remedy, improve, or affect the disease, the symptom, or the predisposition. "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of other active agents.

Without further elaboration, it is believed that one skilled in the art can, based on the above description, utilize the present invention to its fullest extent. The following examples are to be construed as merely illustrative and not limitative of the remainder of the disclosure in any way whatsoever. All publications cited herein are hereby incorporated by reference in their entirety.

Set forth below are examples illustrating preparation and efficacy evaluation of compounds of this invention.

Example 1: Preparation of 1-(1,3-dihydro-2H-isoindol-2-yl)-2-(1,3-thiazol-2-ylsulfanyl)ethanone (Compound 1)

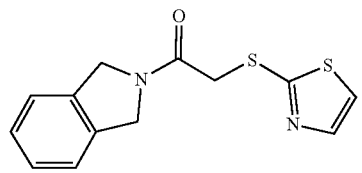 [SMILES: O=C(CSc1nccs1)N1Cc2ccccc2C1]

Compound 1 of this invention was prepared using a synthetic route depicted in Scheme 1 above. The two-step synthesis is described in detail below.

Step 1.
2-Bromo-1-(1,3-dihydro-2H-isoindol-2-yl)ethanone

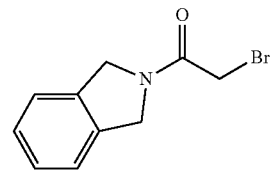 [SMILES: O=C(CBr)N1Cc2ccccc2C1]

Compound 2-bromo-1-(1,3-dihydro-2H-isoindol-2-yl) ethanone was prepared following a procedure described in Zhou et al., *Angew. Chem. Int. Ed.* 58, 1088-93 (2019). A solution of bromoacetyl bromide (0.41 mL, 4.74 mmol) in dichloromethane (5 mL) was added to a stirred solution of isoindoline (514 mg, 4.31 mmol) and triethylamine (0.67 mL, 4.74 mmol) in dichloromethane (10 mL) at 0° C. The resultant reaction mixture was warmed to room temperature gradually and stirred for 19 h. The reaction mixture was then quenched with water and subsequently was extracted with dichloromethane. The combined organic layers were dried over $MgSO_4$, filtered, and concentrated in vacuo to obtain a residue, which was purified by column chromatography using ethyl acetate (EtOAc) and hexanes (EtOAc/Hexanes=1/3) to obtain 2-bromo-1-(1,3-dihydro-2H-isoindol-2-yl)ethanone (628 mg, 61% yield. All percentages below refer to yields unless otherwise noted) as a beige solid.

$^1$H NMR (400 MHz, $CDCl_3$) δ 7.33-7.29 (m, 4H), 4.95 (s, 2H), 4.83 (s, 2H), 3.92 (s, 2H). LC-MS (ESI) m/z: 240.0 $[M+H]^+$.

Step 2. 1-(1,3-Dihydro-2H-isoindol-2-yl)-2-(1,3-thiazol-2-ylsulfanyl)ethanone

To a stirred solution of 2-bromo-1-(isoindolin-2-yl)ethan-1-one (246 mg, 1.02 mmol) in dichloromethane (14.5 mL) at 0° C., 2-Mercaptothiazole (100 mg, 0.85 mmol) and potassium carbonate (295 mg, 2.13 mmol) were added. The reaction mixture was warmed to room temperature gradually and stirred for 4 h. The mixture was quenched with water and the resulting mixture was extracted with dichloromethane. The combined organic layers were washed with brine, dried over $Na_2SO_4$, filtered, and concentrated in vacuo. The residue was purified by column chromatography (EtOAc/Hexanes=1/2) to yield 1-(1,3-dihydro-2H-isoindol-2-yl)-2-(1,3-thiazol-2-ylsulfanyl)ethanone (226 mg, 96%) as a brown solid.

$^1$H NMR (400 MHz, $CDCl_3$) δ 7.65 (d, 1H), 7.32-7.26 (m, 4H), 7.24 (d, 1H), 5.00 (s, 2H), 4.85 (s, 2H), 4.24 (s, 2H). LC-MS (ESI) m/z: 277.0 $[M+H]^+$.

Example 2: Preparation of 1-(5-methoxy-1,3-dihydro-2H-isoindol-2-yl)-2-(1,3-thiazol-2-ylsulfanyl)ethanone (Compound 2)

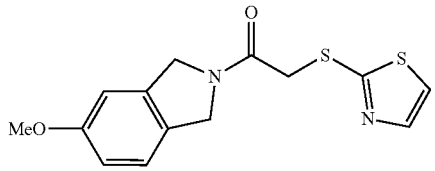 [SMILES: COc1ccc2c(c1)CN(C(=O)CSc1nccs1)C2]

Compound 2 was prepared in a procedure similar to that described in Example 1 above.

$^{1}$H NMR (300 MHz, CDCl$_{3}$, rotamers, about 1.1:1 ratio) δ 7.65 (d, 1H), 7.24-7.15 (m, 2H), 6.88-6.79 (m, 2H), 4.96 (s, 0.95H), 4.92 (s, 1.05H), 4.81 (s, 1.05H), 4.77 (s, 0.95H), 4.22 (s, 2H), 3.82 (s, 3H). LC-MS (ESI) m/z: 307.0 [M+H]$^{+}$.

Example 3: Preparation of 1-(5-hydroxy-1,3-dihydro-2H-isoindol-2-yl)-2-(1,3-thiazol-2-ylsulfanyl)ethanone (Compound 3)

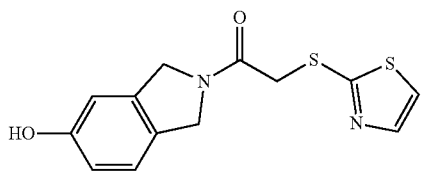 [SMILES: O=C(CSc1nccs1)N1Cc2ccc(O)cc2C1]

A 1 M solution of boron tribromide in heptane (0.68 mL, 0.68 mmol) was added to a stirred solution of 1-(5-methoxy-1,3-dihydro-2H-isoindol-2-yl)-2-(1,3-thiazol-2-ylsulfanyl)ethanone (53 mg, 0.17 mmol) in dichloromethane (5 mL) at 0° C. The resultant reaction mixture was warmed to room temperature gradually, stirred for 15 h, then cooled to 0° C., followed by addition of methanol (10 mL). After concentrated to a residue, it was purified by column chromatography (EtOAc/Hexanes=2/1) to provide 1-(5-hydroxy-1,3-dihydro-2H-isoindol-2-yl)-2-(1,3-thiazol-2-ylsulfanyl)ethanone (16 mg, 32%) as a white solid.

$^{1}$H NMR (300 MHz, CD$_{3}$OD, rotamers, about 1:1 ratio) δ 7.67 (d, 1H), 7.49 (d, 1H), 7.13 (d, 1H), 6.76-6.73 (m, 2H), 4.95 (s, 1H), 4.91 (s, 1H), 4.68 (s, 1H), 4.66 (s, 1H), 4.26 (s, 2H). LC-MS (ESI) m/z: 293.0 [M+H]$^{+}$.

Example 4: Preparation of 1-(4-fluoro-1,3-dihydro-2H-isoindol-2-yl)-2-(1,3-thiazol-2-ylsulfanyl)ethanone (Compound 4)

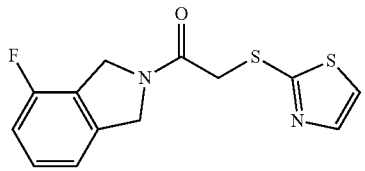 [SMILES: O=C(CSc1nccs1)N1Cc2cccc(F)c2C1]

Compound 4 was prepared in a manner similar to that described in Example 1.

$^{1}$H NMR (300 MHz, CDCl$_{3}$, rotamers, about 6:5 ratio) δ7.66-7.64 (m, 1H), 7.35-7.26 (m, 1H), 7.24 (d, 1H), 7.08 (dd, 1H), 7.00 (dd, 1H), 5.04 (s, 2H), 4.88 (s, 0.91H), 4.87 (s, 1.09H), 4.24 (s, 1.09H), 4.22 (s, 0.91H). LC-MS (ESI) m/z: 295.0 [M+H]$^{+}$.

Example 5: Preparation of 1-(5-fluoro-1,3-dihydro-2H-isoindol-2-yl)-2-(1,3-thiazol-2-ylsulfanyl)ethanone (Compound 5)

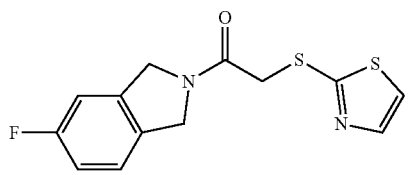 [SMILES: O=C(CSc1nccs1)N1Cc2ccc(F)cc2C1]

Compound 5 was prepared in a manner similar to that described in Example 1.

$^{1}$H NMR (400 MHz, CDCl$_{3}$, rotamers, about 1:1 ratio) δ 7.64 (d, 1H), 7.26-7.21 (m, 2H), 7.04-6.96 (m, 2H), 4.99 (s, 1H), 4.96 (s, 1H), 4.82 (s, 1H), 4.79 (s, 1H), 4.22 (s, 2H). LC-MS (ESI) m/z: 295.0 [M+H]$^{+}$, 317.0 [M+Na]$^{+}$.

Example 6: Preparation of 1-(5,6-difluoro-1,3-dihydro-2H-isoindol-2-yl)-2-(1,3-thiazol-2-ylsulfanyl)ethanone (Compound 6)

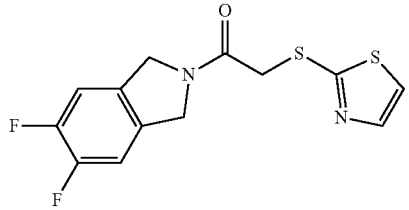 [SMILES: O=C(CSc1nccs1)N1Cc2cc(F)c(F)cc2C1]

Step 1. 5,6-Difluoro-1H-isoindole-1,3(2H)-dione

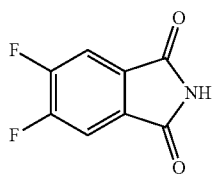 [SMILES: O=C1NC(=O)c2cc(F)c(F)cc21]

5,6-Difluoro-isoindole-1,3-dione was prepared according to a procedure described in Hahn et al., US Application Publication 2011/0034450 A1. A solution of 5,6-difluoroisobenzofuran-1,3-dione (200 mg, 1.08 mmol) in formamide (3 mL) was stirred at 130° C. for 2 h, after which it was cooled to room temperature and poured into ice-cold water. A white solid (53 mg) was precipitated and collected by filtration. The aqueous layer was extracted with EtOAc and the combined organic layers were dried over MgSO$_{4}$, filtered, and concentrated in vacuo to provide the second batch of 5,6-difluoro-isoindole-1,3-dione (72 mg). This gave a total of 125 mg of 5,6-difluoro-1H-isoindole-1,3(2H)-dione (68%) as a white solid.

LC-MS (ESI) m/z: 182.0 [M-H]$^{-}$.

Step 2. 5,6-Difluoro-2,3-dihydro-1H-isoindole

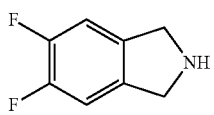

5,6-Difluoroisoindoline was prepared according to a procedure described in Giuliano et al., US Patent Application Publication 2017/0275301 A1. Boron trifluoride diethyl etherate (0.98 mL, 7.96 mmol) was added dropwise to a suspension solution of 5,6-dichloroisoindoline-1,3-dione (125 mg, 0.68 mmol) and sodium tetrahydridoborate (270 mg, 7.14 mmol) in THF (10 mL) at room temperature. The mixture was heated at 80° C. for 15 h, then cooled to 0° C. and quenched with 10% aqueous solution of sodium hydroxide to pH=13. The resultant mixture was extracted with EtOAc three times. The combined EtOAc layers were dried over $MgSO_4$, filtered, and concentrated in vacuo. The residue was purified by column chromatography (MeOH/$CH_2Cl_2$=1/10) to provide 5,6-difluoro-2,3-dihydro-1H-isoindole (59 mg, 56%) as a white solid.

LC-MS (ESI) m/z: 156.1 [M+H]$^+$.

Step 3. 1-(5,6-Difluoro-1,3-dihydro-2H-isoindol-2-yl)-2-(1,3-thiazol-2-ylsulfanyl)ethanone Compound 6 was prepared in a manner similar to that described in Example 1.

$^1$H NMR (300 MHz, $CDCl_3$) δ 7.64 (d, 1H), 7.24 (d, 1H), 7.12 (d, 1H), 7.07 (d, 1H), 4.96 (s, 2H), 4.79 (s, 2H), 4.20 (s, 2H). LC-MS (ESI) m/z: 313.0 [M+H]$^+$.

Example 7: Preparation of 1-(5-chloro-1,3-dihydro-2H-isoindol-2-yl)-2-(1,3-thiazol-2-ylsulfanyl)ethanone (Compound 7)

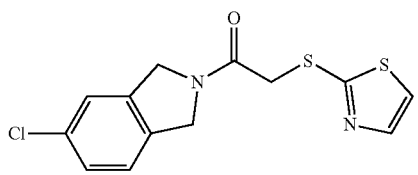 [SMILES: O=C(CSc1nccs1)N1Cc2ccc(Cl)cc2C1]

Compound 7 was prepared in a manner similar to that described in Example 6.

$^1$H NMR (400 MHz, $CDCl_3$, rotamers, about 1:1 ratio) δ 7.64 (dd, 1H), 7.31-7.19 (m, 4H), 4.98 (s, 1H), 4.97 (s, 1H), 4.82 (s, 1H), 4.80 (s, 1H), 4.21 (s, 2H). LC-MS (ESI) m/z: 333.0 [M+Na]$^+$.

Example 8: Preparation of 1-(5,6-dichloro-1,3-dihydro-2H-isoindol-2-yl)-2-(1,3-thiazol-2-ylsulfanyl)ethanone (Compound 8)

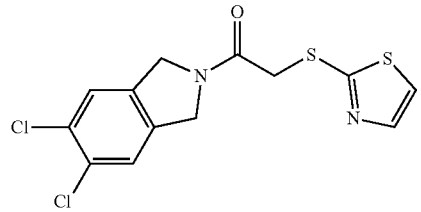 [SMILES: O=C(CSc1nccs1)N1Cc2cc(Cl)c(Cl)cc2C1]

Step 1. 5,6-Dichloro-2,3-dihydro-1H-isoindole

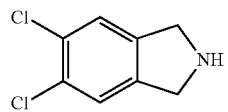

The title compound was prepared in a manner similar to that described in Step 2, Example 6 above.

$^1$H NMR (300 MHz, $CDCl_3$) δ 7.32 (s, 2H), 4.18 (s, 4H). LC-MS (ESI) m/z: 188.0 [M+H]$^+$.

Step 2. 1-(5,6-Dichloro-1,3-dihydro-2H-isoindol-2-yl)-2-(1,3-thiazol-2-ylsulfanyl)ethanone Compound 8 was prepared in a manner similar to that described in Example 1.

$^1$H NMR (400 MHz, $CDCl_3$) δ 7.64 (d, 1H), 7.40 (s, 1H), 7.37 (s, 1H), 7.24 (d, 1H), 4.97 (s, 2H), 4.79 (s, 2H), 4.20 (s, 2H). LC-MS (ESI) m/z: 345.0 [M+H]$^+$.

Example 9: Preparation of methyl 2-[(1,3-thiazol-2-ylsulfanyl)acetyl]-2,3-dihydro-1H-isoindole-5-carboxylate (Compound 9)

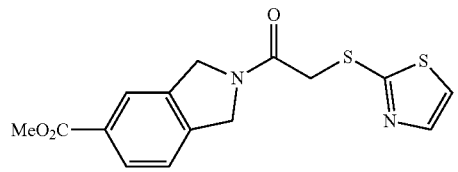 [SMILES: COC(=O)c1ccc2c(c1)CN(C(=O)CSc1nccs1)C2]

Step 1. Methyl 2-benzyl-2,3-dihydro-1H-isoindole-5-carboxylate

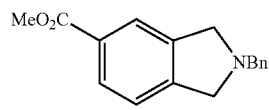 [SMILES: COC(=O)c1ccc2c(c1)CN(Cc1ccccc1)C2]

Methyl 2-benzyl-2,3-dihydro-1H-isoindole-5-carboxylate was prepared according to a procedure described in Frederickson et al., International Application Publication WO 2008/044034 A1. Benzylamine (204 uL, 1.86 mmol) in tetrahydrofuran (3 mL) was added to a stirred solution of methyl 3,4-bis-(bromomethyl)benzoate (600 mg, 1.86 mmol) and trimethylamine (0.56 mL, 4 mmol) in tetrahydrofuran (3 mL). The resulting mixture was stirred at room temperature for 3 h and then concentrated in vacuo. The residue was dissolved in EtOAc and washed with water. The organic layer was dried over $Na_2SO_4$, filtered, and concentrated in vacuo. The crude product was used for next step without further purification.

Step 2. Methyl 2,3-dihydro-1H-isoindole-5-carboxylate

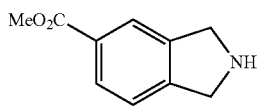

Methyl 2-benzyl-2,3-dihydro-1H-isoindole-5-carboxylate (548 mg) was hydrogenated over 10% Pd/C (130 mg) in isoproponal (15 mL) at 60° C. for 23 h. The reaction mixture was filtrated through Celite and the filtrate was concentrated in vacuo to give crude methyl 2,3-dihydro-1H-isoindole-5-carboxylate (270 mg, 75%), which was used for next step directly without further purification.

Step 3. Methyl 2-[(1,3-thiazol-2-ylsulfanyl)acetyl]-2,3-dihydro-1H-isoindole-5-carboxylate Compound 9 was prepared in a manner similar to that described in Example 1.
$^1$H NMR (300 MHz, $CDCl_3$, rotamers, about 1:1 ratio) δ 8.01 (d, 1H), 7.97 (d, 1H), 7.65 (d, 1H), 7.38 (d, 0.5H), 7.35 (d, 0.5H), 7.24 (d, 1H), 5.05 (s, 1H), 5.04 (s, 1H), 4.88 (s, 2H), 4.233 (s, 1H), 4.228 (s, 1H), 3.94 (s, 3H). LC-MS (ESI) m/z: 335.0 $[M+H]^+$.

Example 10: Preparation of 1-(5-nitro-1,3-dihydro-2H-isoindol-2-yl)-2-(1,3-thiazol-2-ylsulfanyl)ethanone (Compound 10)

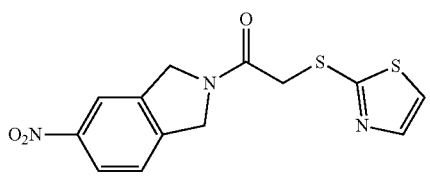 [SMILES: O=C(CSc1nccs1)N1Cc2ccc([N+](=O)[O-])cc2C1]

Step 1. 5-Nitro-2,3-dihydro-1H-isoindole

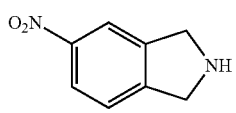 [SMILES: O=[N+]([O-])c1ccc2c(c1)CNC2]

5-Nitroisoindoline was prepared according to a procedure described in Barbosa et al., International Application Publication WO 2011/140488 A1. A solution of fuming $HNO_3$ (1 mL) and conc. $H_2SO_4$ (95%, 1 mL) was added dropwise to a solution of isoindoline (1.05 mL, 8.39 mmol) in conc. $H_2SO_4$ (95%, 5 mL) at 0° C. The reaction was stirred at 0° C. for 1 hour and then poured into ice-cold water slowly. The resulting mixture was neutralized with a saturated aqueous solution of sodium bicarbonate and a 0.5 N aqueous solution of sodium hydride. The reaction was extracted with EtOAc, and the combined organic layers were dried over $MgSO_4$, filtered and concentrated in vacuo to yield 5-nitro-2,3-dihydro-1H-isoindole (1155 mg, 84%) as a brown-red gum. LC-MS (ESI) m/z: 165.1 $[M+H]^+$.

Step 2. 1-(5-Nitro-1,3-dihydro-2H-isoindol-2-yl)-2-(1,3-thiazol-2-ylsulfanyl)ethanone Compound 10 was prepared in a manner similar to that described in Example 1.
$^1$H NMR (400 MHz, $CDCl_3$, rotamers, about 1.1:1 ratio) δ8.23-8.21 (m, 1H), 8.17 (d, 1H), 7.643 (d, 0.52H), 7.635 (s, 0.48H), 7.48 (d, 0.52H), 7.46 (d, 0.48H), 7.25 (d, 1H), 5.13 (s, 2H), 4.93 (s, 2H), 4.23 (s, 1.05H), 4.22 (s, 0.95H). LC-MS (ESI) m/z: 322.0 $[M+H]^+$.

Example 11: Preparation of 1-(1,3-dihydro-2H-isoindol-2-yl)-2-[(5-methyl-1,3-thiazol-2-yl)sulfanyl]ethanone (Compound 11)

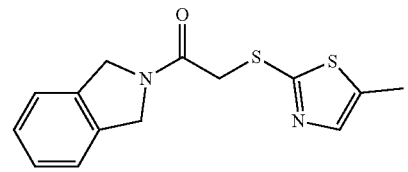 [SMILES: Cc1cnc(SCC(=O)N2Cc3ccccc3C2)s1]

Step 1. 5-Methyl-1,3-thiazole-2-thiol

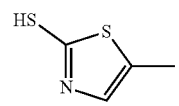

Compound 5-methyl-1,3-thiazole-2-thiol was prepared according to a procedure described in Glick et al., International Application Publication WO 2019/023147 A1. A solution of 2-bromo-5-methylthiazole (300 mg, 1.68 mmol) and sodium hydrosulfide (186 mg, 3.31 mmol) in ethanol (15 mL) was stirred at 80° C. for 48 h under argon. The reaction mixture was cooled to 0° C., and then the pH value of solution was adjusted to 2 with a 2 N aqueous solution of hydrochloric acid. The resulting mixture was extracted with EtOAc. The organic layer was dried over $MgSO_4$, filtered and concentrated in vacuo. The residue was purified by column chromatography (EtOAc/Hexanes=1/7 to 1/2) to provide 5-methyl-1,3-thiazole-2-thio (29 mg, 13%) as a white solid.
$^1$H NMR (400 MHz, d6-DMSO) δ 12.89 (s, 1H), 7.01 (s, 1H), 2.16 (s, 3H). LC-MS (ESI) m/z: 132.0 $[M+H]^+$.

Step 2. 1-(1,3-Dihydro-2H-isoindol-2-yl)-2-[(5-methyl-1,3-thiazol-2-yl)sulfanyl]ethanone Compound 11 was prepared in a manner similar to that described in Example 1. $^1$H NMR (400 MHz, $CDCl_3$) δ

7.31-7.26 (m, 5H), 4.97 (s, 2H), 4.84 (s, 2H), 4.15 (s, 2H), 2.40 (d, 3H). LC-MS (ESI) m/z: 291.0 [M+H]+.

Example 12: Preparation of 1-(5-fluoro-1,3-dihydro-2H-isoindol-2-yl)-2-[(5-methyl-1,3-thiazol-2-yl)sulfanyl]ethanone (Compound 12)

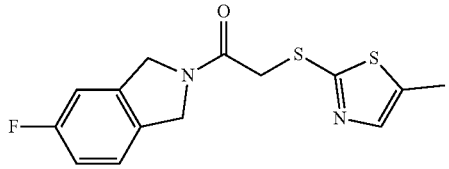 [SMILES: Cc1cnc(SCC(=O)N2Cc3ccc(F)cc3C2)s1]

Compound 12 was prepared in a manner similar to that described in Example 1.

1H NMR (400 MHz, CDCl3, rotamers, about 1:1 ratio) δ 7.29-7.28 (m, 1H), 7.25-7.20 (m, 1H), 7.04-6.96 (m, 2H), 4.97 (s, 1H), 4.94 (s, 1H), 4.81 (s, 1H), 4.79 (s, 1H), 4.14 (s, 1H), 4.13 (s, 1H), 2.41 (d, 3H). LC-MS (ESI) m/z: 309.1 [M+H]+.

Example 13: Preparation of 1-(1,3-dihydro-2H-isoindol-2-yl)-2-(pyridin-2-ylsulfanyl)ethanone (Compound 13)

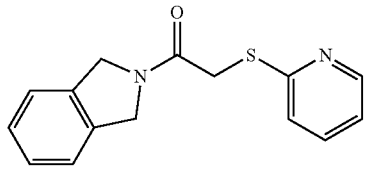 [SMILES: O=C(CSc1ccccn1)N1Cc2ccccc2C1]

Compound 13 was prepared in a manner similar to that described in Example 1.

1H NMR (400 MHz, d6-DMSO) δ 8.41-8.39 (m, 1H), 7.66 (ddd, 1H), 7.39-7.30 (m, 5H), 7.11 (ddd, 1H), 5.02 (s, 2H), 4.66 (s, 2H), 4.21 (s, 2H). LC-MS (ESI) m/z: 271.1 [M+H]+.

Example 14: Preparation of 1-(5-methoxy-1,3-dihydro-2H-isoindol-2-yl)-2-(pyridin-2-ylsulfanyl)ethanone (Compound 14)

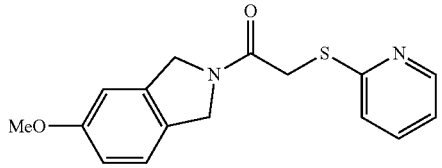 [SMILES: COc1ccc2c(c1)CN(C(=O)CSc1ccccn1)C2]

Compound 14 was prepared in a manner similar to that described in Example 1.

1H NMR (300 MHz, CDCl3, rotamers, about 1.1:1 ratio) δ 8.38 (d, 1H), 7.50 (dd, 1H), 7.30-7.16 (m, 2H), 6.99 (dd, 1H), 6.87-6.80 (m, 2H), 5.03 (s, 0.95H), 4.99 (s, 1.05H), 4.81 (s, 1.05H), 4.77 (s, 1.05H), 4.15 (s, 2H), 3.82 (s, 3H). LC-MS (ESI) m/z: 301.1 [M+H]+.

Example 15: Preparation of 1-(5-amino-1,3-dihydro-2H-isoindol-2-yl)-2-(pyridin-2-ylsulfanyl)ethanone (Compound 15)

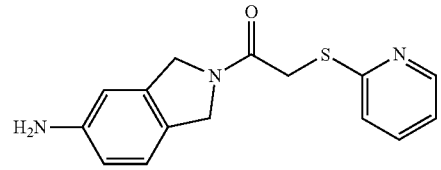 [SMILES: Nc1ccc2c(c1)CN(C(=O)CSc1ccccn1)C2]

Step 1. 2,2,2-Trifluoro-1-(5-nitro-1,3-dihydro-2H-isoindol-2-yl)ethanone

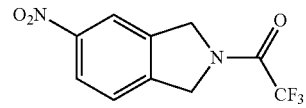

Compound 2,2,2-trifluoro-1-(5-nitro-1,3-dihydro-2H-isoindol-2-yl)ethanone was prepared according to a procedure described in Abe et al., International Application Publication WO 2004/046107 A1. Trifluoroacetic anhydride (1.12 mL, 8.08 mmol) was added to a solution of 5-nitroisoindoline (1.11 g, 6.76 mmol) and triethylamine (1.34 mL, 8.08 mmol) in dichloromethane (15 mL) at 0° C. The mixture was warmed to room temperature gradually and stirred for 15 h. The mixture was filtered through Celite and the filtrate was washed with a saturated aqueous solution of sodium bicarbonate. The aqueous layer was separated and extracted with dichloromethane. The combined organic layers were dried over MgSO4, filtered, and concentrated in vacuo. The residue was purified by column chromatography (EtOAc//Hexanes=1/4) to provide 2,2,2-trifluoro-1-(5-nitro-1,3-dihydro-2H-isoindol-2-yl)ethanone (455 mg, 26%) as a salmon solid.

Step 2. 1-(5-Amino-1,3-dihydro-2H-isoindol-2-yl)-2,2,2-trifluoroethanone

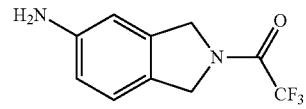

Compound 1-(5-Amino-1,3-dihydro-2H-isoindol-2-yl)-2,2,2-trifluoroethanone was prepared according to a method described in Chen et al., Synth. Commun. 48, 2475-84 (2018). Hydrazine monohydrate (420 μL, 8.64 mmol) was added to a mixture of 2,2,2-trifluoro-1-(5-nitro-1,3-dihydro-2H-isoindol-2-yl)ethanone (450 mg, 1.73 mmol) and 10% Pd/C (315 mg) in ethanol (15 mL) at 0° C. The reaction was warmed up to room temperature gradually and stirred for 15 h. The mixture was diluted with dichloromethane (20 mL) and filtered through Celite. The filtrate was concentrated in vacuo to provide a crude residue of 1-(5-amino-1,3-dihydro-2H-isoindol-2-yl)-2,2,2-trifluoroethanone (377 mg, 95%).

Step 3. tert-Butyl [2-(trifluoroacetyl)-2,3-dihydro-1H-isoindol-5-yl]carbamate

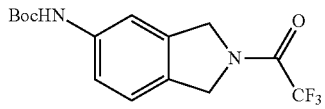 [SMILES: CC(C)(C)OC(=O)Nc1ccc2c(c1)CN(C(=O)C(F)(F)F)C2]

Compound tert-Butyl (2-(trifluoroacetyl)-2,3-dihydro-1H-isoindol-5-yl)carbamate was prepared according to a method described in Dahmann et al., International Application Publication WO 2012/101013 A1. A solution of 1-(5-amino-1,3-dihydro-2H-isoindol-2-yl)-2,2,2-trifluoroethanone (450 mg, 1.73 mmol) and di-tert-butyl dicarbonate (455 μL, 1.92 mmol) in acetonitrile (20 mL) was stirred at room temperature for 3 days. The solvent was removed under reduced pressure, a about 28% aqueous solution of ammonium hydroxide (5 mL) was then added to react with the excess of di-tert-butyl dicarbonate. The mixture was concentrated in vacuo and the resulting solid was washed with water. The light-salmon solid was collected through filtration to provide tert-Butyl [2-(trifluoroacetyl)-2,3-dihydro-1H-isoindol-5-yl]carbamate (439 mg, 81%).

Step 4. tert-Butyl 2,3-dihydro-1H-isoindol-5-ylcarbamate

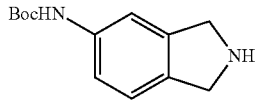 [SMILES: CC(C)(C)OC(=O)Nc1ccc2c(c1)CNC2]

Compound tert-butyl 2,3-dihydro-1H-isoindol-5-ylcarbamate was prepared according to a method described in Dahmann et al., WO 2012/101013. A 4 N solution of sodium hydroxide (9.5 mL) was added to a solution of tert-butyl [2-(trifluoroacetyl)-2,3-dihydro-1H-isoindol-5-yl]carbamate (439 mg, 1.33 mmol) in 1,4-dioxane (9.5 mL) at room temperature and stirred for 1.5 hours. The solvent was removed under reduced pressure. The residue was dissolved in dichloromethane and washed with brine. The organic layer was dried over MgSO$_4$, filtered, and concentrated in vacuo to provide a crude residue of tert-butyl 2,3-dihydro-1H-isoindol-5-ylcarbamate (317 mg, 100%).

Step 5. (Pyridin-2-ylsulfanyl)acetic acid

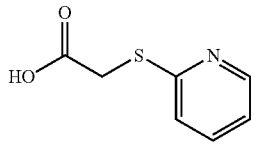 [SMILES: O=C(O)CSc1ccccn1]

Pyridine-2-thiol (1 g, 8.99 mmol) was added to a solution of chloroacetic acid (935 mg, 9.89 mmol) and NaHCO$_3$ (1.21 g, 14.38 mmol) in a mixed solvent (20 mL, ethanol/water=1/1) at room temperature. The mixture was heated under reflux for 5 h. Ethanol was removed under reduced pressure and a 12 N aqueous solution of hydrochloric acid was added to the residue at 0° C. until the solution became clear (pH=1). A 6 N aqueous solution of sodium hydroxide was then added until pH=6, and the resulting white precipitate filtered and collected to provide (pyridin-2-ylsulfanyl) acetic acid (853 mg, 56%).

Step 6. tert-Butyl {2-[(pyridin-2-ylsulfanyl)acetyl]-2,3-dihydro-1H-isoindol-5-yl}carbamate

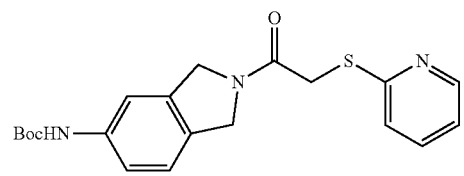 [SMILES: CC(C)(C)OC(=O)Nc1ccc2c(c1)CN(C(=O)CSc1ccccn1)C2]

A solution of tert-butyl 2,3-dihydro-1H-isoindol-5-ylcarbamate (110 mg, 0.47 mmol), (pyridin-2-ylsulfanyl)acetic acid (139 mg, 0.562 mmol), 2-(1H-benzotriazol-1-yl)-1,1,3,3-tetramethyluronium hexafluorophosphate (266 mg, 0.70 mmol), and cesium carbonate (305 mg, 0.94 mmol) in N,N-dimethylformamide was stirred at room temperature for 15 hour. The solvent was removed under reduced pressure, dichloromethane and brine were then added and the layers were separated. The aqueous layer was extracted with dichloromethane and the combined organic layers were dried over MgSO$_4$, filtered, and concentrated in vacuo. The residue was purified by column chromatography (EtOAc/Hexanes=1/1) to provide tert-butyl {2-[(pyridin-2-ylsulfanyl)acetyl]-2,3-dihydro-1H-isoindol-5-yl}carbamate (118 mg, 65%) as a gray solid.

Step 7. 1-(5-Amino-1,3-dihydro-2H-isoindol-2-yl)-2-(pyridin-2-ylsulfanyl)ethanone A mixture of tert-butyl {2-[(pyridin-2-ylsulfanyl)acetyl]-2,3-dihydro-1H-isoindol-5-yl}carbamate (54 mg, 0.14 mmol) in a 4 N solution of hydrochloric acid in 1,4-dioxane (2 mL) was stirred at room temperature for 15 hours. The solvent was removed under reduced pressure, dichloromethane and a saturated aqueous solution of sodium bicarbonate were then added and the layers were separated. The aqueous layer was extracted with dichloromethane and the combined organic layers were dried over MgSO$_4$, filtered, and concentrated in vacuo. The residue was purified by column chromatography (MeOH/CH$_2$Cl$_2$=1/30) to provide Compound 15, i.e., 1-(5-amino-1,3-dihydro-2H-isoindol-2-yl)-2-(pyridin-2-ylsulfanyl)ethanone (20 mg, 50%) as a white solid.

$^1$H NMR (400 MHz, d6-DMSO, rotamers, about 1:1 ratio) δ8.41-8.39 (m, 1H), 7.67-7.63 (m, 1H), 7.36 (dd, 1H), 7.13-7.10 (m, 1H), 6.98 (dd, 1H), 6.53-6.50 (m, 2H), 5.10 (s, 2H), 4.85 (s, 1H), 4.81 (s, 1H), 4.51 (s, 1H), 4.47 (s, 1H), 4.179 (s, 1H), 4.176 (s, 1H). LC-MS (ESI) m/z: 286.1 [M+H]$^+$.

Example 16: Preparation of 1-(5-fluoro-1,3-dihydro-2H-isoindol-2-yl)-2-(pyridin-2-ylsulfanyl)ethanone (Compound 16)

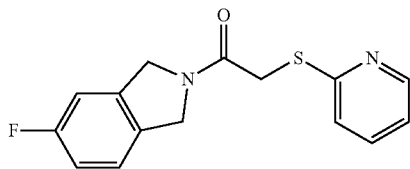

Compound 16 was prepared in a manner similar to that described in Example 1.

$^1$H NMR (400 MHz, CDCl$_3$, rotamers, about 1:1 ratio) δ 8.37 (d, 1H), 7.50 (ddd, 1H), 7.30-7.20 (m, 2H), 7.03-6.97 (m, 3H), 5.06 (s, 1H), 5.03 (s, 1H), 4.82 (s, 1H), 4.79 (s, 1H), 4.14 (s, 2H). LC-MS (ESI) m/z: 289.1 [M+H]$^+$.

Example 17: Preparation of 1-(1,3-dihydro-2H-isoindol-2-yl)-2-[(6-methylpyridin-2-yl)sulfanyl]ethanone (Compound 17)

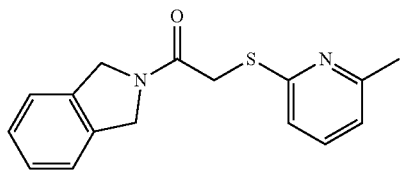 [SMILES: Cc1cccc(SCC(=O)N2Cc3ccccc3C2)n1]

Compound 17 was prepared in a manner similar to that described in Example 16.

$^1$H NMR (300 MHz, CDCl$_3$) δ 7.38 (dd, 1H), 7.30-7.26 (m, 4H), 7.09 (d, 1H), 6.82 (d, 1H), 5.12 (s, 2H), 4.84 (s, 2H), 4.10 (s, 2H), 2.39 (s, 3H). LC-MS (ESI) m/z: 285.1 [M+H]$^+$.

Example 18: Preparation of 2-[(6-chloropyridin-2-yl)sulfanyl]-1-(1,3-dihydro-2H-isoindol-2-yl)ethanone (Compound 18)

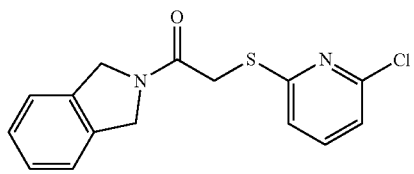 [SMILES: O=C(CSc1cccc(Cl)n1)N1Cc2ccccc2C1]

Step 1. 2-(tert-Butylsulfanyl)-6-chloropyridine

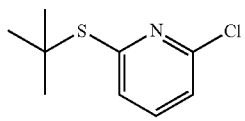

Compound 2-(tert-Butylsulfanyl)-6-chloropyridine was prepared following a method described in WO 2014/209034 A1. 2-Methylpropane-2-thiol (419 μL, 3.71 mmol) was added to a solution of 2,6-dichloropyridine (500 mg, 3.38 mmol) and cesium carbonate (2.20 g, 6.75 mmol) in anhydrous N,N-dimethylformamide (DMF, 5 mL) at room temperature. The resulting mixture was stirred at 80° C. for 15 hours, and then cooled to room temperature. The reaction was diluted with EtOAc and washed with brine. The organic layer was dried over MgSO$_4$, filtered and concentrated in vacuo to provide 2-(tert-butylsulfanyl)-6-chloropyridine (223 mg, 33%) as a yellow oil.

$^1$H NMR (400 MHz, CDCl$_3$) δ 7.43 (dd, 1H), 7.15 (dd, 1H), 7.04 (dd, 1H), 1.56 (s, 9H).

Step 2. 6-Chloropyridine-2-thiol

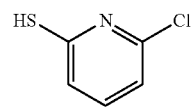

A 1 M solution of boron tribromide in heptane (1.10 mL, 1.1 mmol) was added to a solution of 2-(tert-butylthio)-6-chloropyridine (223 mg, 1.1 mmol) in anhydrous dichloromethane (2 mL) at 0° C. The reaction was warmed up to room temperature gradually and stirred for 15 h. More boron tribromide (1.1 mL, 1.1 mmol) was added and stirred at room temperature for another 5 hours. The reaction was quenched by the addition of methanol, and the resulting mixture was concentrated in vacuo. The residue was purified by column chromatography (EtOAc/Hexanes=1/1) to provide 6-chloropyridine-2-thiol with inseparable by-product (59 mg) as a yellow oil.

Step 3. 2-[(6-Chloropyridin-2-yl)sulfanyl]-1-(1,3-dihydro-2H-isoindol-2-yl)ethanone Compound 18 was prepared in a manner similar to that described in Example 1.

$^1$H NMR (300 MHz, CDCl$_3$) δ 7.44 (dd, 1H), 7.31-7.26 (m, 4H), 7.19 (d, 1H), 6.98 (d, 1H), 5.18 (s, 2H), 4.85 (s, 2H), 4.07 (s, 2H). LC-MS (ESI) m/z: 305.0 [M+H]$^+$.

Example 19: Preparation of 1-(1,3-dihydro-2H-isoindol-2-yl)-2-[(5-methyl-1,3,4-thiadiazol-2-yl)sulfanyl]ethanone (Compound 19)

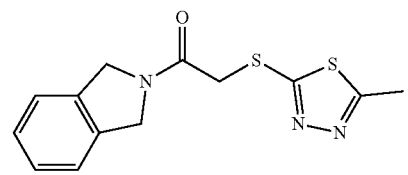 [SMILES: Cc1nnc(SCC(=O)N2Cc3ccccc3C2)s1]

Compound 19 was prepared in a manner similar to that described in Example 1.

$^1$H NMR (300 MHz, CDCl$_3$) δ 7.31-7.26 (m, 4H), 5.02 (s, 2H), 4.85 (s, 2H), 4.35 (s, 2H), 2.72 (s, 3H). LC-MS (ESI) m/z: 292.0 [M+H]$^+$.

Example 20: Preparation of 2-[(5-amino-1,3,4-thiadiazol-2-yl)sulfanyl]-1-(1,3-dihydro-2H-isoindol-2-yl)ethanone (Compound 20)

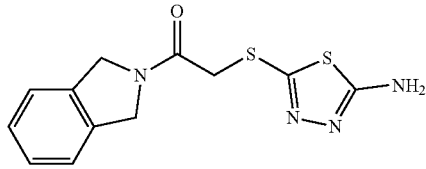

Step 1. tert-Butyl (5-sulfanyl-1,3,4-thiadiazol-2-yl)carbamate

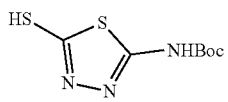

Di-tert-butyl pyrocarbonate (480 mg, 2.2 mmol) was added to a stirred solution of 2-amino-5-mercapto-1,3,4-thiadiazole (270 mg, 2.03 mmol) and sodium hydroxide (88 mg, 2.2 mmol) in a mixed solvent (4 mL, tert-butanol/water=1/1) at room temperature. The resulting mixture was stirred at room temperature for 19 hours, diluted with water, and then extracted with EtOAc to remove excess di-tert-butyl pyrocarbonate. A solution of potassium hydrogen sulfate (333 mg in 2.7 mL water) was added to aqueous layer and the resulting mixture was extracted with EtOAc. The organic layer was dried over Na$_2$SO$_4$, filtered, and concentrated in vacuo to provide tert-butyl (5-sulfanyl-1,3,4-thiadiazol-2-yl)carbamate (320 mg, 63%).
LC-MS (ESI) m/z: 234.0 [M+H]$^+$.

Step 2. 2-[(5-Amino-1,3,4-thiadiazol-2-yl)sulfanyl]-1-(1,3-dihydro-2H-isoindol-2-yl)ethanone Compound 20 was prepared in a manner similar to that described in Example 1.
$^1$H NMR (400 MHz, d6-DMSO) δ 7.36-7.28 (m, 4H), 4.92 (s, 2H), 4.67 (s, 2H), 4.23 (s, 2H). LC-MS (ESI) m/z: 293.0 [M+H]$^+$.

Example 21: Preparation of 1-(1,3-dihydro-2H-isoindol-2-yl)-2-(1H-imidazol-2-ylsulfanyl)ethanone (Compound 21)

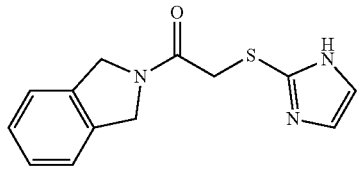 [SMILES: O=C(CSc1ncc[nH]1)N1Cc2ccccc2C1]

Compound 21 was prepared in a manner similar to that described in Example 1.
$^1$H NMR (400 MHz, CDCl$_3$) δ 7.33-7.26 (m, 4H), 7.07 (s, 2H), 4.90 (s, 2H), 4.87 (s, 2H), 3.76 (s, 2H). LC-MS (ESI) m/z: 260.1 [M+H]$^+$.

Example 22: Preparation of 1-(1,3-dihydro-2H-isoindol-2-yl)-2-(pyrimidin-2-ylsulfanyl)ethanone (Compound 22)

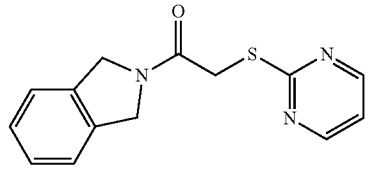

A mixture of isoindoline (190 μL, 1.68 mmol), trimethylamine (235 μL, 1.68 mmol), 2-(pyrimidin-2-ylthio)acetic acid (189 mg, 1.11 mmol), and 2-(1H-benzotriazole-1-yl)-1,1,3,3-tetramethyluronium hexafluorophosphate (636 mg, 1.68 mmol) in acetonitrile (5 mL) was stirred at room temperature for 15 hours. The mixture was diluted with EtOAc and washed with a saturated aqueous solution of ammonium chloride. The organic layer was dried over MgSO$_4$, filtered and concentrated in vacuo. The residue was purified by column chromatography (EtOAc/Hexanes=2/1) and the obtained solid was washed with chloroform to remove the undissolved impurity. The filtrate was concentrated and washed with EtOAc to provide Compound 22, i.e., 1-(1,3-dihydro-2H-isoindol-2-yl)-2-(pyrimidin-2-ylsulfanyl)ethanone (65.6 mg, 22%) as a gray solid.
$^1$H NMR (300 MHz, CDCl$_3$) δ 8.44 (d, 2H), 7.25-7.19 (m, 4H), 6.91 (dd, 1H), 4.99 (s, 2H), 4.79 (s, 2H), 4.06 (s, 2H). LC-MS (ESI) m/z: 272.0 [M+H]$^+$.

Example 23: Preparation of 1-(1,3-dihydro-2H-isoindol-2-yl)-3-(1,3-thiazol-2-ylsulfanyl)propan-1-one (Compound 23)

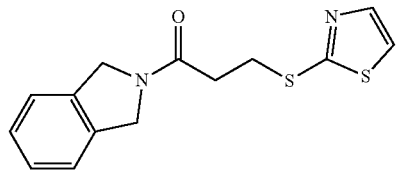 [SMILES: O=C(CCSc1nccs1)N1Cc2ccccc2C1]

Step 1. 3-Chloro-1-(1,3-dihydro-2H-isoindol-2-yl)propan-1-one

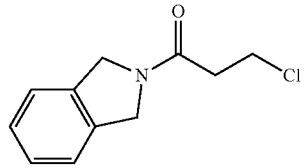 [SMILES: O=C(CCCl)N1Cc2ccccc2C1]

3-Chloropropanoyl chloride (0.3 mL, 3.2 mmol) was added to a stirred solution of isoindoline (0.3 mL, 2.64 mmol) and diisopropylethylamine (0.92 mL, 5.28 mmol) in dichloromethane (10 mL) in an ice bath. The reaction was warmed up to room temperature gradually and stirred for 15 hours. The mixture was diluted with dichloromethane and extracted with a saturated aqueous solution of ammonium chloride. The two layers were separated and the aqueous layer was extracted with dichloromethane. The combined organic layers were dried over MgSO₄, filtered and concentrated in vacuo. The residue was purified by column chromatography (EtOAc/Hexanes=1/3) to provide 3-chloro-1-(1,3-dihydro-2H-isoindol-2-yl)propan-1-one (63 mg, 11%) as a white solid.

$^1$H NMR (300 MHz, CDCl₃) δ 7.31-7.27 (m, 4H), 4.85 (s, 2H), 4.82 (s, 2H), 3.90 (t, 2H), 2.87 (t, 2H).

Step 2. 1-(1,3-Dihydro-2H-isoindol-2-yl)-3-(1,3-thiazol-2-ylsulfanyl)propan-1-one Compound 23 was prepared in a manner similar to that described in Example 1.

$^1$H NMR (300 MHz, CDCl₃) δ 7.67 (d, 1H), 7.30-7.22 (m, 5H), 4.82 (s, 2H), 4.79 (s, 2H), 3.59 (t, 2H), 2.93 (t, 2H). LC-MS (ESI) m/z: 291.0 [M+H]⁺.

Example 24: Preparation of 1-(5-fluoro-1,3-dihydro-2H-isoindol-2-yl)-3-(pyridin-2-ylsulfanyl)propan-1-one (Compound 24)

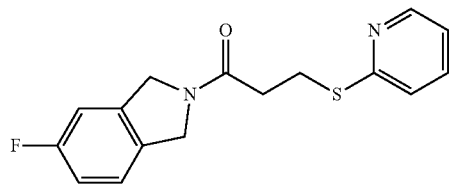 [SMILES: O=C(CCSc1ccccn1)N1Cc2ccc(F)cc2C1]

Compound 24 was prepared in a manner similar to that described in Example 21. $^1$H NMR (400 MHz, CD₃OD, rotamers, about 1:1 ratio) δ 8.40 (dd, 1H), 7.59 (ddd, 1H), 7.34-7.26 (m, 2H), 7.09-7.00 (m, 3H), 4.84 (s, 1H), 4.80 (s, 1H), 4.73 (s, 1H), 4.70 (s, 1H), 3.47 (t, 2H), 2.88 (t, 2H). LC-MS (ESI) m/z: 303.1 [M+H]⁺.

Example 25: Preparation of N-[2-(pyridin-2-ylsulfanyl)ethyl]-1,3-dihydro-2H-isoindole-2-carboxamide (Compound 25)

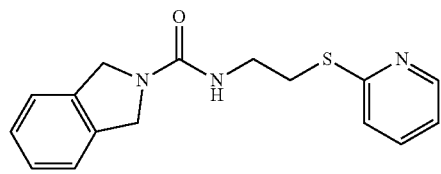 [SMILES: O=C(NCCSc1ccccn1)N1Cc2ccccc2C1]

Step 1. N-(2-Chloroethyl)-1,3-dihydro-2H-isoindole-2-carboxamide

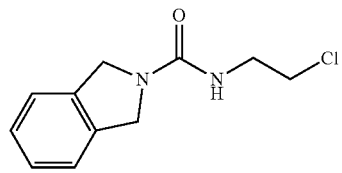 [SMILES: O=C(NCCCl)N1Cc2ccccc2C1]

N-(2-Chloroethyl)-1,3-dihydro-2H-isoindole-2-carboxamide was prepared according to A method described in U.S. Pat. No. 5,726,197. 1-Chloro-2-isocyanatoethane (107 µL, 1.26 mmol) was added to a solution of isoindoline (95 µL, 0.84 mmol) in THF (4 mL) at room temperature and stirred for 10 minutes. The solvent was removed under reduced pressure and the residue was washed with ether. The light-green solid was collected to provide N-(2-chloroethyl)-1,3-dihydro-2H-isoindole-2-carboxamide (226 mg, quant.). LC-MS (ESI) m/z: 225.1 [M+H]⁺.

Step 2. N-[2-(Pyridin-2-ylsulfanyl)ethyl]-1,3-dihydro-2H-isoindole-2-carboxamide A solution of N-(2-chloroethyl)-1,3-dihydro-2H-isoindole-2-carboxamide (40 mg, 0.18 mmol) in DMF (2 mL) was added to a solution of pyridine-2-thiol (24 mg, 0.22 mmol) and sodium hydride (8.5 mg, 0.213 mmol) in DMF (2 mL) at 0° C. The reaction was warmed to room temperature gradually and stirred for 15 hours. The reaction was cooled to 0° C., EtOAc and brine was added sequentially. The organic layer was separated, dried over MgSO₄, filtered, and concentrated in vacuo. The residue was purified by column chromatography (EtOAc/CH₂Cl₂=1/2) to provide Compound 25, i.e., N-[2-(pyridin-2-ylsulfanyl)ethyl]-1,3-dihydro-2H-isoindole-2-carboxamid (33 mg, 63%) as a white solid.

$^1$H NMR (300 MHz, CDCl₃) δ 8.44 (d, 1H), 7.50 (dd, 1H), 7.28-7.25 (m, 5H), 7.02 (dd, 1H), 5.59 (s, 1H), 4.64 (s, 4H), 3.69-3.63 (m, 2H), 3.40 (t, 2H). LC-MS (ESI) m/z: 300.0 [M+H]⁺.

Example 26: Preparation of 2,2-difluoro-1-(5-fluoro-1,3-dihydro-2H-isoindol-2-yl)-2-(pyridin-2-ylsulfanyl)ethanone (Compound 26)

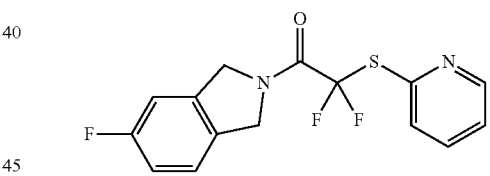

Compound 26 of this invention was prepared following a synthetic route depicted in Scheme 2 above.

Step 1. 2-Bromo-2,2-difluoro-1-(5-fluoro-1,3-dihydro-2H-isoindol-2-yl)ethanone

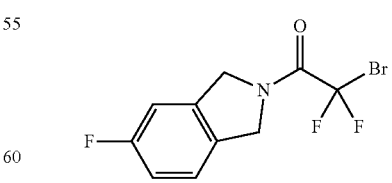

A mixture of 5-fluoroisoindoline hydrochloride (0.3 g, 1.73 mmol) and triethylamine (0.6 mL, 4.32 mmol) in dichloromethane (8 mL) was stirred at 0° C. for 10 minutes, and 2-bromo-2,2-difluoroacetyl bromide (0.18 mL, 1.9 mmol) was added. The mixture was warmed up to room temperature and stirred for 17 h, then dichloromethane and water were added. The aqueous layer was separated and extracted with dichloromethane. The combined organic layers were dried over MgSO$_4$, filtered, and concentrated in vacuo. The residue was purified by column chromatography (EtOAc/Hexanes=1/5) to provide 2-bromo-2,2-difluoro-1-(5-fluoro-1,3-dihydro-2H-isoindol-2-yl)ethanone (411 mg, 81%) as a white solid. LC-MS (ESI) m/z: 315.9 [M+Na]$^+$.

Step 2. 2,2-Difluoro-1-(5-fluoro-1,3-dihydro-2H-isoindol-2-yl)-2-(pyridin-2-ylsulfanyl)ethanone A solution of 2-bromo-2,2-difluoro-1-(5-fluoro-1,3-dihydro-2H-isoindol-2-yl)ethanone (100 mg, 0.36 mmol.) in N,N-dimethylformamide (1 mL) was added to a solution of pyridine-2-thiol (60.4 mg, 0.54 mmol) and sodium hydride (43 mg, 1.08 mmol) in N,N-dimethylformamide (1.0 mL) at 0° C. The reaction was heated at 60° C. for 5 hours, cooled to room temperature, and then the solvent was removed under reduced pressure. The residue was dissolved in EtOAc and the resulting mixture was washed brine. The organic layer was dried over MgSO$_4$, filtered, and concentrated in vacuo. The residue was purified by column chromatography (EtOAc/Hexanes=16/84) to provide Compound 26, i.e., 2,2-difluoro-1-(5-fluoro-1,3-dihydro-2H-isoindol-2-yl)-2-(pyridin-2-ylsulfanyl)ethanone (17.8 mg, 15%) as a brown solid.

$^1$H NMR (300 MHz, CDCl$_3$, rotamers, about 1:1 ratio) δ 8.57 (d, 1H), 7.74-7.67 (m, 2H), 7.31-7.19 (m, 2H), 7.05-6.95 (m, 2H), 5.16 (s, 1H), 5.13 (s, 1H), 4.86 (s, 1H), 4.83 (s, 1H). LC-MS (ESI) m/z: 325.0 [M+H]$^+$.

Example 27: Preparation of 1-(1,3-dihydro-2H-isoindol-2-yl)-2,2-difluoro-3-(pyridin-2-ylsulfanyl)propan-1-one (Compound 27)

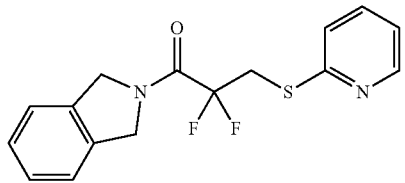 [SMILES: O=C(N1Cc2ccccc2C1)C(F)(F)CSc1ccccn1]

Compound 27 of this invention was prepared following a synthetic route depicted in Scheme 2 above.

Step 1. Ethyl 2,2-difluoro-3-(pyridin-2-ylsulfanyl)propanoate

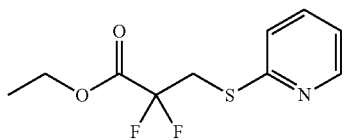 [SMILES: CCOC(=O)C(F)(F)CSc1ccccn1]

A mixture of 2-mercaptopyridine (28 mg, 0.25 mmol) and potassium carbonate (65 mg, 0.47 mmol) were sequentially added to a solution of ethyl 3-bromo-2,2-difluoropropanoate (50 mg, 0.23 mmol) in acetonitrile (1 mL) at room temperature. The mixture was heated in a sealed tube at 70° C. for 18 hours. The reaction was cooled to room temperature and then filtered through Celite. The filtrate was concentrated in vacuo and the residue was purified by column chromatography (EtOAc/Hexanes=1/19) to provide ethyl 2,2-difluoro-3-(pyridin-2-ylsulfanyl)propanoate (25 mg, 44%) as a colorless gel. LC-MS (ESI) m/z: 248.1 [M+H]$^+$.

Step 2. 1-(1,3-Dihydro-2H-isoindol-2-yl)-2,2-difluoro-3-(pyridin-2-ylsulfanyl)propan-1-one A 0.25 M aqueous solution of lithium hydroxide (1 mg, 0.25 mmol) was added to a solution of ethyl 2,2-difluoro-3-(pyridin-2-ylsulfanyl)propanoate (25 mg, 0.1 mmol) in acetonitrile (1 mL) at room temperature. After stirring at room temperature for 2 hours, the reaction was quenched by the addition of a 0.25 M aqueous solution of hydrochloric acid. The resulting mixture was extracted with EtOAc and the organic layer was dried over Na$_2$SO$_4$, filtered, and concentrated in vacuo. The residue was used for next step with further purification.

A mixture of the residue (17 mg), hydroxybenzotriazole (11.5 mg, 0.085 mmol), dicyclohexylcarbodiimide (17.5 mg, 0.085 mmol), and isoindoline (10 mg, 0.085 mmol) was stirred at room temperature for 18 h. Water was added and the resulting mixture was extracted with EtOAc. The organic layer was dried over Na$_2$SO$_4$, filtered, and concentrated in vacuo. The residue was purified by column chromatography (EtOAc/Hexanes=1/9) to provide Compound 27, i.e., 1-(1,3-dihydro-2H-isoindol-2-yl)-2,2-difluoro-3-(pyridin-2-ylsulfanyl)propan-1-one (25 mg, 54%) as a colorless gel.

$^1$H NMR (400 MHz, CDCl$_3$) δ 8.37-8.36 (m, 1H), 7.51-7.47 (m, 1H), 7.31-7.22 (m, 5H) 7.02-6.99 (m, 1H), 5.12 (s, 2H), 4.85 (s, 2H), 4.19 (t, 2H). LC-MS (ESI) m/z: 321.1 [M+H]$^+$.

Example 28: Preparation of 1-(1,3-dihydro-2H-isoindol-2-yl)-2-(1,3-thiazol-2-ylsulfonyl)ethanone (Compound 28)

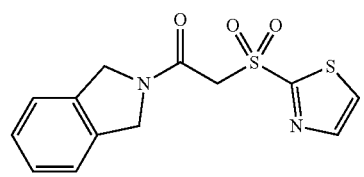

meta-Chloroperoxybenzoic acid (70% purity, 134 mg, 0.54 mmol) was added to a solution of 1-(1,3-dihydro-2H-isoindol-2-yl)-2-(1,3-thiazol-2-ylsulfanyl)-ethanone (50 mg, 0.18 mmol) in dichloromethane (5 mL) at 0° C. The mixture was warmed to room temperature gradually and stirred overnight. The reaction was quenched with a saturated aqueous solution of sodium thiosulfate and a saturated aqueous solution of sodium bicarbonate. The mixture was then extracted with dichloromethane. The organic layer was dried over Na$_2$SO$_4$, filtered and concentrated in vicuo. The residue was purified by column chromatography (EtOAc/Hexanes=1/1 to 2/1) to provide Compound 28, i.e., 1-(1,3-dihydro-2H-isoindol-2-yl)-2-(1,3-thiazol-2-ylsulfonyl)ethanone (68 mg, 99%) as a white solid.

$^1$H NMR (300 MHz, CDCl$_3$) δ 8.10 (d, 1H), 7.79 (d, 1H), 7.34-7.26 (m, 4H), 5.07 (s, 2H), 4.79 (s, 2H), 4.59 (s, 2H). LC-MS (ESI) m/z: 309.1 [M+H]$^+$.

Example 29: Preparation of 1-(5-methoxy-1,3-dihydro-2H-isoindol-2-yl)-2-(1,3-thiazol-2-ylsulfonyl)ethanone (Compound 29)

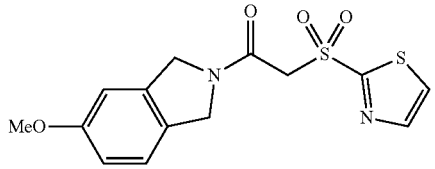 [SMILES: COc1ccc2c(c1)CN(C(=O)CS(=O)(=O)c1nccs1)C2]

Compound 29 was prepared in a manner similar to that described in Example 28.

$^1$H NMR (300 MHz, CDCl$_3$, rotamers, about 1.1:1 ratio) δ 8.09 (d, 1H), 7.79 (d, 1H), 7.17 (d, 1H), 6.86 (d, 1H), 6.79 (s, 1H), 5.02 (s, 0.95H), 4.98 (s, 1.05H), 4.74 (s, 1.05H), 4.71 (s, 0.95H), 4.57 (s, 2H), 3.81 (s, 3H). LC-MS (ESI) m/z: 339.1 [M+H]$^+$.

Example 30: Preparation of 1-(4-fluoro-1,3-dihydro-2H-isoindol-2-yl)-2-(1,3-thiazol-2-ylsulfonyl)ethanone (Compound 30)

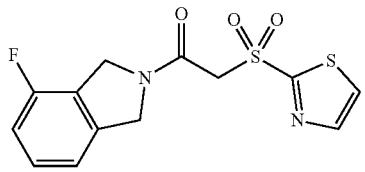 [SMILES: O=C(CS(=O)(=O)c1nccs1)N1Cc2cccc(F)c2C1]

Compound 30 was prepared in a manner similar to that described in Example 28.

$^1$H NMR (300 MHz, CDCl$_3$, rotamers, about 1:1 ratio) δ 8.10 (d, 1H), 7.81-7.80 (dd, 1H), 7.35-7.26 (m, 1H), 7.07 (d, 1H), 7.00 (dd, 1H), 5.10 (s, 2H), 4.83 (s, 1H), 4.81 (s, 1H), 4.59 (s, 1H), 4.57 (s, 1H). LC-MS (ESI) m/z: 349.0 [M+Na]$^+$.

Example 31: Preparation of 1-(5-fluoro-1,3-dihydro-2H-isoindol-2-yl)-2-(1,3-thiazol-2-ylsulfonyl)ethanone (Compound 31)

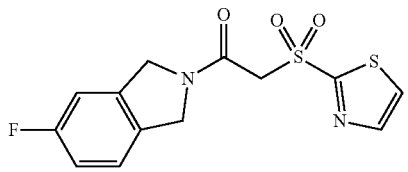 [SMILES: O=C(CS(=O)(=O)c1nccs1)N1Cc2ccc(F)cc2C1]

Compound 31 was prepared in a manner similar to that described in Example 28.

$^1$H NMR (400 MHz, CDCl$_3$, rotamers, about 1.1:1 ratio) δ 8.10 (d, 1H), 7.80 (d, 1H), 7.26-7.22 (m, 1H), 7.05-6.98 (m, 2H), 5.06 (s, 0.95H), 5.03 (s, 1.05H), 4.77 (s, 1.05H), 4.74 (s, 0.95H), 4.570 (s, 1.05H), 4.568 (s, 0.95H). LC-MS (ESI) m/z: 349.0 [M+Na]$^+$.

Example 32: Preparation of 1-(5,6-difluoro-1,3-dihydro-2H-isoindol-2-yl)-2-(1,3-thiazol-2-ylsulfonyl)ethanone (Compound 32)

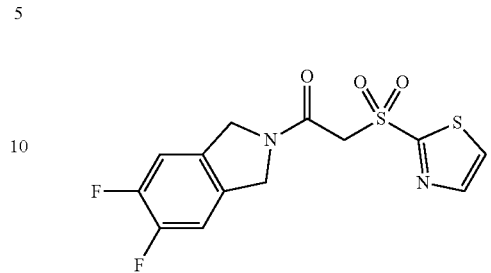

Compound 32 was prepared in a manner similar to that described in Example 28.

$^1$H NMR (300 MHz, CDCl$_3$) δ 8.10 (d, 1H), 7.81 (d, 1H), 7.12-7.07 (m, 2H), 5.03 (s, 2H), 4.74 (s, 2H), 4.56 (s, 2H). LC-MS (ESI) m/z: 367.0 [M+Na]$^+$.

Example 33: Preparation of 1-(5-chloro-1,3-dihydro-2H-isoindol-2-yl)-2-(1,3-thiazol-2-ylsulfonyl)ethanone (Compound 33)

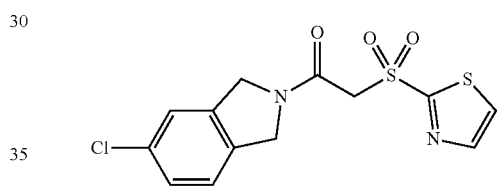

Compound 33 was prepared in a manner similar to that described in Example 28.

$^1$H NMR (400 MHz, CDCl$_3$, rotamers, about 1:1 ratio) δ 8.10 (d, 1H), 7.80 (d, 1H), 7.31-7.26 (m, 2H), 7.21 (d, 1H), 5.05 (s, 1H), 5.04 (s, 1H), 4.76 (s, 1H), 4.75 (s, 1H), 4.57 (s, 2H). LC-MS (ESI) m/z: 365.0 [M+Na]$^+$.

Example 34: Preparation of 1-(5,6-dichloro-1,3-dihydro-2H-isoindol-2-yl)-2-(1,3-thiazol-2-ylsulfonyl)ethanone (Compound 34)

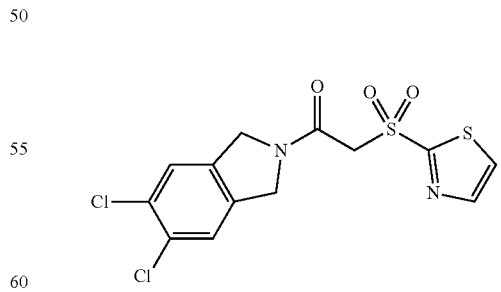

Compound 34 was prepared in a manner similar to that described in Example 28.

$^1$H NMR (400 MHz, CDCl$_3$) δ 8.10 (d, 1H), 7.81 (d, 1H), 7.39 (s, 2H), 5.04 (s, 2H), 4.74 (s, 2H), 4.56 (s, 2H). LC-MS (ESI) m/z: 398.9 [M+Na]$^+$.

Example 35: Preparation of methyl 2-[(1,3-thiazol-2-ylsulfonyl)acetyl]-2,3-dihydro-1H-isoindole-5-carboxylate (Compound 35)

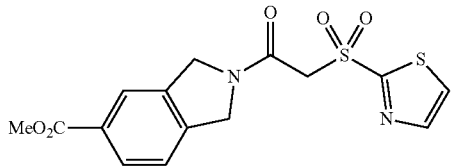 [SMILES: COC(=O)c1ccc2c(c1)CN(C(=O)CS(=O)(=O)c1nccs1)C2]

Compound 35 was prepared in a manner similar to that described in Example 28.

$^1$H NMR (300 MHz, CDCl$_3$, rotamers, about 1:1 ratio) δ 8.10 (d, 1H), 8.02 (d, 1H), 7.97 (s, 1H), 7.80 (d, 1H), 7.36 (d, 1H), 5.12 (s, 1H), 5.10 (s, 1H), 4.83 (s, 2H), 4.59 (s, 1H), 4.58 (s, 1H), 3.94 (s, 1.5H), 3.93 (s, 1.5H). LC-MS (ESI) m/z: 389.1 [M+Na]$^+$.

Example 36: Preparation of 1-(5-nitro-1,3-dihydro-2H-isoindol-2-yl)-2-(1,3-thiazol-2-ylsulfonyl)ethanone (Compound 36)

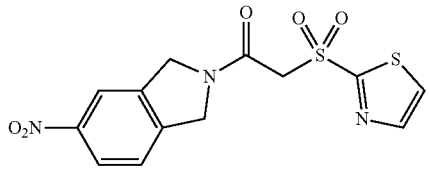 [SMILES: O=C(CS(=O)(=O)c1nccs1)N1Cc2ccc([N+](=O)[O-])cc2C1]

Compound 36 was prepared in a manner similar to that described in Example 28.

$^1$H NMR (300 MHz, CDCl$_3$, rotamers, about 1.1:1 ratio) δ 8.23 (d, 1H), 8.18 (s, 1H), 8.11 (d, 1H), 7.83-7.82 (m, 1H), 7.47 (d, 1H), 5.19 (s, 2H), 4.89 (s, 2H), 4.60 (s, 1.05H), 4.59 (s, 0.95H). LC-MS (ESI) m/z: 376.0 [M+Na]$^+$.

Example 37: Preparation of 1-(1,3-dihydro-2H-isoindol-2-yl)-2-[(5-methyl-1,3-thiazol-2-yl)sulfonyl]ethanone (Compound 37)

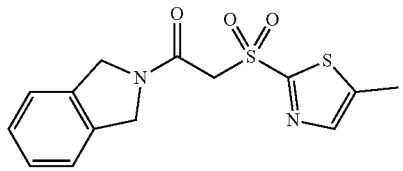 [SMILES: Cc1cnc(S(=O)(=O)CC(=O)N2Cc3ccccc3C2)s1]

Compound 37 was prepared in a manner similar to that described in Example 28.

$^1$H NMR (400 MHz, CDCl$_3$) δ 7.75 (s, 1H), 7.31-7.26 (m, 4H), 5.06 (s, 2H), 4.79 (s, 2H), 4.54 (s, 2H), 2.60 (s, 3H). LC-MS (ESI) m/z: 323.0 [M+H]$^+$.

Example 38: Preparation of 1-(1,3-dihydro-2H-isoindol-2-yl)-2-(pyridin-2-ylsulfonyl)ethanone (Compound 38)

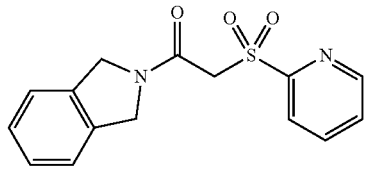 [SMILES: O=C(CS(=O)(=O)c1ccccn1)N1Cc2ccccc2C1]

Compound 38 was prepared in a manner similar to that described in Example 28. $^1$H NMR (300 MHz, CDCl$_3$) δ 8.78 (d, 1H), 8.12 (d, 1H), 7.99 (dd, 1H), 7.60-7.56 (m, 1H), 7.30-7.26 (m, 4H), 5.08 (s, 2H), 4.76 (s, 2H), 4.60 (s, 2H). LC-MS (ESI) m/z: 325.0 [M+Na]$^+$.

Example 39: Preparation of 1-(5-methoxy-1,3-dihydro-2H-isoindol-2-yl)-2-(pyridin-2-ylsulfonyl)ethanone (Compound 39)

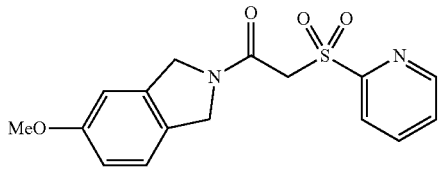 [SMILES: COc1ccc2c(c1)CN(C(=O)CS(=O)(=O)c1ccccn1)C2]

Compound 39 was prepared in a manner similar to that described in Example 28.

$^1$H NMR (300 MHz, CDCl$_3$, rotamers, about 1.1:1 ratio) δ 8.78 (d, 1H), 8.12 (d, 1H), 7.99 (dd, 1H), 7.60-7.56 (m, 1H), 7.17 (dd, 1H), 6.86 (d, 1H), 6.79 (d, 1H), 5.04 (s, 0.95H), 5.00 (s, 1.05H), 4.71 (s, 1.05H), 4.68 (s, 0.95H), 4.59 (s, 2H), 3.82 (s, 1.43H), 3.81 (s, 1.57H). LC-MS (ESI) m/z: 355.0 [M+Na]$^+$.

Example 40: Preparation of 1-(5-fluoro-1,3-dihydro-2H-isoindol-2-yl)-2-(pyridin-2-ylsulfonyl)ethanone (Compound 40)

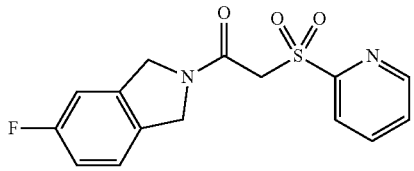 [SMILES: O=C(CS(=O)(=O)c1ccccn1)N1Cc2ccc(F)cc2C1]

Compound 40 was prepared in a manner similar to that described in Example 28.

$^1$H NMR (400 MHz, CDCl$_3$, rotamers, about 1.1:1 ratio) δ 8.78 (d, 1H), 8.11 (d, 1H), 7.99 (dd, 1H), 7.60-7.57 (m, 1H), 7.26-7.20 (m, 1H), 7.04-6.96 (m, 2H), 5.08 (s, 0.95H), 5.05 (s, 1.05H), 4.74 (s, 1.05H), 4.71 (s, 0.95H), 4.58 (s, 2H). LC-MS (ESI) m/z: 343.0 [M+Na]$^+$.

Example 41: Preparation of 1-(1,3-dihydro-2H-isoindol-2-yl)-2-[(6-methylpyridin-2-yl)sulfonyl]ethanone (Compound 41)

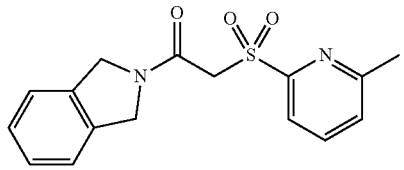 [SMILES: Cc1cccc(S(=O)(=O)CC(=O)N2Cc3ccccc3C2)n1]

Compound 41 was prepared in a manner similar to that described in Example 28.

$^1$H NMR (300 MHz, CDCl$_3$) δ 7.91 (d, 1H), 7.84 (dd, 1H), 7.40 (d, 1H), 7.33-7.26 (m, 4H), 5.09 (s, 2H), 4.76 (s, 2H), 4.59 (s, 2H), 2.65 (s, 3H). LC-MS (ESI) m/z: 317.1 [M+H]$^+$.

Example 42: Preparation of 2-[(6-chloropyridin-2-yl)sulfonyl]-1-(1,3-dihydro-2H-isoindol-2-yl)ethanone (Compound 42)

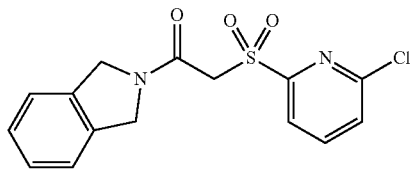 [SMILES: O=C(CS(=O)(=O)c1cccc(Cl)n1)N1Cc2ccccc2C1]

Compound 42 was prepared in a manner similar to that described in Example 28.

$^1$H NMR (400 MHz, CDCl$_3$) δ 8.04 (d, 1H), 7.93 (dd, 1H), 7.58 (d, 1H), 7.31-7.26 (m, 4H), 5.06 (s, 2H), 4.75 (s, 2H), 4.60 (s, 2H). LC-MS (ESI) m/z: 359.0 [M+Na]$^+$.

Example 43: Preparation of 1-(1,3-dihydro-2H-isoindol-2-yl)-2-(pyrimidin-2-ylsulfonyl)ethanone (Compound 43)

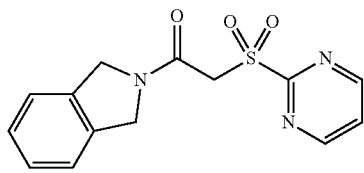 [SMILES: O=C(CS(=O)(=O)c1ncccn1)N1Cc2ccccc2C1]

Compound 43 was prepared in a manner similar to that described in Example 28. $^1$H NMR (300 MHz, CDCl$_3$) δ 8.98 (d, 2H), 7.58 (dd, 1H), 7.33-7.26 (m, 4H), 5.07 (s, 2H), 4.74 (s, 2H), 4.71 (s, 2H). LC-MS (ESI) m/z: 326.1 [M+Na]$^+$.

Example 44: Preparation of 1-(1,3-dihydro-2H-isoindol-2-yl)-2-[(1-oxidopyridin-4-yl)sulfonyl]ethanone (Compound 44)

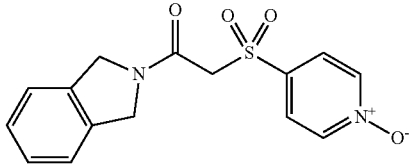 [SMILES: O=C(CS(=O)(=O)c1cc[n+]([O-])cc1)N1Cc2ccccc2C1]

Compound 44 was prepared in a manner similar to that described in Example 28.

$^1$H NMR (300 MHz, CDCl$_3$) δ 8.27 (d, 2H), 7.80 (d, 2H), 7.36-7.26 (m, 4H), 5.07 (s, 2H), 4.81 (s, 2H), 4.31 (s, 2H). LC-MS (ESI) m/z: 319.1 [M+H]$^+$.

Example 45: Preparation of 1-(1,3-dihydro-2H-isoindol-2-yl)-2-(phenylsulfonyl)-ethanone (Compound 45)

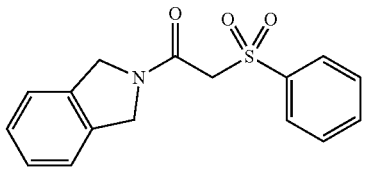

Compound 45 was prepared using a synthetic route depicted in Scheme 1 above.

A mixture of 2-bromo-1-(1,3-dihydro-2H-isoindol-2-yl)ethanone (50 mg, 0.21 mmol) and sodium benzenesulfinate (28 mg, 0.17 mmol) in PEG-400 (2 mL) was stirred at room temperature for 5 hours. The mixture was diluted with EtOAc and then washed with brine. The organic layer was separated, dried over MgSO$_4$, filtered, and concentrated in vacuo. The resultant residue was purified by column chromatography (EtOAc/Hexanes=1/2) to provide Compound 45, i.e., 1-(1,3-dihydro-2H-isoindol-2-yl)-2-(phenylsulfonyl)ethanone (25 mg, 40%) as a white solid.

$^1$H NMR (400 MHz, CDCl$_3$) δ 7.96 (d, 2H), 7.69 (dd, 1H), 7.58 (dd, 2H), 7.33-7.24 (m, 4H), 5.08 (s, 2H), 4.80 (s, 2H), 4.27 (s, 2H). LC-MS (ESI) m/z: 324.1 [M+Na]$^+$.

Example 46: Preparation of 1-(1,3-dihydro-2H-isoindol-2-yl)-2-(thiophen-2-ylsulfonyl)ethanone (Compound 46)

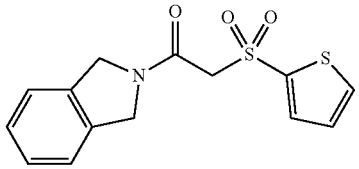

Step 1. Sodium thiophene-2-sulfinate

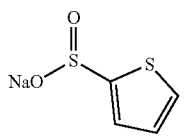

Sodium thiophene-2-sulfinate was prepared according to a method described in Bogonda et al., *Org. Lett.* 21, 3774-3779 (2019). A mixture of sodium sulfite (1.54 g, 12.2 mmol), sodium bicarbonate (1.03 g, 12.2 mmol), and thiophene-2-sulfonyl chloride (1.12 g, 6.1 mmol) in water (6 mL) was stirred at 80° C. for 4 hours. After cooling down to room temperature, water was removed in vacuo. Ethanol was then added to the white residue and the resultant heterogeneous solution was filtered. The filtrate was concentrated under reduced pressure and the sodium thiophene-2-sulfinate was obtained as white crystalline powders (832 mg, 80%).

Step 2. 1-(1,3-Dihydro-2H-isoindol-2-yl)-2-(thiophen-2-ylsulfonyl)ethanone

Compound 46 was prepared in a manner similar to that described in Example 45.
$^1$H NMR (300 MHz, CDCl$_3$) δ 7.79-7.76 (m, 2H), 7.34-7.26 (m, 4H), 7.18 (dd, 1H), 5.07 (s, 2H), 4.82 (s, 2H), 4.35 (s, 2H). LC-MS (ESI) m/z: 330.0 [M+Na]$^+$.

Example 47: Preparation of 2-(benzylsulfonyl)-1-(1,3-dihydro-2H-isoindol-2-yl)ethanone (Compound 47)

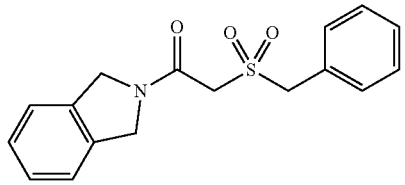 [SMILES: O=C(CS(=O)(=O)Cc1ccccc1)N1Cc2ccccc2C1]

Compound 47 was prepared in a manner similar to that described in Example 28.
$^1$H NMR (400 MHz, CDCl$_3$) δ 7.62-7.60 (m, 2H), 7.43-7.41 (m, 3H), 7.33-7.30 (m, 3H), 7.26-7.24 (m, 1H), 5.01 (s, 2H), 4.90 (s, 2H), 4.60 (s, 2H), 3.94 (s, 2H). LC-MS (ESI) m/z: 316.1 [M+H]$^+$.

Example 48: Preparation of 1-(1,3-dihydro-2H-isoindol-2-yl)-3-(1,3-thiazol-2-ylsulfonyl)propan-1-one (Compound 48)

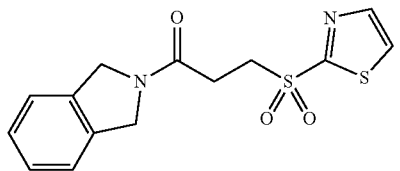 [SMILES: O=C(CCS(=O)(=O)c1nccs1)N1Cc2ccccc2C1]

Compound 48 was prepared in a manner similar to that described in Example 28.
$^1$H NMR (300 MHz, CDCl$_3$) δ 8.04 (d, 1H), 7.76 (d, 1H), 7.34-7.26 (m, 4H), 4.86 (s, 2H), 4.75 (s, 2H), 3.87 (t, 2H), 3.04 (t, 2H). LC-MS (ESI) m/z: 345.0 [M+Na]$^+$.

Example 49: Preparation of 1-(5-fluoro-1,3-dihydro-2H-isoindol-2-yl)-3-(pyridin-2-ylsulfonyl)propan-1-one (Compound 49)

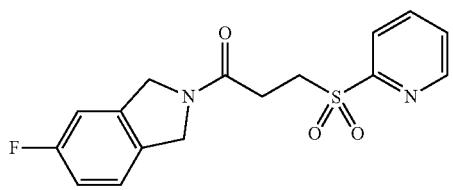 [SMILES: O=C(CCS(=O)(=O)c1ccccn1)N1Cc2ccc(F)cc2C1]

Compound 49 was prepared in a manner similar to that described in Example 28.
$^1$H NMR (300 MHz, CDCl$_3$, rotamers, about 1.1:1 ratio) δ 8.74 (d, 1H), 8.11 (d, 1H), 7.98 (ddd, 1H), 7.60-7.55 (m, 1H), 7.26-7.20 (m, 1H), 7.04-6.96 (m, 2H), 4.84 (s, 0.95H), 4.82 (s, 1.05H), 4.74 (s, 1.05H), 4.71 (s, 0.95H), 3.83 (t, 2H), 2.99 (t, 2H). LC-MS (ESI) m/z: 335.1 [M+H]$^+$.

Example 50: Preparation of 2,2-difluoro-1-(5-fluoro-1,3-dihydro-2H-isoindol-2-yl)-2-(pyridin-2-ylsulfonyl)ethanone (Compound 50)

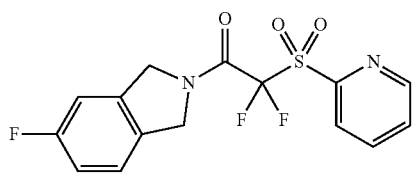 [SMILES: O=C(N1Cc2ccc(F)cc2C1)C(F)(F)S(=O)(=O)c1ccccn1]

Ruthenium(III) chloride n-hydrate (cat. 0.01%) was added to a solution of 2,2-difluoro-1-(5-fluoro-1,3-dihydro-2H-isoindol-2-yl)-2-(pyridin-2-ylsulfanyl)ethanone (Example 26) (20 mg, 0.06 mmol) and sodium periodate (26 mg, 0.12 mmol) in a mixed solvent (5.5 mL, acetonitrile/carbon tetrachloride/water=4/4/3) at room temperature and stirred for 15 h. EtOAc was added and the resulting mixture was washed with a saturated solution of sodium bicarbonate and a saturated solution of sodium thiosulfate. The organic layer was dried over MgSO$_4$, filtered, and concentrated in vacuo. The residue was purified by column chromatography (EtOAc/Hexanes=1/3) to provide Compound 50, i.e., 2,2-difluoro-1-(5-fluoro-1,3-dihydro-2H-isoindol-2-yl)-2-(pyridin-2-ylsulfonyl)ethanone (154 mg, 70%) as a white solid.

$^1$H NMR (400 MHz, CDCl$_3$, rotamers, about 1:1 ratio) δ 8.87 (d, 1H), 8.22 (d, 1H), 8.07 (ddd, 1H), 7.70 (dd, 1H), 7.28-7.22 (m, 1H), 7.06-6.98 (m, 2H), 5.30 (s, 1H), 5.27 (s, 1H), 4.92 (s, 1H), 4.90 (s, 1H), LC-MS (ESI) m/z: 357.0 [M+H]$^+$.

Example 51: Preparation of 2-[(1,3-thiazol-2-ylsulfonyl)acetyl]-2,3-dihydro-1H-isoindol-5-yl 5-[(3aS,4S,6aR)-2-oxohexahydro-1H-thieno[3,4-d]imidazol-4-yl]pentanoate (Compound 51)

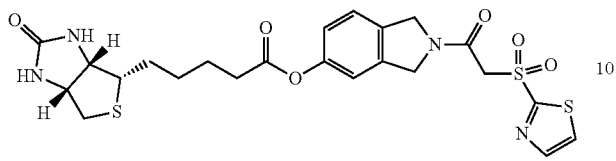

Compound meta-chloroperoxybenzoic acid (70% purity, 171 mg, 0.7 mmol) was added to a solution of 1-(5-hydroxy-1,3-dihydro-2H-isoindol-2-yl)-2-(1,3-thiazol-2-ylsulfanyl)ethanone (Example 3) (68 mg, 0.23 mmol) in THF (5 mL) at 0° C. The mixture was warmed to room temperature gradually and stirred for 15 h. The solvent was removed and the residue was washed with iced methanol to provide crude 1-(5-hydroxy-1,3-dihydro-2H-isoindol-2-yl)-2-(1,3-thiazol-2-ylsulfonyl)ethanone (33 mg) as a white solid.

A mixture of the crude (10 mg, 0.03 mmol), biotin (11.3 mg, 0.05 mmol), cesium carbonate (19.5 mg, 0.06 mmol), and (2-(1H-benzotriazol-1-yl)-1,1,3,3-tetramethyluronium hexafluorophosphate (17.4 mg, 0.05 mmol) in N,N-dimethylformamide (2 mL) was stirred at room temperature for 15 h. The solvent was removed and the residue was purified by column chromatography (MeOH/CH$_2$Cl$_2$=1/19) to provide Compound 51 2-[(1,3-thiazol-2-ylsulfonyl)acetyl]-2,3-dihydro-1H-isoindol-5-yl 5-[(3aS,4S,6aR)-2-oxohexahydro-1H-thieno[3,4-d]imidazol-4-yl]pentanoate (13.9 mg) as a white solid.

$^1$H NMR (300 MHz, CDCl$_3$) δ 8.10 (d, 1H), 7.80 (d, 1H), 7.30-7.26 (m, 1H), 7.03-7.00 (m, 2H), 5.05-5.01 (m, 3H), 4.78-4.68 (m, 3H), 4.57-4.50 (m, 3H), 4.40-4.30 (m, 1H), 3.24-3.14 (m, 1H), 3.00-2.90 (m, 1H), 2.68 (d, 1H), 2.66-2.54 (m, 2H), 1.81-1.70 (m, 6H). LC-MS (ESI) m/z: 573.1 [M+Na]$^+$.

Example 52: Preparation of 1-(1,3-dihydro-2H-isoindol-2-yl)-2,2-difluoro-2-(1,3-thiazol-2-ylsulfanyl)ethanone (Compound 52)

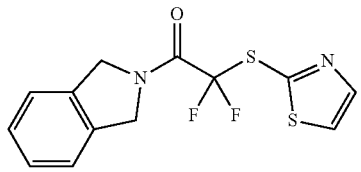 [SMILES: O=C(N1Cc2ccccc2C1)C(F)(F)Sc1nccs1]

Compound 52 was prepared in a manner similar to that described in Example 26.

$^1$H NMR (400 MHz, CDCl$_3$) δ 7.99 (d, 1H), 7.62 (d, 1H), 7.33-7.31 (m, 3H), 7.29-7.26 (m, 1H), 5.11 (s, 2H), 4.91 (s, 2H). LC-MS (ESI) m/z: 313.0 [M+H]$^+$.

Example 53: Preparation of 1-(1,3-dihydro-2H-isoindol-2-yl)-2,2-difluoro-2-(1,3-thiazol-2-ylsulfonyl)ethanone (Compound 53)

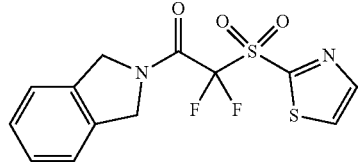 [SMILES: O=C(N1Cc2ccccc2C1)C(F)(F)S(=O)(=O)c1nccs1]

Compound 53 was prepared in a manner similar to that described in Example 28.

$^1$H NMR (400 MHz, CDCl$_3$) δ 8.24 (d, 1H), 8.01 (d, 1H), 7.35-7.25 (m, 4H), 5.27 (s, 2H), 4.95 (s, 2H). LC-MS (ESI) m/z: 345.0 [M+H]$^+$.

Example 54: Preparation of 1-(1,3-dihydro-2H-isoindol-2-yl)-2,2-difluoro-2-(1,3-thiazol-2-ylsulfinyl)ethanone (Compound 54)

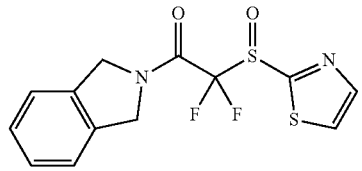 [SMILES: O=C(N1Cc2ccccc2C1)C(F)(F)S(=O)c1nccs1]

Compound 54 was prepared in a manner similar to that described in Example 28.

$^1$H NMR (300 MHz, CDCl$_3$) δ 8.06 (d, 1H), 7.80 (d, 1H), 7.33-7.26 (m, 4H), 5.12, 5.02 (ABq, 2H), 4.92 (s, 2H). LC-MS (ESI) m/z: 329.0 [M+H]$^+$.

Example 55: 1-(5-hydroxy-1,3-dihydro-2H-isoindol-2-yl)-2-(pyridin-2-ylsulfanyl)ethanone (Compound 55)

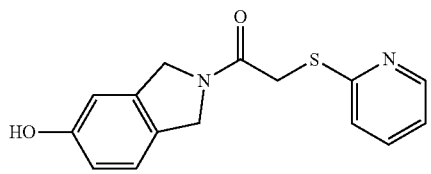 [SMILES: O=C(CSc1ccccn1)N1Cc2ccc(O)cc2C1]

A 1M solution of BBr$_3$ in heptane (4.0 mL, 4 mmol) was added to a solution of Compound 14 (300 mg, 0.99 mmol) in dichloromethane (7 mL) at 0° C. After stirring at 0° C. for 15 h, the reaction mixture was poured into an iced methanol and then concentrated in vacuo. The residue was dissolved in dichloromethane and the resulting solution was neutralized with a 1 N aqueous solution of sodium hydroxide. The organic layer was separated and washed with a 2 N aqueous solution of hydrochloric acid. The aqueous layer was reextracted with a 3% solution of methanol in dichloromethane three times. The combined organic layers were dried over MgSO$_4$, filtered, and concentrated in vacuo. The residue was purified by column chromatography (MeOH/CH$_2$Cl$_2$=1/9) to yield Compound 55 (78 mg, 27%).

¹H NMR (400 MHz, d6-DMSO, rotamers, about 1:1 ratio) δ 9.47 (s, 1H), 8.41-8.39 (m, 1H), 7.65 (ddd, 1H), 7.36 (d, 1H), 7.15-7.10 (m, 2H), 6.74-6.69 (m, 2H), 4.92 (s, 1H), 4.87 (s, 1H), 4.57 (s, 1H), 4.53 (s, 1H), 4.18 (s, 2H). LC-MS (ESI) m/z: 287.1 [M+H]⁺.

Example 56: Preparation of 1-(1,3-dihydro-2H-isoindol-2-yl)-2-[(3-fluorophenyl)sulfanyl]ethanone (Compound 56)

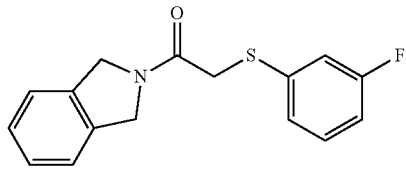 [SMILES: O=C(CSc1cccc(F)c1)N1Cc2ccccc2C1]

Compound 56 was prepared in a manner similar to that described in Example 1.

¹H NMR (400 MHz, CDCl₃) δ 7.32-7.17 (m, 7H), 6.93-6.88 (m, 1H), 4.93 (s, 2H), 4.83 (s, 2H), 3.82 (s, 2H). LC-MS (ESI) m/z: 288.1 [M+H]⁺.

Example 57: Preparation of 2-[(5-chlorothiophen-2-yl)sulfanyl]-1-(1,3-dihydro-2H-isoindol-2-yl)ethanone (Compound 57)

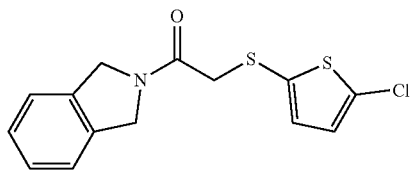 [SMILES: O=C(CSc1ccc(Cl)s1)N1Cc2ccccc2C1]

Step 1. Methyl 2-[(5-chiorothiophen-2-yl)thio]acetate

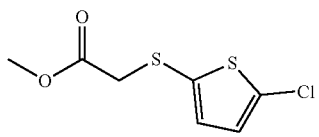

Tris(dibenzylideneacetone)dipalladium (116 mg, 0.13 mmol), Xantphos (146 mg, 0.25 mmol), N,N-diisopropylethylamine (0.88 mL, 5.1 mmol), and methyl 2-mercaptoacetate (0.23 mL, 2.53 mmol) were sequentially added to a solution of 2-bromo-5-chlorothiophene (0.28 mL, 2.53 mmol) in 1,4-dioxane (5 mL) at room temperature. The reaction was heated at 115° C. for 15 h, and then cooled to room temperature. The reaction was diluted with ethyl acetate and the resulting mixture was washed with brine. The organic layer was dried over MgSO₄, filtered, and concentrated in vacuo. The residue was purified by column chromatography (CH₂Cl₂/Hexanes=2/3) to provide methyl 2-[(5-chlorothiophen-2-yl)thio]acetate (573 mg, quant.) as a colorless oil.

Step 2. [(5-Chlorothiophen-2-yl)sulfanyl]acetic acid

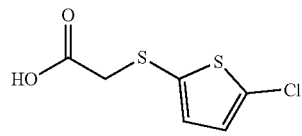

A mixture of methyl 2-[(5-chlorothiophen-2-yl)thio]acetate (573 mg, 2.53 mmol) and lithium hydroxide (378 mg, 5.1 mmoL) in a mixed solvent (10 mL, tetrahydrofuran/water=8.4/1.6) was stirred at room temperature for 15 h. The reaction was cooled to 0° C. and the pH value of the reaction was adjusted to 1 with conc. hydrochloric acid (5 drops). The mixture was extracted with brine and dichloromethane. The organic layer was dried over MgSO₄, filtered, and concentrated to provide a crude residue of [(5-chlorothiophen-2-yl)sulfanyl]acetic acid (640 mg, quant.) as a yellow oil.

Step 3. 2-[(5-Chlorothiophen-2-yl)sulfanyl]-1-(1,3-dihydro-2H-isoindol-2-yl)ethanone A mixture of isoindoline (0.21 mL, 1.87 mmol), N,N-diisopropylethylamine (0.65 mL, 3.74 mmol), [benzotriazol-1-yloxy(dimethylamino)methylidene]-dimethylazanium hexafluorophosphate (1064 mg, 2.81 mmol), and [(5-chlorothiophen-2-yl)sulfanyl]acetic acid (509 mg, 2.4 mmol) in N,N-dimethylformamide (4 mL) was stirred at room temperature for 15 h. The mixture was diluted with ethyl acetate and washed with brine. The organic layer was dried over MgSO₄, filtered, and concentrated in vacuo. The residue was purified by column chromatography (EtOAc/Hexanes=1/3) to provide Compound 57 (189 mg, 33%) as a salmon solid.

¹H NMR (400 NMR, CDCl₃) δ7.33-7.24 (m, 4H), 7.05 (d, 1H), 6.78 (d, 1H), 4.83-4.82 (m, 4H), 3.66 (s, 2H). LC-MS (ESI) m/z: 310.0 [M+H]⁺.

Example 58: Preparation of 2-[(2,5-difluorophenyl)sulfanyl]-1-(1,3-dihydro-2H-isoindol-2-yl)ethanone (Compound 58)

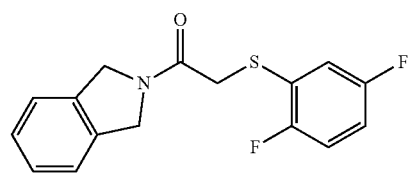 [SMILES: O=C(CSc1cc(F)ccc1F)N1Cc2ccccc2C1]

Compound 58 was prepared in a manner similar to that described in Example 1.

¹H NMR (400 MHz, CDCl₃) δ 7.33-7.26 (m, 5H), 7.03 (ddd, 1H), 6.96-6.90 (m, 1H), 4.95 (s, 2H), 4.82 (s, 2H), 3.81 (s, 2H). LC-MS (ESI) m/z: 306.1 [M+H]⁺.

Example 59: Preparation of 1-(1,3-dihydro-2H-isoindol-2-yl)-2-[(2-fluorophenyl)sulfanyl]ethanone (Compound 59)

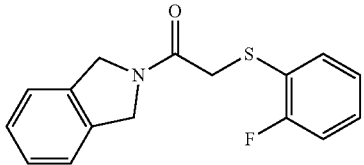

Compound 59 was prepared in a manner similar to that described in Example 1.

$^1$H NMR (400 MHz, CDCl$_3$) δ 7.59-7.55 (m, 1H), 7.31-7.25 (m, 5H), 7.13-7.06 (m, 2H), 4.94 (s, 2H), 4.80 (s, 2H), 3.78 (s, 2H). LC-MS (ESI) m/z: 288.1 [M+H]$^+$.

Example 60: Preparation of 2-[(2,4-difluorophenyl)sulfanyl]-1-(1,3-dihydro-2H-isoindol-2-yl)ethanone (Compound 60)

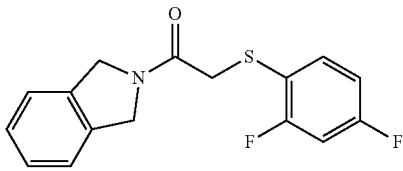 [SMILES: O=C(CSc1ccc(F)cc1F)N1Cc2ccccc2C1]

Compound 60 was prepared in a manner similar to that described in Example 1.

$^1$H NMR (400 MHz, CDCl$_3$) δ 7.60-7.54 (m, 1H), 7.33-7.26 (m, 4H), 6.88-6.83 (m, 2H), 4.94 (s, 2H), 4.78 (s, 2H), 3.71 (s, 2H). LC-MS (ESI) m/z: 306.1 [M+H]$^+$.

Example 61: Preparation of 2-[(4-aminophenyl)sulfanyl]-1-(1,3-dihydro-2H-isoindol-2-yl)ethanone (Compound 61)

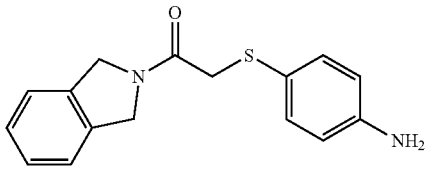

Step 1. 1-(1,3-Dihydro-2H-isoindol-2-yl)-2-[(4-nitrophenyl)sulfanyl]ethanone

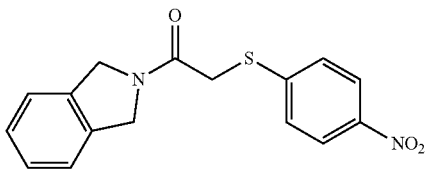 [SMILES: O=C(CSc1ccc([N+](=O)[O-])cc1)N1Cc2ccccc2C1]

A mixture of 2-bromo-1-(isoindolin-2-yl)ethan-1-one (50 mg, 0.208 mmol), sodium hydride (17 mg, 0.42 mmol), and 4-nitrobenzenethiol (40 mg, 0.208 mmol) in N,N-dimethylformamide (5 mL) was stirred at 0° C. for 30 min. The reaction was warmed up to room temperature gradually and stirred for 3 h. The mixture was diluted with dichloromethane and washed with brine. The organic layer was dried over MgSO$_4$, filtered, and concentrated in vacuo. The residue was purified by column chromatography (EtOAc/Hexanes=1/3 to 1/2) to provide 1-(1,3-dihydro-2H-isoindol-2-yl)-2-[(4-nitrophenyl)sulfanyl]ethanone (29 mg, 44%) as a yellow solid.

Step 2. 2-[(4-Aminophenyl)sulfanyl]-1-(1,3-dihydro-2H-isoindol-2-yl)ethanone

A saturated aqueous solution of ammonium chloride (2 mL) was added to a mixture of 1-(1,3-dihydro-2H-isoindol-2-yl)-2-[(4-nitrophenyl)sulfanyl]ethanone (20 mg, 0.06 mmol) and Fe (18 mg, 0.32 mmol) in ethanol (10 mL) at room temperature. The reaction was heated at 90° C. for 2 h and then cooled to room temperature. Dichloromethane was added and the resulting mixture was filtered through Celite. The filtrate was concentrated and the residue was dissolved in dichloromethane. The organic layer was washed with brine, dried over MgSO$_4$, filtered, and concentrated in vacuo. The residue was purified by column chromatography (EtOAc/Hexanes=2/1) to provide Compound 61 (12 mg, 66%) as a white solid.

$^1$H NMR (400 NMR, CDCl$_3$) δ7.35-7.22 (m, 6H), 6.61-6.58 (m, 2H), 4.84 (s, 2H), 4.80 (s, 2H), 3.73 (brs, 2H), 3.62 (s, 2H). LC-MS (ESI) m/z: 285.1 [M+H]$^+$.

Example 62: Preparation of 1-(1,3-dihydro-2H-isoindol-2-yl)-2-[(4-methylphenyl)sulfanyl]ethanone (Compound 62)

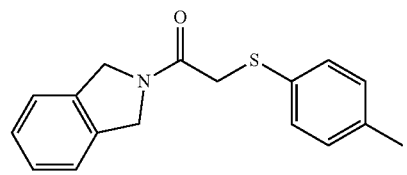 [SMILES: Cc1ccc(SCC(=O)N2Cc3ccccc3C2)cc1]

Compound 62 was prepared in a manner similar to that described in Example 1.

$^1$H NMR (400 NMR, CDCl$_3$) δ 7.41-7.38 (m, 2H), 7.32-7.23 (m, 4H), 7.12-7.10 (m, 2H), 4.89-4.88 (m, 2H), 4.82-4.81 (m, 2H), 3.73 (s, 2H), 2.31 (s, 3H). LC-MS (ESI) m/z: 284.2 [M+H]$^+$.

Example 63: Preparation of 1-(5-fluoro-1,3-dihydro-2H-isoindol-2-yl)-2-[(2-fluorophenyl)sulfanyl]ethanone (Compound 63)

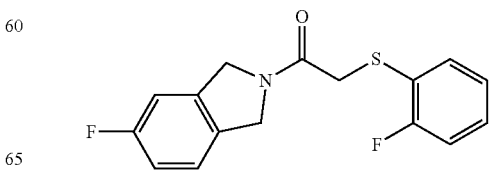

Compound 63 was prepared in a manner similar to that described in Example 1.

¹H NMR (400 MHz, CDCl₃, rotamers, about 1.1:1 ratio) δ 7.56 (ddd, 1H), 7.30-7.19 (m, 2H), 7.12-6.95 (m, 4H), 4.92 (s, 0.95H), 4.90 (s, 1.05H), 4.77 (s, 1.05H), 4.74 (s, 0.95H), 3.76 (s, 2H). LC-MS (ESI) m/z: 306.1 [M+H]⁺.

Example 64: Preparation of 1-(5-fluoro-1,3-dihydro-2H-isoindol-2-yl)-2-(phenylsulfanyl)ethanone (Compound 64)

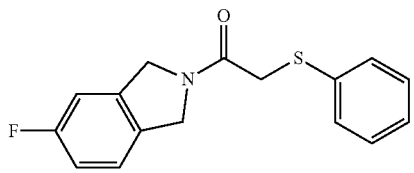

Compound 64 was prepared in a manner similar to that described in Example 1.

¹H NMR (400 MHz, CDCl₃, rotamers, about 1.1:1 ratio) δ 7.49-7.46 (m, 2H), 7.32-7.28 (m, 2H), 7.26-7.17 (m, 2H), 7.03-6.93 (m, 2H), 4.88 (s, 0.95H), 4.86 (s, 1.05H), 4.79 (s, 1.05H), 4.76 (s, 0.95H), 3.771 (s, 1.05H), 3.768 (s, 0.95H). LC-MS (ESI) m/z: 288.1 [M+H]⁺.

Example 65: Preparation of 1-(5,6-difluoro-1,3-dihydro-2H-isoindol-2-yl)-2-[(2-fluorophenyl)sulfanyl]ethanone (Compound 65)

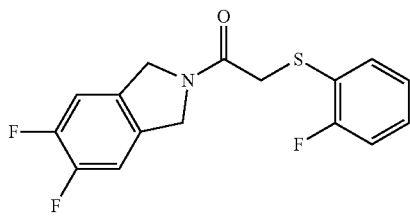 [SMILES: O=C(CSc1ccccc1F)N1Cc2cc(F)c(F)cc2C1]

Compound 65 was prepared in a manner similar to that described in Example 6.

¹H NMR (400 MHz, CDCl₃) δ 7.56 (ddd, 1H), 7.30-7.26 (m, 1H), 7.13-7.05 (m, 4H), 4.90 (s, 2H) 4.73 (s, 2H), 3.75 (s, 2H). LC-MS (ESI) m/z: 324.1 [M+H]⁺.

Example 66: Preparation of 1-(4-fluoro-1,3-dihydro-2H-isoindol-2-yl)-2-(phenylsulfanyl)ethanone (Compound 66)

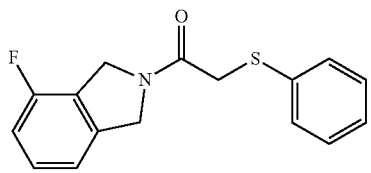 [SMILES: O=C(CSc1ccccc1)N1Cc2cccc(F)c2C1]

Compound 66 was prepared in a manner similar to that described in Example 1.

¹H NMR (400 MHz, CD₃OD, rotamers, about 1:1 ratio) δ 7.50-7.46 (m, 2H), 7.37-7.28 (m, 3H), 7.26-7.21 (m, 1H), 7.16-7.11 (m, 1H), 7.06-7.01 (m, 1H), 4.95 (s, 2H), 4.77 (s, 2H), 3.91 (s, 1H), 3.89 (s, 1H). LC-MS (ESI) m/z: 288.1 [M+H]⁺.

Example 67: Preparation of 2-[(2-chlorophenyl)sulfanyl]-1-(1,3-dihydro-2H-isoindol-2-yl)ethanone (Compound 67)

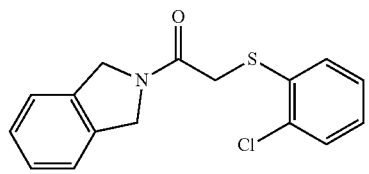

Compound 67 was prepared in a manner similar to that described in Example 1.

¹H NMR (400 MHz, CD₃OD) δ 7.53 (dd, 1H), 7.41 (dd, 1H), 7.35-7.19 (m, 6H), 5.01 (s, 2H), 4.75 (s, 2H), 3.98 (s, 2H). LC-MS (ESI) m/z: 304.1 [M+H]⁺.

Example 68: Preparation of 2-[(2,3-dichlorophenyl)sulfanyl]-1-(1,3-dihydro-2H-isoindol-2-yl)ethanone (Compound 68)

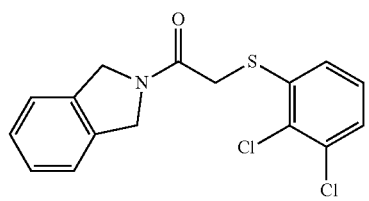 [SMILES: O=C(CSc1cccc(Cl)c1Cl)N1Cc2ccccc2C1]

Compound 68 was prepared in a manner similar to that described in Example 1.

¹H NMR (400 MHz, CDCl₃) δ 7.54 (dd, 1H), 7.34-7.27 (m, 5H), 7.19 (dd, 1H), 5.00-4.99 (m, 2H), 4.83 (s, 2H), 3.84 (s, 2H); LC-MS (ESI) m/z: 338.0 [M+H]⁺.

Example 69: Preparation of 1-(1,3-dihydro-2H-isoindol-2-yl)-2-[(4,5-dimethyl-1,3-thiazol-2-yl)sulfanyl]ethanone (Compound 69)

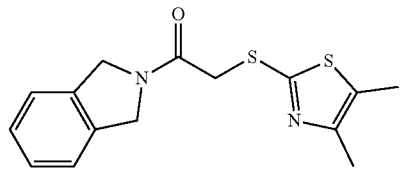 [SMILES: Cc1nc(SCC(=O)N2Cc3ccccc3C2)sc1C]

Compound 69 was prepared in a manner similar to that described in Example 1.

¹H NMR (400 MHz, CDCl₃) δ 7.31-7.26 (m, 4H), 4.99 (s, 2H), 4.84 (s, 2H), 4.09 (s, 2H), 2.28 (q, 3H), 2.24 (q, 3H). LC-MS (ESI) m/z: 305.1 [M+H]⁺.

Example 70: Preparation of 1-(1,3-dihydro-2H-isoindol-2-yl)-2-[(1-methyl-1H-pyrazol-3-yl)sulfanyl]ethanone (Compound 70)

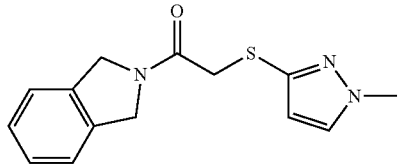 [SMILES: Cn1ccc(SCC(=O)N2Cc3ccccc3C2)n1]

Compound 70 was prepared in a manner similar to that described in Example 1.

$^1$H NMR (400 MHz, d6-Acetone) δ 7.55 (d, 1H), 7.38-7.30 (m, 4H), 6.28 (d, 1H), 4.98 (s, 2H), 4.70 (s, 2H), 3.91 (s, 2H), 3.81 (s, 3H). LC-MS (ESI) m/z: 274.1 [M+H]$^+$.

Example 71: Preparation of 1-(1,3-dihydro-2H-isoindol-2-yl)-2-[(3-fluoropyridin-2-yl)sulfanyl]ethanone (Compound 71)

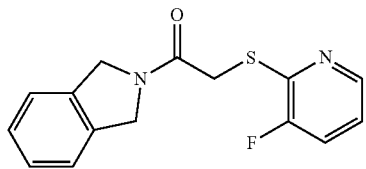 [SMILES: O=C(CSc1ncccc1F)N1Cc2ccccc2C1]

Compound 71 was prepared in a manner similar to that described in Example 1.

$^1$H NMR (400 MHz, CD$_3$OD) δ 8.21 (ddd, 1H), 7.44 (ddd, 1H), 7.38-7.31 (m, 4H), 7.14 (ddd, 1H), 5.15 (s, 2H), 4.77 (s, 2H), 4.24 (s, 2H). LC-MS (ESI) m/z: 289.1 [M+H]$^+$.

Example 72: Preparation of 1-(1,3-dihydro-2H-isoindol-2-yl)-2-(1,3-oxazol-2-ylsulfanyl)ethanone (Compound 72)

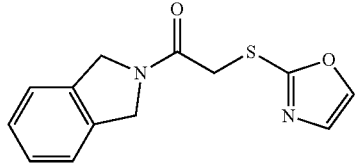 [SMILES: O=C(CSc1ncco1)N1Cc2ccccc2C1]

Compound 72 was prepared in a manner similar to that described in Example 1.

$^1$H NMR (400 MHz, CDCl$_3$) δ 7.67 (d, 1H), 7.33-7.26 (m, 4H), 7.09 (d, 1H), 5.00 (s, 2H), 4.86 (s, 2H), 4.21 (s, 2H). LC-MS (ESI) m/z: 261.1 [M+H]$^+$.

Example 73: Preparation of 1-(1,3-dihydro-2H-isoindol-2-yl)-2-[(6-fluoropyridin-2-yl)sulfanyl]ethanone (Compound 73)

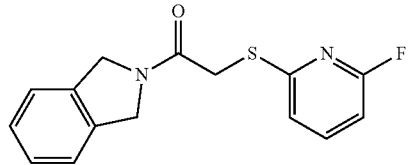 [SMILES: O=C(CSc1cccc(F)n1)N1Cc2ccccc2C1]

Step 1. S-[2-(1,3-Dihydro-2H-isoindol-2-yl)-2-oxo-ethyl] ethanethioate

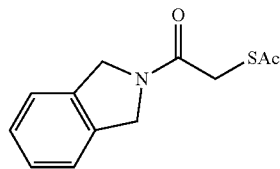

A mixture of 2-bromo-1-(1,3-dihydro-2H-isoindol-2-yl)ethanone (1502 mg, 6.26 mmol), potassium thioacetate (786 mg, 6.88 mmol) in N,N-dimethylformamide (50 mL) was stirred at room temperature for 16 h. The reaction was extracted with EtOAc and the organic layer was washed with brine, dried over MgSO$_4$, filtered, and concentrated in vacuo. The residue was used for next step without further purification.

Step 2. 1-(1,3-dihydro-2H-isoindol-2-yl)-2-[(6-fluoropyridin-2-yl)sulfanyl]ethanone A mixture of S-[2-(1,3-dihydro-2H-isoindol-2-yl)-2-oxoethyl] ethanethioate (118 mg, 0.5 mmol), 2-bromo-6-fluoropyridine (176 mg, 1 mmol), potassium phosphate (128 mg, 0.6 mmol), and 1,1'-bis(diphenylphosphino)ferrocene (19 mg, 0.04 mmol) in a mixed solvent (18 mL, toluene/acetone=2/1) was degassed with argon for 30 min. Bis(dibenzylideneacetone)palladium (14 mg, 0.03 mmol) was added and the resulting mixture was heated at 110° C. for 16 h. Water was added at room temperature and the mixture was extracted with EtOAc. The organic layer was dried over MgSO$_4$, filtered, and concentrated in vacuo. The residue was purified by column chromatography (EtOAc/Hexanes=1/20) to provide Compound 73 (128 mg, 89% in 2 steps) as a yellowish solid.

$^1$H NMR (400 MHz, CDCl$_3$) δ 7.59 (dd, 1H), 7.33-7.29 (m, 4H), 7.17 (ddd, 1H), 6.59 (ddd, 1H), 5.11-5.10 (m, 2H), 4.85 (s, 2H), 4.11 (s, 2H). LC-MS (ESI) m/z: 289.1 [M+H]$^+$.

Example 74: Preparation of 5-{[2-(1,3-dihydro-2H-isoindol-2-yl)-2-oxoethyl]sulfanyl}thiophene-2-carbonitrile (Compound 74)

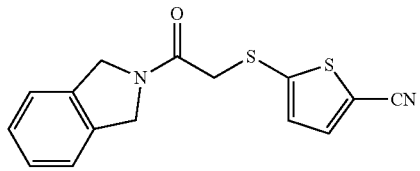 [SMILES: N#Cc1ccc(SCC(=O)N2Cc3ccccc3C2)s1]

Compound 74 was prepared in a manner similar to that described in Example 73.

$^1$H NMR (400 NMR, CDCl$_3$) δ 7.48 (d, 1H), 7.35-7.25 (m, 4H), 7.20 (d, 1H), 4.871-4.865 (m, 2H), 4.84 (s, 2H), 3.80 (s, 2H). LC-MS (ESI) m/z: 301.0 [M+H]$^+$.

Example 75: Preparation of 1-(1,3-dihydro-2H-isoindol-2-yl)-2-{[5-(hydroxymethyl)thiophen-2-yl]sulfanyl}ethanone (Compound 75)

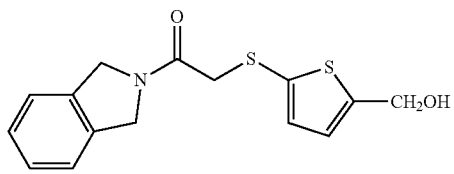 [SMILES: O=C(CSc1ccc(CO)s1)N1Cc2ccccc2C1]

Step 1. 5-{[2-(1,3-Dihydro-2H-isoindol-2-yl)-2-oxoethyl]sulfanyl}thiophene-2-carbaldehyde

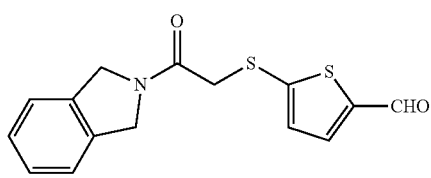 [SMILES: O=Cc1ccc(SCC(=O)N2Cc3ccccc3C2)s1]

5-{[2-(1,3-Dihydro-2H-isoindol-2-yl]-2-oxoethyl)sulfanyl}thiophene-2-carbaldehyde was prepared in a manner similar to that described in Example 73.

Step 2. 1-(1,3-dihydro-2H-isoindol-2-yl)-2-{[5-(hydroxymethyl)thiophen-2-yl]sulfanyl}ethanone Sodium borohydride (11 mg, 0.298 mmol) was added to a solution of 5-[(2-(1,3-dihydro-2H-isoindol-2-yl)-2-oxoethyl)sulfanyl]thiophene-2-carbaldehyde (30 mg, 0.0995 mmol) in anhydrous THF (5 mL) at 0° C. The reaction was stirred at room temperature for 1.5 h and then cooled to 0° C. A 2 N aqueous solution of hydrochloric acid was added and the resulting mixture was extracted with ethyl acetate. The organic layer was dried over MgSO$_4$, filtered, and concentrated in vacuo. The residue was purified by column chromatography (EtOAc/Hexanes=3/2) to provide Compound 75 (25 mg, 84%) as a yellow solid.

$^1$H NMR (400 NMR, CDCl$_3$) δ 7.34-7.23 (m, 4H), 7.10 (d, 1H), 6.85 (dt, 1H), 4.83-4.81 (m, 4H), 4.73 (d, 2H), 3.67 (s, 2H), 2.01 (t, 1H). LC-MS (ESI) m/z: 306.0 [M+H]$^+$.

Example 76: Preparation of 2-{[5-(difluoromethyl)thiophen-2-yl]sulfanyl}-1-(1,3-dihydro-2H-isoindol-2-yl)ethanone (Compound 76)

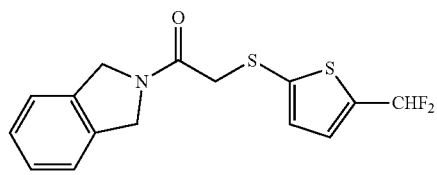 [SMILES: O=C(CSc1ccc(C(F)F)s1)N1Cc2ccccc2C1]

Compound 76 was prepared in a manner similar to that described in Example 73.

$^1$H NMR (400 NMR, CDCl$_3$) δ 7.32-7.24 (m, 4H), 7.18-7.13 (m, 2H), 6.73 (t, 1H), 4.83 (s, 4H), 3.74 (s, 2H). LC-MS (ESI) m/z: 326.1 [M+H]$^+$.

Example 77: Preparation of 1-[5-(morpholin-4-yl)-1,3-dihydro-2H-isoindol-2-yl]-2-(pyridin-2-ylsulfanyl)ethanone (Compound 77)

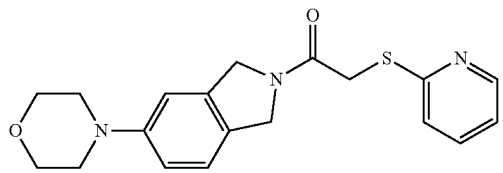 [SMILES: O=C(CSc1ccccn1)N1Cc2ccc(N3CCOCC3)cc2C1]

Step 1. 2-Bromo-1-[5-(morpholin-4-yl)-1,3-dihydro-2H-isoindol-2-yl]ethanone

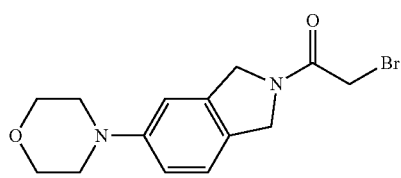 [SMILES: O=C(CBr)N1Cc2ccc(N3CCOCC3)cc2C1]

A 4 N solution of hydrochloric acid in 1,4-dioxane (3.5 mL) was added to a solution of 1,1-dimethylethyl 1,3-dihydro-5-(4-morpholinyl)-2H-isoindole-2-carboxylate (105 mg, 0.34 mmol) in dichloromethane (3.5 mL) at 0° C. After stirring at 0° C. for 4 h, the reaction mixture was poured into a cold saturated aqueous solution of sodium bicarbonate and then concentrates in vacuo. Methanol was added and the resulting mixture was filtered. The filtrate was concentrated to provide a crude residue of 2,3-dihydro-5-(4-morpholinyl)-1H-isoindole. The crude residue was then dissolved in dichloromethane (2 mL), and triethylamine (200 uL, 1.43 mmol) and bromoacetyl bromide (40 uL, 0.41 mmol) were sequentially added at 0° C. The reaction was warmed to room temperature and stirred for 3 h. Water was added and the resulting mixture was extracted with dichloromethane. The organic layer was dried over Na$_2$SO$_4$, filtered, and concentrated in vacuo. The residue was purified by column chromatography on CombiFlash® (EtOAc/CH$_2$Cl$_2$=1/4) to provide 2-bromo-1-[5-(morpholin-4-yl)-1,3-dihydro-2H-isoindol-2-yl]ethanone (51 mg, 45%).

Step 2. 1-[5-(morpholin-4-yl)-1,3-dihydro-2H-isoindol-2-yl]-2-(pyridin-2-ylsulfanyl)ethanone (Compound 77)

Using 2-bromo-1-[5-(morpholin-4-yl)-1,3-dihydro-2H-isoindol-2-yl]ethanone as an intermediate, Compound 77 was prepared in a manner similar to that described in Example 1, step 2.

$^1$H NMR (400 MHz, CDCl$_3$, rotamers, about 6:5 ratio) δ 8.39-8.36 (m, 1H), 7.52-7.47 (m, 1H), 7.30-7.26 (m, 1H), 7.18 (dd, 1H), 7.00-6.97 (m, 1H), 6.88 (ddd, 1H), 6.81 (dd, 1H), 5.01 (s, 0.91H), 4.98 (s, 1.09H), 4.79 (s, 1.09H), 4.76 (s, 0.91H), 4.14 (s, 2H), 3.89-3.86 (m, 4H), 3.16-3.13 (m, 4H). LC-MS (ESI) m/z: 356.1 [M+H]$^+$.

Example 78: Preparation of 3-[(2-chlorophenyl)sulfanyl]-1-(1,3-dihydro-2H-isoindol-2-yl)propan-1-one (Compound 78)

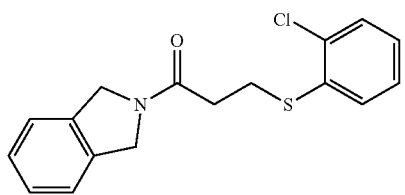 [SMILES: O=C(CCSc1ccccc1Cl)N1Cc2ccccc2C1]

Compound 78 was prepared in a manner similar to that described in Example 23.

$^1$H NMR (400 MHz, CDCl$_3$) δ 7.37 (ddd, 2H), 7.32-7.27 (m, 3H), 7.26-7.22 (m, 2H), 7.15-7.11 (m, 1H), 4.81 (s, 2H), 4.77 (s, 2H), 3.38-3.34 (m, 2H), 2.78-2.74 (m, 2H). LC-MS (ESI) m/z: 318.1 [M+H]$^+$.

Example 79: Preparation of 1-(1,3-dihydro-2H-isoindol-2-yl)-3-(phenylsulfanyl)propan-1-one (Compound 79)

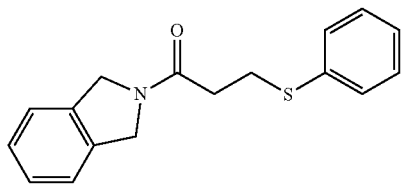 [SMILES: O=C(CCSc1ccccc1)N1Cc2ccccc2C1]

Compound 79 was prepared in a manner similar to that described in Example 23.

$^1$H NMR (400 MHz, CDCl$_3$) δ 7.40-7.36 (m, 2H), 7.32-7.27 (m, 6H), 7.23-7.17 (m, 1H), 4.79 (s, 2H), 4.73-4.72 (m, 2H), 3.35-3.31 (m, 2H), 2.73-2.69 (m, 2H). LC-MS (ESI) m/z: 284.1 [M+H]$^+$.

Example 80: Preparation of 2-[(5-chlorothiophen-2-yl)sulfinyl]-1-(1,3-dihydro-2H-isoindol-2-yl)ethanone (Compound 80)

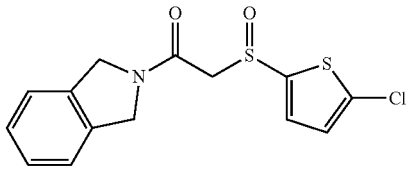 [SMILES: O=C(CS(=O)c1ccc(Cl)s1)N1Cc2ccccc2C1]

meta-Chloroperoxybenzoic acid (70% purity, 72 mg, 0.29 mmol) was added to a solution of 2-[(5-chlorothiophen-2-yl)sulfanyl]-1-(1,3-dihydro-2H-isoindol-2-yl)ethanone (90 mg, 0.29 mmol) in dichloromethane (20 mL) at 0° C. The mixture was stirred at room temperature for 3 h. The reaction was quenched with a saturated aqueous solution of sodium thiosulfate and a saturated aqueous solution of sodium bicarbonate. The mixture was then extracted with dichloromethane. The organic layer was dried over Na$_2$SO$_4$, filtered, and concentrated in vicuo. The residue was purified by column chromatography on CombiFlash© (EtOAc/Hexanes=1/1) to provide Compound 80 (58 mg, 61%) as a white solid.

$^1$H NMR (400 NMR, CDCl$_3$) δ 7.36 (d, 1H), 7.33-7.24 (m, 4H), 6.94 (d, 1H), 4.99-4.76 (m, 4H), 4.30 (d, 1H), 3.99 (d, 1H). LC-MS (ESI) m/z: 326.0 [M+H]$^+$.

Example 81: Preparation of 2-[(2-chlorophenyl)sulfinyl]-1-(1,3-dihydro-2H-isoindol-2-yl)ethanone (Compound 81)

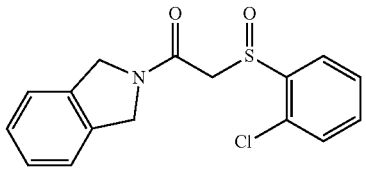 [SMILES: O=C(CS(=O)c1ccccc1Cl)N1Cc2ccccc2C1]

Compound 81 was prepared in a manner similar to that described in Example 28.

$^1$H NMR (400 NMR, CDCl$_3$) δ 7.99 (ddd, 1H), 7.59-7.54 (m, 1H), 7.51-7.47 (m, 1H), 7.45-7.42 (m, 1H), 7.34-7.21 (m, 4H), 5.02-4.82 (m, 4H), 4.17 (d, 1H), 3.83 (d, 1H). LC-MS (ESI) m/z: 320.0 [M+H]$^+$.

Example 82: Preparation of 1-(1,3-dihydro-2H-isoindol-2-yl)-2-[(6-fluoropyridin-2-yl)sulfinyl]ethanone (Compound 82)

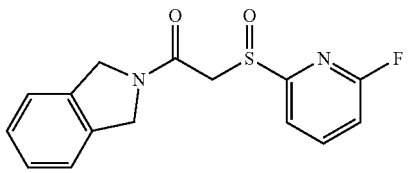 [SMILES: O=C(CS(=O)c1cccc(F)n1)N1Cc2ccccc2C1]

Compound 82 was prepared in a manner similar to that described in Example 80.

¹H NMR (400 MHz, CDCl₃) δ 8.06 (dd, 1H), 7.94 (ddd, 1H), 7.33-7.23 (m, 4H), 7.06 (ddd, 1H), 4.95 (s, 2H), 4.84 (s, 2H), 4.31 (d, 1H), 3.97 (d, 1H). LC-MS (ESI) m/z: 305.1 [M+H]⁺.

Example 83: Preparation of 3-[(2-chlorophenyl)sulfinyl]-1-(1,3-dihydro-2H-isoindol-2-yl)propan-1-one (Compound 83)

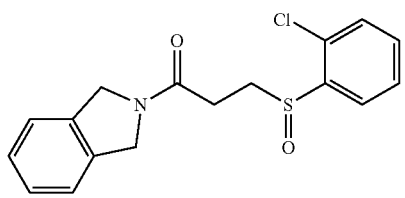 [SMILES: O=C(CCS(=O)c1ccccc1Cl)N1Cc2ccccc2C1]

Compound 83 was prepared in a manner similar to that described in Example 80.

¹H NMR (600 MHz, CDCl₃) δ 7.88 (dd, 1H), 7.50-7.47 (m, 1H), 7.46-7.41 (m, 2H), 7.32-7.26 (m, 4H), 4.86-4.67 (m, 4H), 3.59 (ddd, 1H), 3.24 (ddd, 1H), 2.93 (ddd, 1H), 2.69 (ddd, 1H). LC-MS (ESI) m/z: 334.0 [M+H]⁺.

Example 84: Preparation of 1-(1,3-dihydro-2H-isoindol-2-yl)-3-(phenylsulfinyl)propan-1-one (Compound 84)

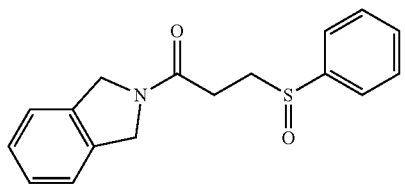

Compound 84 was prepared in a manner similar to that described in Example 80.

¹H NMR (400 MHz, CDCl₃) δ 7.68-7.65 (m, 2H), 7.55-7.47 (m, 3H), 7.32-7.27 (m, 4H), 4.87-4.70 (m, 4H), 3.40 (ddd, 1H), 3.07 (ddd, 1H), 3.00-2.92 (m, 1H), 2.66 (ddd, 1H). LC-MS (ESI) m/z: 300.1 [M+H]⁺.

Example 85: Preparation of 1-(5-hydroxy-1,3-dihydro-2H-isoindol-2-yl)-2-(pyridin-2-ylsulfonyl)ethanone (Compound 85)

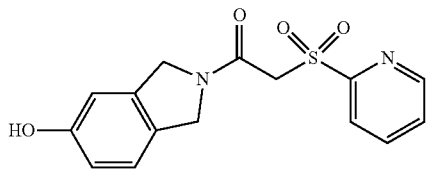 [SMILES: O=C(CS(=O)(=O)c1ccccn1)N1Cc2ccc(O)cc2C1]

Compound 85 was prepared in a manner similar to that described in Example 28.

¹H NMR (400 MHz, d6-DMSO, rotamers, about 1:1 ratio) δ 9.48 (s, 1H), 8.78 (dd, 1H), 8.16 (ddd, 1H), 8.05 (d, 1H), 7.77-7.73 (m, 1H), 7.12-7.09 (m, 1H), 6.71-6.69 (m, 2H), 4.90 (s, 1H), 4.86 (s, 1H), 4.81 (s, 2H), 4.48 (s, 1H), 4.44 (s, 1H). LC-MS (ESI) m/z: 319.0 [M+H]⁺.

Example 86: Preparation of 1-(1,3-dihydro-2H-isoindol-2-yl)-2-[(3-fluorophenyl)sulfonyl]ethanone (Compound 86)

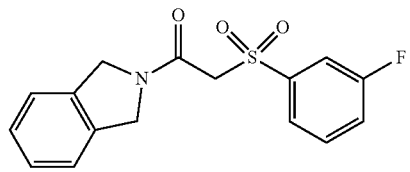 [SMILES: O=C(CS(=O)(=O)c1cccc(F)c1)N1Cc2ccccc2C1]

Compound 86 was prepared in a manner similar to that described in Example 28.

¹H NMR (400 MHz, CDCl₃) δ 7.77 (d, 1H), 7.69-7.66 (m, 1H), 7.61-7.55 (m, 1H), 7.41-7.37 (m, 1H), 7.35-7.26 (m, 4H), 5.09 (s, 2H), 4.80 (s, 2H), 4.28 (s, 2H). LC-MS (ESI) m/z: 320.2 [M+H]⁺.

Example 87: Preparation of 1-(1,3-dihydro-2H-isoindol-2-yl)-2-[(4-fluorophenyl)sulfonyl]ethanone (Compound 87)

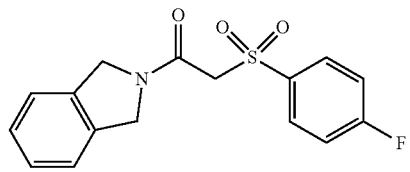 [SMILES: O=C(CS(=O)(=O)c1ccc(F)cc1)N1Cc2ccccc2C1]

Compound 87 was prepared in a manner similar to that described in Example 28.

¹H NMR (400 MHz, CDCl₃) δ 7.99-7.96 (m, 2H), 7.34-7.23 (m, 6H), 5.09 (s, 2H), 4.79 (s, 2H), 4.27 (s, 2H). LC-MS (ESI) m/z: 320.1 [M+H]⁺.

Example 88: Preparation of 2-[(5-chlorothiophen-2-yl)sulfonyl]-1-(1,3-dihydro-2H-isoindol-2-yl)ethanone (Compound 88)

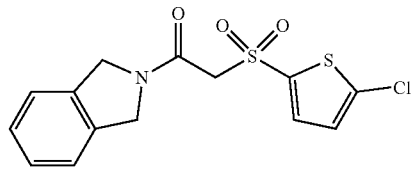 [SMILES: O=C(CS(=O)(=O)c1ccc(Cl)s1)N1Cc2ccccc2C1]

Compound 88 was prepared in a manner similar to that described in Example 28.

¹H NMR (400 NMR, CDCl₃) δ 7.58 (d, 1H), 7.33-7.26 (m, 4H), 7.01 (d, 1H), 5.06 (s, 2H), 4.83 (s, 2H), 4.34 (s, 2H). LC-MS (ESI) m/z: 342.0 [M+H]⁺.

Example 89: Preparation of 2-[(2,5-difluorophenyl)sulfonyl]-1-(1,3-dihydro-2H-isoindol-2-yl)ethanone (Compound 89)

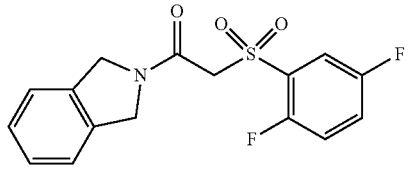 [SMILES: O=C(CS(=O)(=O)c1cc(F)ccc1F)N1Cc2ccccc2C1]

Compound 89 was prepared in a manner similar to that described in Example 28.

$^1$H NMR (400 MHz, CDCl$_3$) δ 7.62 (ddd, 1H), 7.40-7.24 (m, 6H), 5.10 (s, 2H), 4.77 (s, 2H), 4.46 (s, 2H). LC-MS (ESI) m/z: 338.1 [M+H]$^+$.

Example 90: Preparation of 1-(1,3-dihydro-2H-isoindol-2-yl)-2-[(2-fluorophenyl)sulfonyl]ethanone (Compound 90)

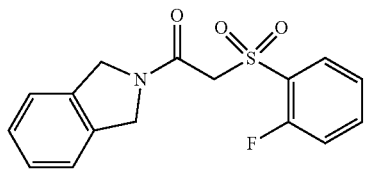 [SMILES: O=C(CS(=O)(=O)c1ccccc1F)N1Cc2ccccc2C1]

Compound 90 was prepared in a manner similar to that described in Example 28.

$^1$H NMR (400 MHz, CDCl$_3$) δ 7.92 (ddd, 1H), 7.72-7.66 (m, 1H), 7.37-7.26 (m, 6H), 5.12 (s, 2H), 4.76 (s, 2H), 4.45 (s, 2H). LC-MS (ESI) m/z: 320.1 [M+H]$^+$.

Example 91: Preparation of 2-[(2,4-difluorophenyl)sulfonyl]-1-(1,3-dihydro-2H-isoindol-2-yl)ethanone (Compound 91)

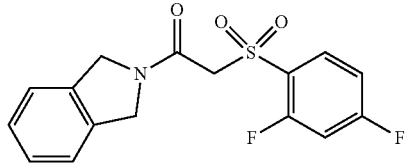 [SMILES: O=C(CS(=O)(=O)c1ccc(F)cc1F)N1Cc2ccccc2C1]

Compound 91 was prepared in a manner similar to that described in Example 28.

$^1$H NMR (400 MHz, CDCl$_3$) δ 7.96-7.90 (m, 1H), 7.34-7.26 (m, 4H), 7.09-6.99 (m, 2H), 5.11 (s, 2H), 4.76 (s, 2H), 4.42 (s, 2H). LC-MS (ESI) m/z: 338.1 [M+H]$^+$.

Example 92: Preparation of 1-(5-fluoro-1,3-dihydro-2H-isoindol-2-yl)-2-[(2-fluorophenyl)sulfonyl]ethanone (Compound 92)

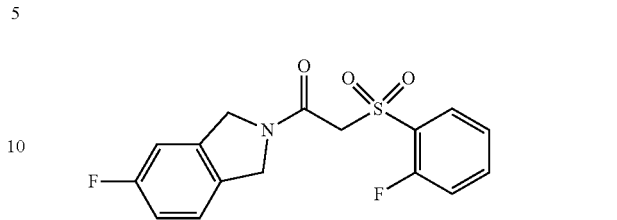

Compound 92 was prepared in a manner similar to that described in Example 28.

$^1$H NMR (400 MHz, CDCl$_3$, rotamers, about 1:1 ratio) δ 7.94-7.90 (m, 1H), 7.71-7.67 (m, 1H), 7.37-7.21 (m, 3H), 7.05-6.97 (m, 2H), 5.11 (s, 1H), 5.08 (s, 1H), 4.75 (s, 1H), 4.72 (s, 1H), 4.43 (s, 2H). LC-MS (ESI) m/z: 338.0 [M+H]$^+$.

Example 93: Preparation of 1-(5-fluoro-1,3-dihydro-2H-isoindol-2-yl)-2-(phenylsulfonyl)ethanone (Compound 93)

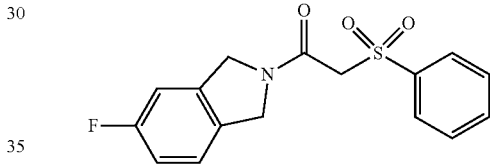

Compound 93 was prepared in a manner similar to that described in Example 28.

$^1$H NMR (400 MHz, CDCl$_3$, rotamers, about 1:1 ratio) δ 7.98-7.95 (m, 2H), 7.72-7.67 (m, 1H), 7.61-7.57 (m, 2H), 7.26-7.21 (m, 1H), 7.05-6.97 (m, 2H), 5.08 (s, 1H), 5.05 (s, 1H), 4.78 (s, 1H), 4.75 (s, 1H), 4.26 (s, 1H), 4.25 (s, 1H). LC-MS (ESI) m/z: 320.1 [M+H]$^+$.

Example 94: Preparation of 1-(1,3-dihydro-2H-isoindol-2-yl)-2-[(4-methyl-1,3-thiazol-2-yl)sulfonyl]ethanone (Compound 94)

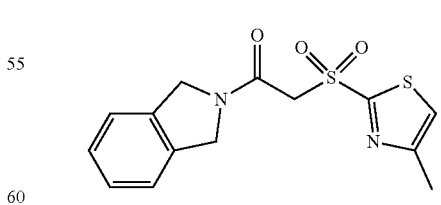

Compound 94 was prepared in a manner similar to that described in Example 28.

$^1$H NMR (400 NMR, CDCl$_3$) δ 7.34 (q, 1H), 7.33-7.26 (m, 4H), 5.07 (s, 2H), 4.79 (s, 2H), 4.56 (s, 2H), 2.56 (d, 3H). LC-MS (ESI) m/z: 323.0 [M+H]$^+$.

Example 95: Preparation of 1-(5,6-difluoro-1,3-dihydro-2H-isoindol-2-yl)-2-[(2-fluorophenyl)sulfonyl]ethanone (Compound 95)

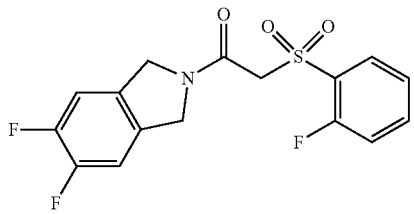 [SMILES: O=C(CS(=O)(=O)c1ccccc1F)N1Cc2cc(F)c(F)cc2C1]

Compound 95 was prepared in a manner similar to that described in Example 28.

$^1$H NMR (400 MHz, CDCl$_3$) δ 7.93-7.90 (m, 1H), 7.73-7.67 (m, 1H), 7.37-7.29 (m, 2H), 7.12-7.07 (m, 2H), 5.08 (s, 2H) 4.72 (s, 2H), 4.41 (s, 2H). LC-MS (ESI) m/z: 356.1 [M+H]$^+$.

Example 96: Preparation of 1-(4-fluoro-1,3-dihydro-2H-isoindol-2-yl)-2-(phenylsulfonyl)ethanone (Compound 96)

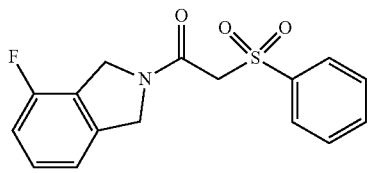 [SMILES: O=C(CS(=O)(=O)c1ccccc1)N1Cc2cccc(F)c2C1]

Compound 96 was prepared in a manner similar to that described in Example 28.

$^1$H NMR (400 MHz, d6-DMSO, rotamers, about 1:1 ratio) δ 7.97-7.94 (m, 2H), 7.77-7.72 (m, 1H), 7.67-7.63 (m, 2H), 7.40-7.35 (m, 1H), 7.21-7.12 (m, 2H), 4.99 (s, 2H), 4.74 (s, 1H), 4.70 (s, 1H), 4.66 (s, 2H). LC-MS (ESI) m/z: 320.1 [M+H]$^+$.

Example 97: Preparation of 1-(1,3-dihydro-2H-isoindol-2-yl)-2-[(6-fluoropyridin-2-yl)sulfonyl]ethanone (Compound 97)

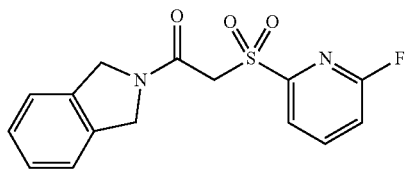 [SMILES: O=C(CS(=O)(=O)c1cccc(F)n1)N1Cc2ccccc2C1]

Compound 97 was prepared in a manner similar to that described in Example 28.

$^1$H NMR (400 MHz, CDCl$_3$) δ 8.12-8.07 (m, 1H), 8.02 (ddd, 1H), 7.34-7.27 (m, 4H), 7.23 (ddd, 1H), 5.06 (s, 2H), 4.76 (s, 2H), 4.58 (s, 2H). LC-MS (ESI) m/z: 321.1 [M+H]$^+$.

Example 98: Preparation of 2-[(2,3-dichlorophenyl)sulfonyl]-1-(1,3-dihydro-2H-isoindol-2-yl)ethanone (Compound 98)

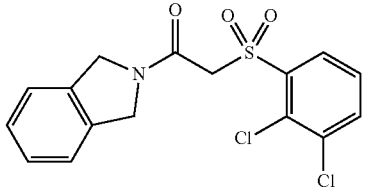 [SMILES: O=C(CS(=O)(=O)c1cccc(Cl)c1Cl)N1Cc2ccccc2C1]

Compound 98 was prepared in a manner similar to that described in Example 28.

$^1$H NMR (400 MHz, CDCl$_3$) δ 8.05 (dd, 1H), 7.77 (dd, 1H), 7.43 (dd, 1H), 7.34-7.27 (m, 4H), 5.10 (s, 2H), 4.75 (s, 2H), 4.60 (s, 2H). LC-MS (ESI) m/z: 370.0 [M+H]$^+$.

Example 99: Preparation of 2-[(2-chlorophenyl)sulfonyl]-1-(1,3-dihydro-2H-isoindol-2-yl)ethanone (Compound 99)

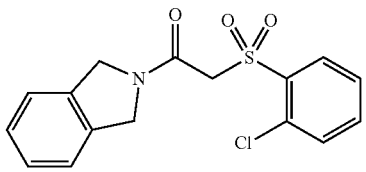 [SMILES: O=C(CS(=O)(=O)c1ccccc1Cl)N1Cc2ccccc2C1]

meta-Chloroperoxybenzoic acid (42 mg, 0.51 mmol) was added to a solution of 2-[(2-chlorophenyl)sulfinyl]-1-(1,3-dihydro-2H-isoindol-2-yl)ethanone (29 mg, 0.09 mmol) in dichloromethane (2.9 mL) at 0° C. The mixture was stirred at room temperature for 16 h. The reaction was quenched with a saturated aqueous solution of sodium thiosulfate and a saturated aqueous solution of sodium bicarbonate. The mixture was then extracted with dichloromethane. The organic layer was dried over Na$_2$SO$_4$, filtered, and concentrated in vicuo. The residue was purified by column chromatography (EtOAc/CH$_2$Cl$_2$=1/1) to provide Compound 99 (20 mg, 64%) as a white solid.

$^1$H NMR (400 MHz, CDCl$_3$) δ 8.13-8.10 (m, 1H), 7.62-7.58 (m, 2H), 7.50-7.46 (m, 1H), 7.33-7.26 (m, 4H), 5.11 (s, 2H), 4.76 (s, 2H), 4.57 (s, 2H). LC-MS (ESI) m/z: 336.0 [M+H]$^+$.

Example 100: Preparation of 1-[5-(morpholin-4-yl)-1,3-dihydro-2H-isoindol-2-yl]-2-(pyridin-2-ylsulfonyl)ethanone (Compound 100)

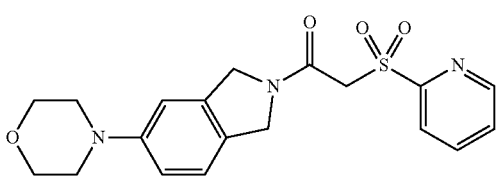 [SMILES: O=C(CS(=O)(=O)c1ccccn1)N1Cc2ccc(N3CCOCC3)cc2C1]

Compound 100 was prepared in a manner similar to that described in Example 28.

¹H NMR (400 MHz, CDCl₃, rotamers, about 6:5 ratio) δ 8.77-8.75 (m, 1H), 8.12-8.09 (m, 1H), 7.98 (ddd, 1H), 7.59-7.56 (m, 1H), 7.15 (dd, 1H), 6.87 (ddd, 1H), 6.78 (dd, 1H), 5.01 (s, 0.91H), 4.97 (s, 1.09H), 4.68 (s, 1.09H), 4.65 (s, 0.91H), 4.60 (s, 2H), 3.88-3.84 (m, 4H), 3.15-3.12 (m, 4H). LC-MS (ESI) m/z: 388.2 [M+H]⁺.

Example 101: Preparation of 1-(1,3-dihydro-2H-isoindol-2-yl)-2-[(5-fluoropyridin-2-yl)sulfonyl]ethanone (Compound 101)

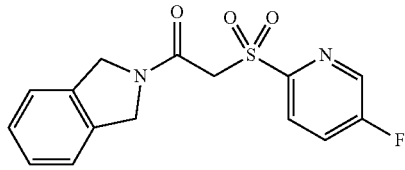 [SMILES: O=C(CS(=O)(=O)c1ccc(F)cn1)N1Cc2ccccc2C1]

Compound 101 was prepared in a manner similar to that described in Example 28.

¹H NMR (400 MHz, CDCl₃) δ 8.61 (d, 1H), 8.16 (dd, 1H), 7.66 (ddd, 1H), 7.34-7.26 (m, 4H), 5.07 (s, 2H), 4.75 (s, 2H), 4.57 (s, 2H). LC-MS (ESI) m/z: 321.1 [M+H]⁺.

Example 102: Preparation of 1-(1,3-dihydro-2H-isoindol-2-yl)-2-[(1-methyl-1H-pyrazol-3-yl)sulfonyl]ethanone (Compound 102)

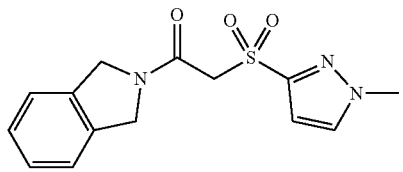 [SMILES: Cn1ccc(S(=O)(=O)CC(=O)N2Cc3ccccc3C2)n1]

Compound 102 was prepared in a manner similar to that described in Example 28.

¹H NMR (400 MHz, CDCl₃) δ 7.47 (d, 1H), 7.33-7.26 (m, 4H), 6.84 (d, 1H), 5.10 (s, 2H), 4.81 (s, 2H), 4.39 (s, 2H), 4.01 (s, 3H). LC-MS (ESI) m/z: 306.1 [M+H]⁺.

Example 103: Preparation of 1-(1,3-dihydro-2H-isoindol-2-yl)-2-[(3-fluoropyridin-2-yl)sulfonyl]ethanone (Compound 103)

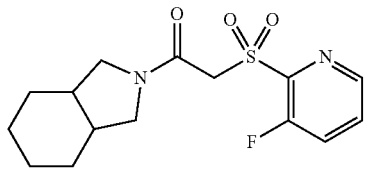 [SMILES: O=C(CS(=O)(=O)c1ncccc1F)N1CC2CCCCC2C1]

Compound 103 was prepared in a manner similar to that described in Example 28.

¹H NMR (400 MHz, CDCl₃) δ 8.58-8.56 (m, 1H), 7.71-7.62 (m, 2H), 7.33-7.26 (m, 4H), 5.11 (s, 2H), 4.76 (s, 2H), 4.58 (s, 2H). LC-MS (ESI) m/z: 321.1 [M+H]⁺.

Example 104: Preparation of 1-(1,3-dihydro-2H-isoindol-2-yl)-2-(1,3-oxazol-2-ylsulfonyl)ethanone (Compound 104)

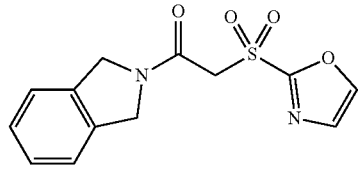

Compound 104 was prepared in a manner similar to that described in Example 28.

¹H NMR (400 MHz, CDCl₃) δ 7.92 (d, 1H), 7.44 (d, 1H), 7.34-7.26 (m, 4H), 5.06 (s, 2H), 4.79 (s, 2H), 4.54 (s, 2H). LC-MS (ESI) m/z: 293.1 [M+H]⁺.

Example 105: Preparation of 2-{[5-(difluoromethyl)thiophen-2-yl]sulfonyl}-1-(1,3-dihydro-2H-isoindol-2-yl)ethanone (Compound 105)

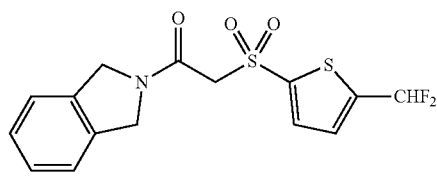 [SMILES: O=C(CS(=O)(=O)c1ccc(C(F)F)s1)N1Cc2ccccc2C1]

Compound 105 was prepared in a manner similar to that described in Example 28.

¹H NMR (400 NMR, CDCl₃) δ 7.74 (dt, 1H), 7.36-7.26 (m, 5H), 6.86 (td, 1H), 5.07 (s, 2H), 4.83 (s, 2H), 4.37 (s, 2H). LC-MS (ESI) m/z: 358.1 [M+H]⁺.

Example 106: Preparation of 3-[(2-chlorophenyl)sulfonyl]-1-(1,3-dihydro-2H-isoindol-2-yl)propan-1-one (Compound 106)

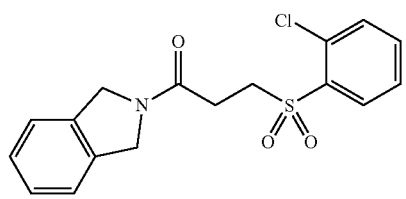 [SMILES: O=C(CCS(=O)(=O)c1ccccc1Cl)N1Cc2ccccc2C1]

Compound 106 was prepared in a manner similar to that described in Example 28.

¹H NMR (400 MHz, CDCl₃) δ 8.14-8.12 (m, 1H), 7.59-7.57 (m, 2H), 7.48-7.43 (m, 1H), 7.33-7.27 (m, 4H), 4.83 (s, 2H), 4.73 (s, 2H), 3.88-3.84 (m, 2H), 2.95-2.91 (m, 2H). LC-MS (ESI) m/z: 350.1 [M+H]⁺.

Example 107: Preparation of 1-(1,3-dihydro-2H-isoindol-2-yl)-3-(phenylsulfonyl)propan-1-one (Compound 107)

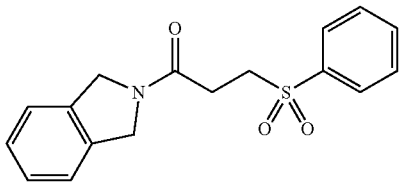 [SMILES: O=C(CCS(=O)(=O)c1ccccc1)N1Cc2ccccc2C1]

Compound 107 was prepared in a manner similar to that described in Example 28.

$^1$H NMR (400 MHz, CDCl$_3$) δ 7.97-7.94 (m, 2H), 7.69-7.65 (m, 1H), 7.60-7.56 (m, 2H), 7.33-7.27 (m, 4H), 4.83 (s, 2H), 4.73 (s, 2H), 3.58-3.54 (m, 2H), 2.91-2.87 (m, 2H). LC-MS (ESI) m/z: 316.1 [M+H]$^+$.

Example 108: Preparation of 1-(1,3-dihydro-2H-isoindol-2-yl)-3-[(6-fluoropyridin-2-yl)sulfonyl]propan-1-one (Compound 108)

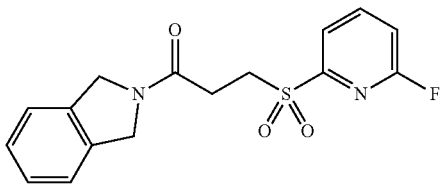 [SMILES: O=C(CCS(=O)(=O)c1cccc(F)n1)N1Cc2ccccc2C1]

Compound 108 was prepared in a manner similar to that described in Example 28.

$^1$H NMR (400 MHz, CDCl$_3$) δ 8.12-8.06 (m, 1H), 8.03-8.00 (m, 1H), 7.33-7.28 (m, 4H), 7.23 (ddd, 1H), 4.87 (s, 2H), 4.77 (s, 2H), 3.84-3.80 (m, 2H), 3.04-3.00 (m, 2H). LC-MS (ESI) m/z: 335.0 [M+H]$^+$.

Example 109: Preparation of 1-(5-fluoro-1,3-dihydro-2H-isoindol-2-yl)-2-(1,3-oxazol-2-ylsulfonyl)ethanone (Compound 109)

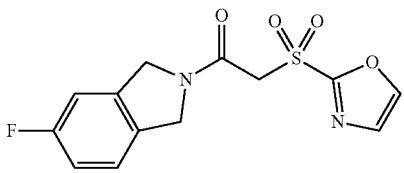 [SMILES: O=C(CS(=O)(=O)c1ncco1)N1Cc2ccc(F)cc2C1]

Compound 109 was prepared in a manner similar to that described in Example 28.

$^1$H NMR (400 MHz, CDCl$_3$, rotamers, about 1.1:1 ratio) δ7.923-7.921 (m, 1H), 7.44 (d, 1H), 7.25-7.22 (m, 1H), 7.06-6.98 (m, 2H), 5.05 (s, 0.95H), 5.02 (s, 1.05H), 4.77 (s, 1.05H), 4.75 (s, 0.95H), 4.52 (s, 1H). LC-MS (ESI) m/z: 311.0 [M+1]$^+$

Example 110: Evaluation of Cisd2 Activator

Compounds 1-109 were tested for increasing the level of Cisd2 in human embryonic kidney cells 293 (HEK293), a transfected cell line expressing Cisd2, using the Cisd2-luciferase reporter assay as follows.

The transfected HEK293 cells stably expressed Cisd2 promoter with firefly luciferase reporter (HEK293-CISD2). They were kept in Dulbecco's modified Eagle's medium (DMEM) (Gibco, New York, NY, USA). Culture medium was supplemented with 10% heat-inactivated fetal bovine serum (FBS), 2 mM L-Glutamine, 1 mM sodium pyruvate, 0.1% MEM Non-Essential Amino Acids, 1 ug/ml puromycin and 1% penicillin/streptomycin (HyClone, Logan, UT, USA). The cells were maintained at 37° C. in an incubator (Thermo Fisher Scientific, New York, NY, USA) with an atmosphere of 5% CO$_2$. The stably transfected cells were seeded in 384-well plates at a density of 3×10$^3$ cells/well. After incubation with tested compounds at 37° C. for 24 hours, ONE-Glo™ Luciferase Assay System (Promega, Madison, WI, USA) was added at room temperature for 5 minutes to detect any luciferase activity. Luminescence intensity was registered using plate reader Victor$^2$V (PerkinElmer, Boston, MA, USA).

Each of Compounds 1-109 was found to activate Cisd2 to a degree indicated by its EC$_{50}$ value. See Table 2 below. EC$_{50}$ values in this table are presented in three classes, i.e., A: <1 μM, B: 1 μM-5 μM, and C: 5 μM-10 μM.

TABLE 2

| Compound No. | EC$_{50}$ | Compound No. | EC$_{50}$ |
|---|---|---|---|
| 1 | A | 2 | A |
| 3 | B | 4 | A |
| 5 | A | 6 | B |
| 7 | A | 8 | B |
| 9 | A | 10 | B |
| 11 | A | 12 | A |
| 13 | A | 14 | A |
| 15 | B | 16 | A |
| 17 | B | 18 | B |
| 19 | B | 20 | B |
| 21 | C | 22 | C |
| 23 | A | 24 | A |
| 25 | B | 26 | A |
| 27 | B | 28 | A |
| 29 | A | 30 | A |
| 31 | A | 32 | A |
| 33 | A | 34 | A |
| 35 | A | 36 | B |
| 37 | C | 38 | A |
| 39 | A | 40 | A |
| 41 | B | 42 | B |
| 43 | B | 44 | C |
| 45 | A | 46 | A |
| 47 | C | 48 | A |
| 49 | B | 50 | A |
| 51 | A | 52 | A |
| 53 | A | 54 | A |
| 55 | C | 56 | A |
| 57 | A | 58 | A |
| 59 | A | 60 | A |
| 61 | A | 62 | C |
| 63 | A | 64 | A |
| 65 | A | 66 | A |
| 67 | A | 68 | B |
| 69 | B | 70 | B |
| 71 | A | 72 | A |
| 73 | B | 74 | A |
| 75 | A | 76 | B |
| 77 | C | 78 | A |
| 79 | A | 80 | B |
| 81 | A | 82 | A |
| 83 | A | 84 | A |
| 85 | A | 86 | A |
| 87 | A | 88 | A |
| 89 | C | 90 | A |
| 91 | A | 92 | A |
| 93 | A | 94 | A |

TABLE 2-continued

| Compound No. | EC$_{50}$ | Compound No. | EC$_{50}$ |
|---|---|---|---|
| 95 | A | 96 | A |
| 97 | A | 98 | A |
| 99 | A | 100 | B |
| 101 | A | 102 | B |
| 103 | A | 104 | A |
| 105 | C | 106 | A |
| 107 | A | 108 | B |
| 109 | A | | |

Example 111: In Vivo Study for Treating Anti-Nonalcoholic Fatty Liver Disease

Compound 28 of this invention was evaluated for its anti-nonalcoholic fatty liver disease (NAFLD) effect and in vivo toxicity following an assay described below.

Cisd2 floxed allele (Cisd2 f/f) mice were prepared following a procedure described in Wang et al., *Hum. Mol. Genet.* 23, 4770-85(2014). To obtain Cisd2 heterozygous hepatocyte-specific knockout (Cisd2 hKO-het, Cisd2 f/+; Alb-Cre Tg), Cisd2 f/f mice were bred with Albumin-Cre transgenic (Alb-Cre Tg, JAX003574) mice. After one generation, Cisd2 hKO-het mice were obtained. Male mice were chosen to be used in this study. All mice have a pure or congenic C57BL/6 background and were bred/housed in a specific pathogen-free facility with a 12 h light/12 h dark cycle at a temperature of 20-22° C. Groups of mice at 8 weeks old were provided a diet (AIN93G, TestDiet) containing a vehicle (0.14 wt % of DMF and 0.15 wt % of Cremophor® EL) or compound 28 (0.015 wt %) for 4 weeks.

Histopathology was used to evaluate the efficacy of Compound 28 in ameliorating NAFLD. Liver tissues were collected and fixed with 10% formalin at 4° C. overnight. They were then processed in a tissue processor (STP120, MICROM), followed by embedding in paraffin. H&E of tissue sections (3-4 m) were carried out by a standard protocol. Specifically, the liver tissue sections were deparaffinized, rehydrated, and stained by Mayer's hematoxylin (MUTO Pure Chemicals, 3000-2) and 1% eosin Y solution (MUTO Pure Chemicals, 3200-2). The stained liver tissue sections were then dehydrated, mounted with a mounting medium (Surgipath, 75810-346), and coverslipped.

Serum Biochemical analysis was performed to evaluate in vivo toxicity of Compound 28. Whole blood samples were collected from facial vein or cardiac puncture at sacrifice for analyzing serum alanine aminotransferase (GPT/ALT), aspartate aminotransferase (GOT/AST), blood urea nitrogen (BUN) and creatinine (CRE) were on Fuji Dri-Chem 4000i (FUJIFILM).

Unexpectedly, Compound 28 ameliorated NAFLD in Cisd2 hKO-het mice without observed toxicity.

Example 112: In Vivo Study of Treating Nonalcoholic Steatohepatitis

Compound 28 was used to alleviate nonalcoholic steatohepatitis (NASH) in Cisd2 hKO male mice described above.

Cisd2 hKO were bred for two generations. All male mice used in this study had a pure or congenic C57BL/6 background and were bred/housed in a specific pathogen-free facility with a 12 h light/12 h dark cycle at a temperature of 20-22° C. They were fed 30% (w/v) fructose (Alfa Aesar A17718) in water to establish a fructose-induced NASH model. Groups of mice at 2 months old were provided with a diet (AIN93G, TestDiet) containing a vehicle (0.14 wt % of DMF and 0.15 wt % of Cremophor® EL) or Compound 28 (0.015 wt %) for 5 months. The food and drinking water were provided ad libitum.

Histopathology was used to evaluate the efficacy of Compound 28 in alleviating NASH. Liver tissues were processed and stained as described in Example 53 above.

An oral glucose tolerance test (GTT) and an insulin tolerance test (ITT) were performed to study beneficial effects of Compound 28 in the fructose-induced NASH model. In the oral glucose tolerance test, mice were fasted for 14 hours (7 p.m. to 9 a.m.) and then were orally administrated with glucose water (1.5 mg/g body weight) using a feeding needle. Blood samples were collected from tail vein before (0 min) and after glucose treatment at predetermined time points. Blood glucose levels were measured using OneTouch® Ultra glucose test strips and SureStep® Meter (LifeScan). In the insulin tolerance test, mice were fasted for 2 hours (9 a.m. to 11 a.m.) and then intraperitoneally injected with insulin (0.75 U/kg body weight) (Actrapid® human regular insulin, Novo Nordisk). Blood samples were collected and monitored at predetermined time points.

Unexpectedly, Compound 28 was found to ameliorate fructose-induced NASH and alleviate fructose-induced glucose intolerance and insulin resistance in mice without obvious toxicity.

Example 113: In Vivo Study of Protecting Against Doxorubicin-Induced Cardiotoxicity Compound 28 was evaluated for protecting against doxorubicin-induced cardiotoxicity in mice.

Male C57BL/6 mice between 7 and 8 months old were treated with Compound 28 (at a dosage of 1 mg/kg) or a vehicle (1.5 wt % of DMF and 3 wt % of Cremophor® EL in PBS) via intraperitoneal injection (i.p.) twice a day for 2 days. At day 0, 1 hour after the treatment with Compound 28, doxorubicin (25 mg/kg, i.p.) or another vehicle (10% DMSO in normal saline) was injected into mice.

Electrocardiogram (ECG) and heart echo on day 4 and day 5 respectively were used as indications of cardiac function. Mice tissues were collected on day 5 and were fixed with 10% formalin at 4° C. overnight, followed by paraffin embedding and sectioning.

Functional test of heart using ECG was performed as described in Yeh et al., *PLoS Biol.* 2019, 17, e3000508. The mice were maintained on a 12:12 hour dark-light cycle with lights switched on at 6:00 am. All procedures took place during the light phase. Anesthesia was initially induced by placing the mice for 3-5 minutes in a chamber filled with 3 v/v % isoflurane (Aesica Pharmaceuticals, Hertfordshire, UK). The mice were then positioned on a warm pad (ALA Scientific Instruments, Inc. NY) that enabled maintaining temperature during ECG recording. Mice breathed freely through a nose cone. Anesthesia was maintained by inhalation of 1.5% isoflurane. Continuous 5-minute ECGs were obtained using subcutaneous electrodes attached at the four limbs and recorded with PowerLab® data acquisition system (model ML866, ADInstruments, Colorado Springs, CO) and Animal Bio Amp® (model ML136, ADInstruments). ECG analysis was performed in an unbiased fashion where 1500 beats were analyzed using LabChart® 7 Pro version 7.3.1 (ADInstruments, Inc). Detection and analysis of QTc interval, QRS intervals, Tpeak-T end intervals were set to Mouse ECG parameters. The values thus obtained were compared statistically by utilizing the Mann-Whitney U test, and p<0.05 was accepted as significant.

Transthoracic mouse echocardiography was used to provide noninvasive imaging of the heart on a VisualSonics® VeVo® 2100 imaging system (VisualSonics, Toronto, Ontario, Canada). Male mice were anesthetized with 1% isoflurane in 95% $O_{2(g)}$. Body temperature was maintained and monitored at 36° C. to 37° C. on a heated pad (TC-1000, CWE Inc. USA). ECGs were continuously monitored. Cardiac function was assessed using a high-frequency 30-50 MHz probe, as described in Casaclang-Verzosa et al., *J. Vis. Exp.* 120, e54110 (2017). Data analysis was performed using VisualSonics® software. Personnel responsible for data acquisition were blinded to the animal grouping.

The results showed unexpectedly that compound 28 protected against doxorubicin-induced cardiotoxicity.

Example 114: In Vivo Study of Treating Doxorubicin-Induced Cachexia and Hepatotoxicity Compound 28 was used in rescuing doxorubicin-induced cachexia and hepatotoxicity in the following in vivo study.

Male C57BL/6 mice between 7 and 8 months were pretreated with Compound 28 (1 mg/kg) or a vehicle (1.5 wt % of DMF and 3 wt % of Cremophor® EL in PBS) via intraperitoneal injection (i.p.) twice a day for 2 days. At day 0, 1 hour after the treatment with compound 28, doxorubicin (25 mg/kg, i.p.) or another vehicle (10% DMSO in normal saline) were injected into mice.

Different tissues including livers, cardiac muscle (left ventricle), skeletal muscle (gastrocnemius), brown adipose tissue, and white adipose tissue were weighted and collected after mice were sacrificed. The tissues were fixed with 10% formalin at 4° C. overnight, processed in a tissue processor, and then embedded in paraffin. H&E of tissue sections (3-4 m) were carried out by a standard protocol as described above.

Unexpectedly, Compound 28 alleviated doxorubicin-induced hepatotoxicity and cachexia.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the compounds of this invention also can be made, screened for their efficacy in treating a condition that relates to Cisd2-insufficiency or protecting against doxorubicin-induced cardiotoxicity. Thus, other embodiments are also within the claims.

What is claimed is:
1. A compound of formula (I):

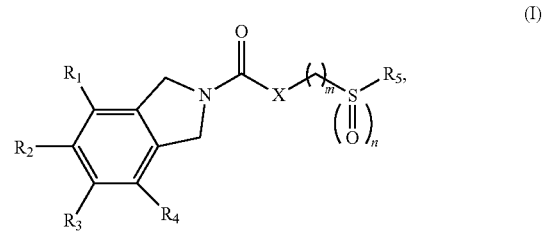

wherein
each of $R_1$, $R_2$, $R_3$, and $R_4$, independently, is H, halo, hydroxyl, $NO_2$, $C_1$-$C_6$ alkoxy, $CO_2R_a$, $C_{1-10}$ heterocycloalkyl, or $OC(O)R_a$, $R_a$ being $C_1$-$C_6$ alkyl optionally substituted with one or more groups selected from halo, cycloalkyl, cycloheteroalkyl, aryl, and heteroaryl;
$R_5$ is aryl, aralkyl, heteroaryl, or heteroaryl alkyl, each of which is optionally substituted with one or more groups selected from halo, $C_1$-$C_6$ alkyl, $NH_2$, CN, and oxo X is NH, $CH_2$, or $CF_2$;
m is 0, 1, or 2; and
n is 0, 1, or 2,
provided that, (i) when X is $CH_2$; m is 0; and n is 0; then $R_5$ is

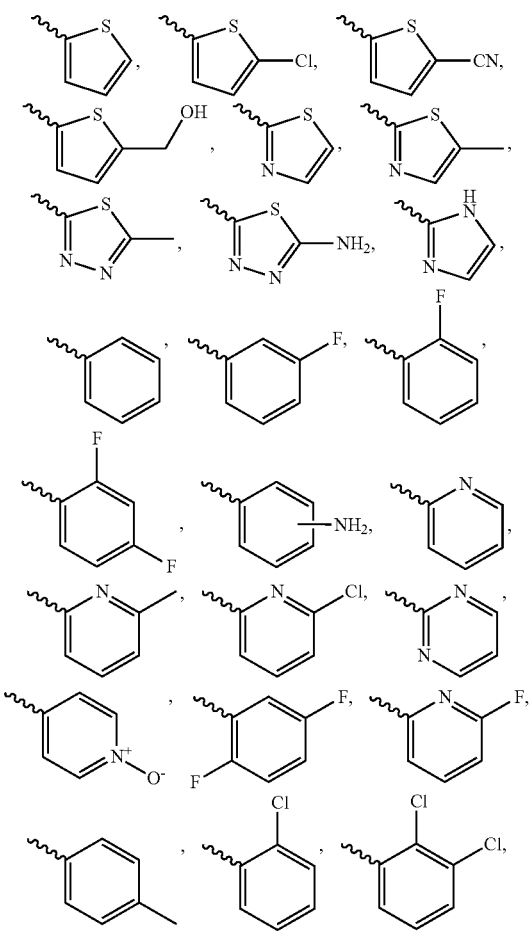

-continued

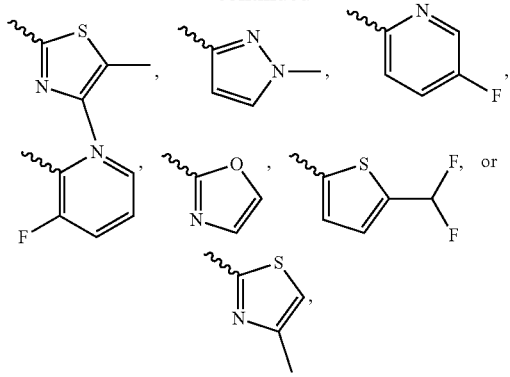

and
(ii) when X is NH, then $R_5$ is

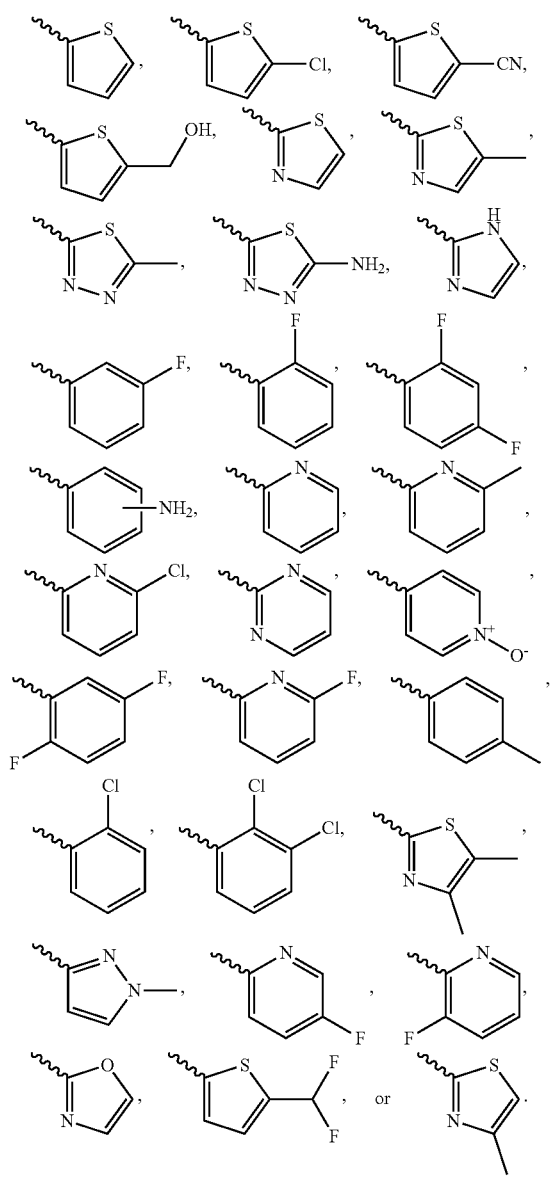

2. The compound of claim 1, wherein each of $R_1$, $R_2$, and $R_3$, independently, is H, F, Cl, OH, $NO_2$, $CH_3O$, morpholino, or $CO_2CH_3$, and $R_4$ is H.

3. The compound of claim 1, wherein $R_5$ is

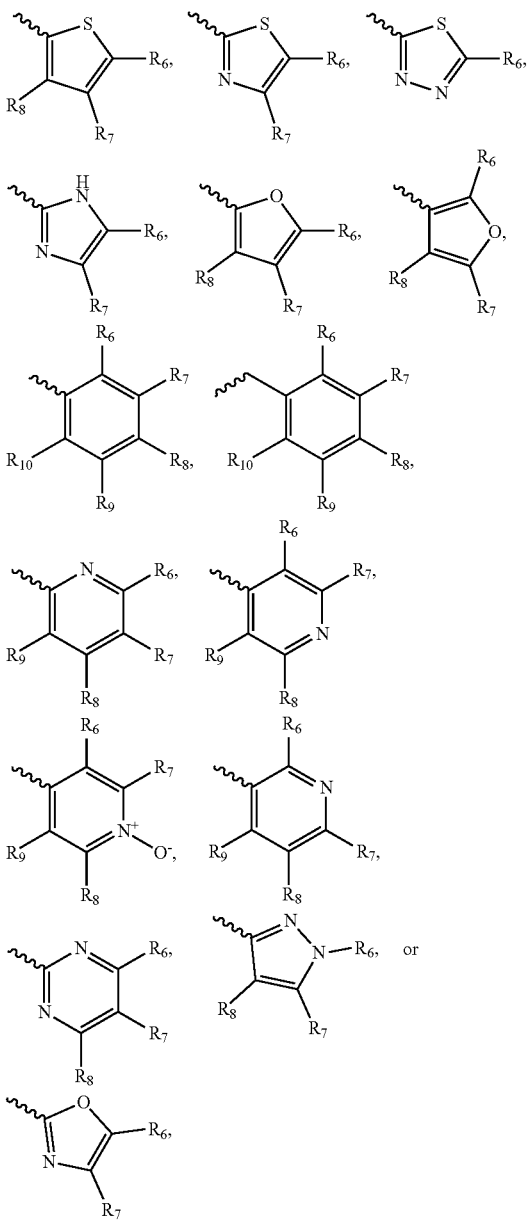

in which, each of $R_6$, $R_7$, $R_8$, $R_9$, and $R_{10}$, independently, is H, F, Cl, OH, CN, $NO_2$, $NH_2$, $NHC(O)R_{11}$, $C_1$-$C_6$ alkyl, difluoromethyl, $OR_{11}$, $CO_2CH_3$, $CO_2CH_2CH_3$, $CONHR_{11}$, $C(O)CH_3$, $C(O)CH_2CH_3$, or $CH_2OH$, Rn being $C_1$-$C_6$ alkyl or aryl.

4. The compound of claim 3, wherein $R_5$ is

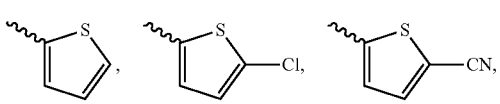

-continued

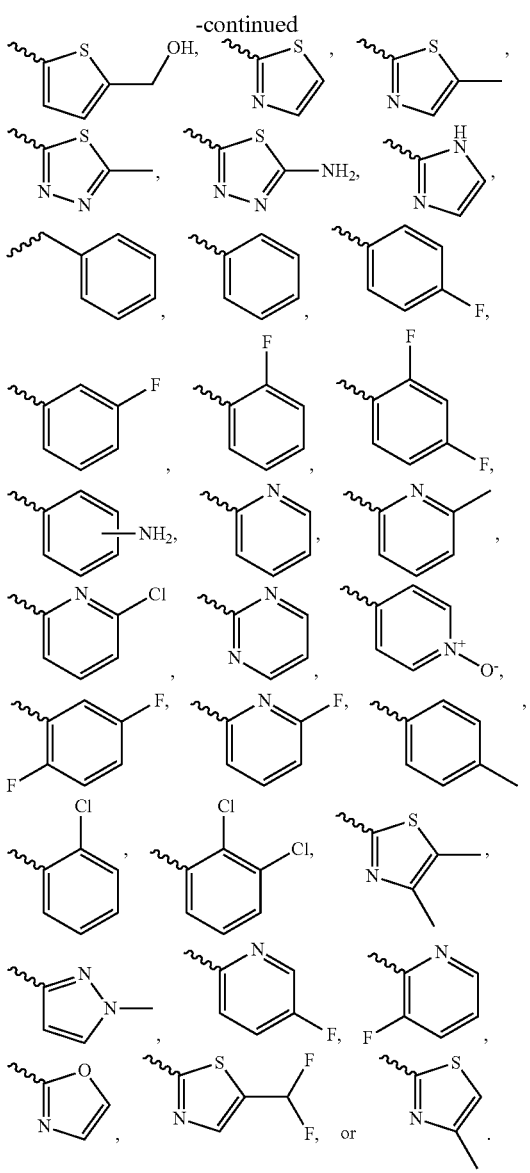

5. A compound of formula (I):

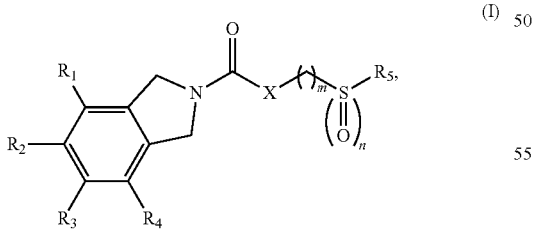

wherein each of $R_1$, $R_2$, $R_3$, and $R_4$, independently, is H, halo, hydroxyl, $NO_2$, $NH_2$, $C_1$-$C_6$ alkoxy, $CO_2R_a$, $C_{1-10}$ heterocycloalkyl, or $OC(O)R_a$, $R_a$ being $C_1$-$C_6$ alkyl optionally substituted with one or more groups selected from halo, cycloalkyl, cyclohetereoalkyl, aryl, and heteroaryl;

$R_5$ is aryl, aralkyl, heteroaryl, or heteroaryl alkyl, each of which is optionally substituted with one or more groups selected from halo, $C_1$-$C_6$ alkyl, $NH_2$, CN, and oxo;

X is $CH_2$ or $CF_2$;

m is 0 or 1; and n is 0, 1, or 2, provided that, when X is $CH_2$, m and n are not both 0.

6. The compound of claim 5, wherein X is $CH_2$, m is 0 or 1, and n is 1 or 2.

7. The compound of claim 1, wherein X is NH, in is 2, and n is 0.

8. The compound of claim 5, wherein X is $CF_2$, and in is 0 or 1.

9. The compound of claim 5, wherein each of $R_1$, $R_2$, and $R_3$, independently, is H, F, Cl, OH, $NO_2$, $NH_2$, $CH_3O$, morpholino, or $CO_2CH_3$, and $R_4$ is H.

10. The compound of claim 5, wherein $R_5$ is

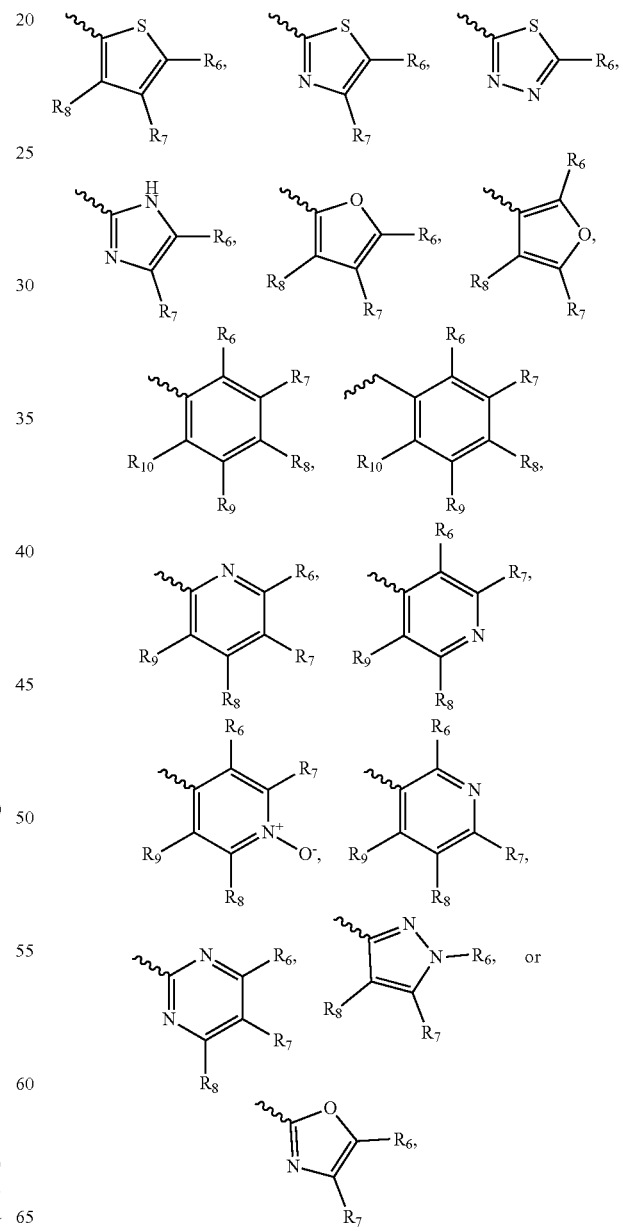

in which, each of $R_6$, $R_7$, $R_8$, $R_9$, and $R_{10}$, independently, is H, F, Cl, OH, CN, $NO_2$, $NH_2$, $NHC(O)R_{11}$, $C_1$-$C_6$ alkyl, difluoromethyl, $OR_{11}$, $CO_2CH_3$, $CO_2CH_2CH_3$, $CONHR_{11}$, $C(O)CH_3$, $C(O)CH_2CH_3$, or $CH_2OH$, $R_{11}$ being $C_1$-$C_6$ alkyl or aryl.

11. The compound of claim 10, wherein $R_5$ is

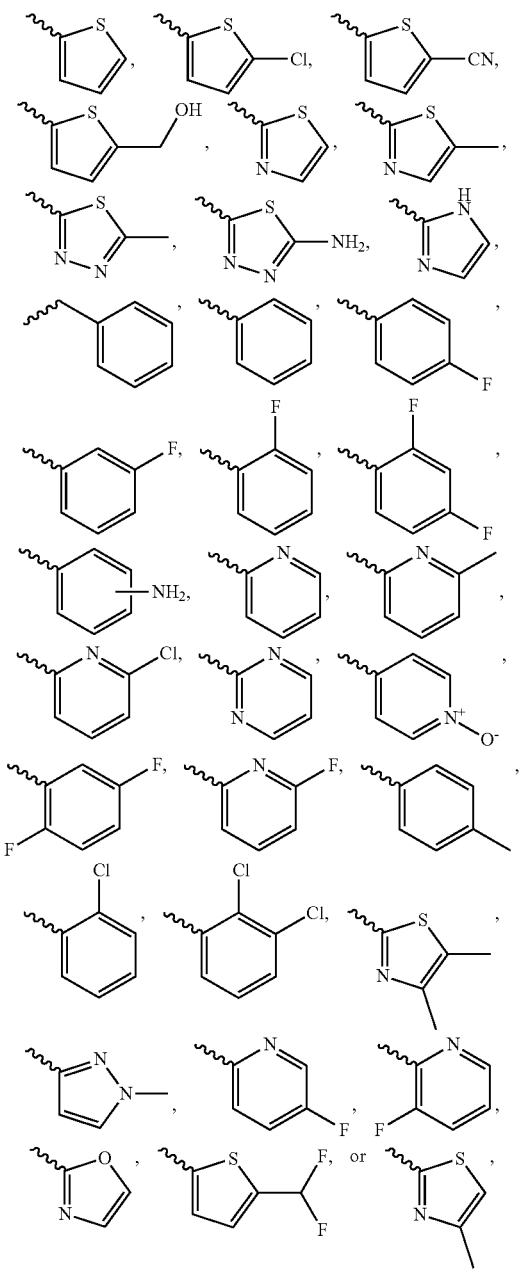

12. The Compound of claim 1, wherein each of $R_1$, $R_2$, and $R_3$, independently, is H or F, and $R_4$ is H.

13. The compound of claim 12, wherein $R_5$ is

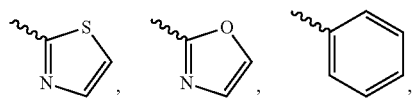

-continued

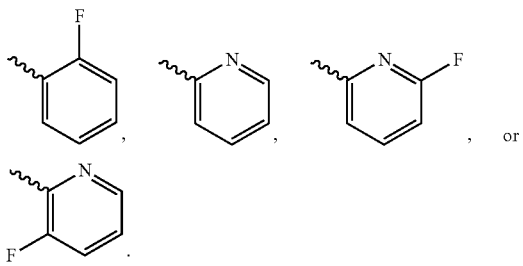

14. The compound of claim 12, wherein X is $CH_2$.
15. The compound of claim 12, wherein m is 0 or 1.
16. The compound of claim 12, wherein n is 1 or 2.
17. A compound selected from the group consisting of Compounds 1-109 having the following structures:

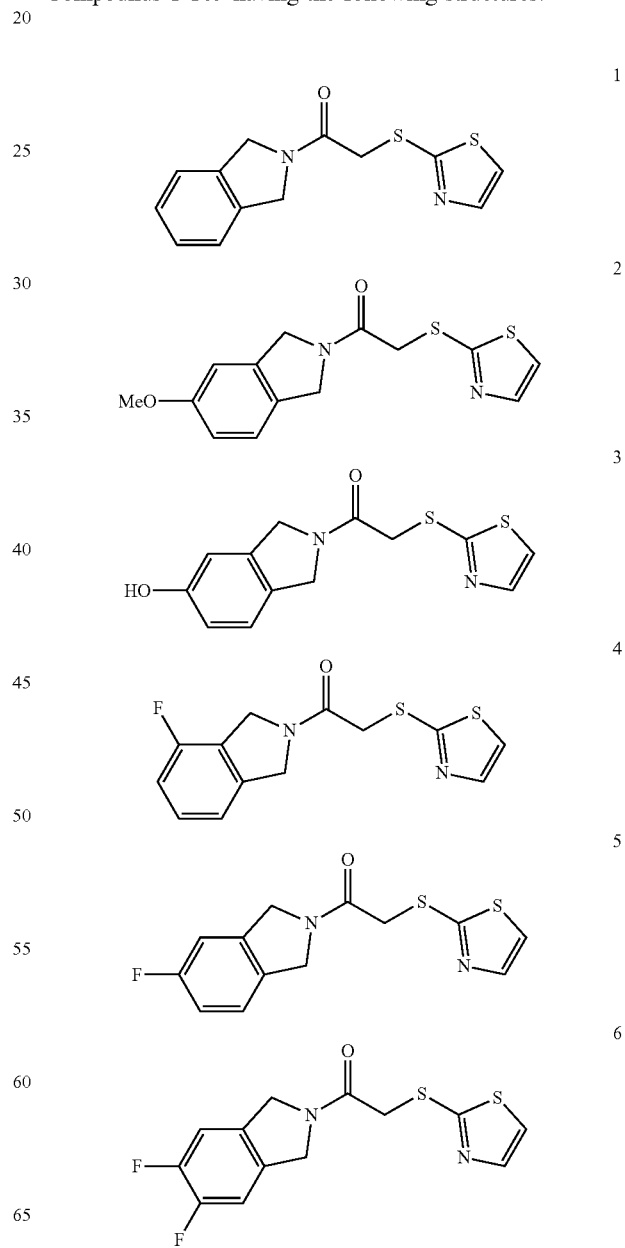

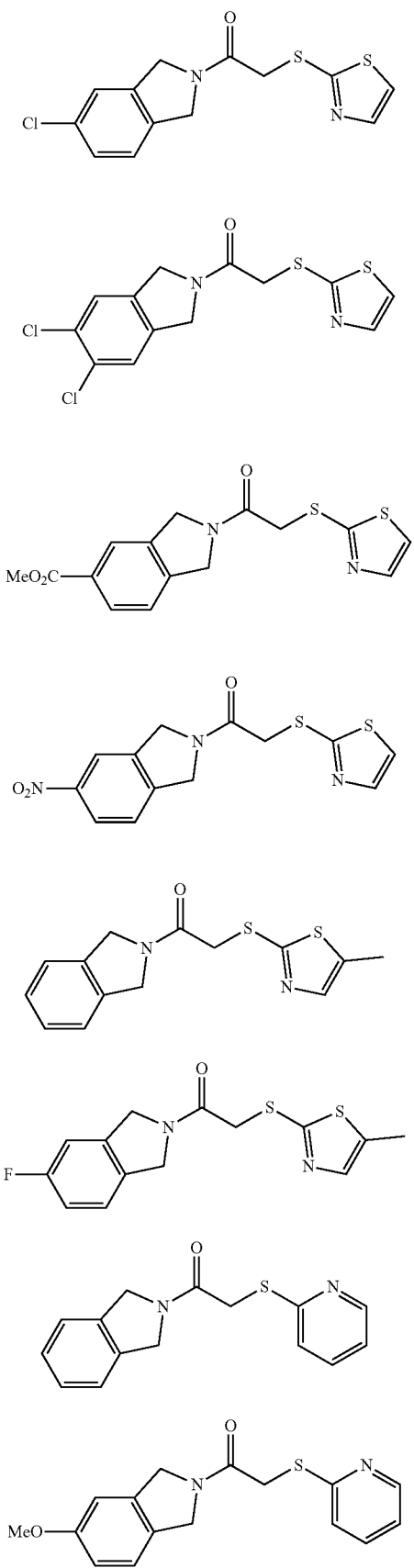
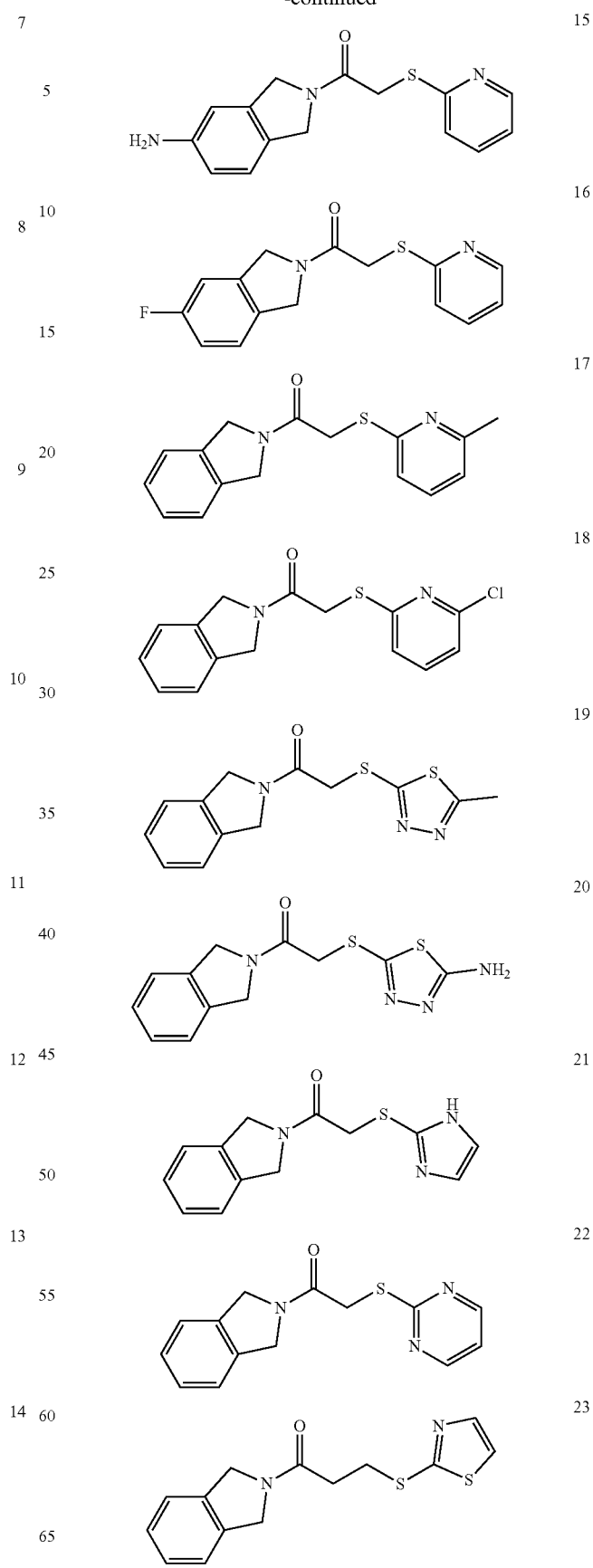

-continued

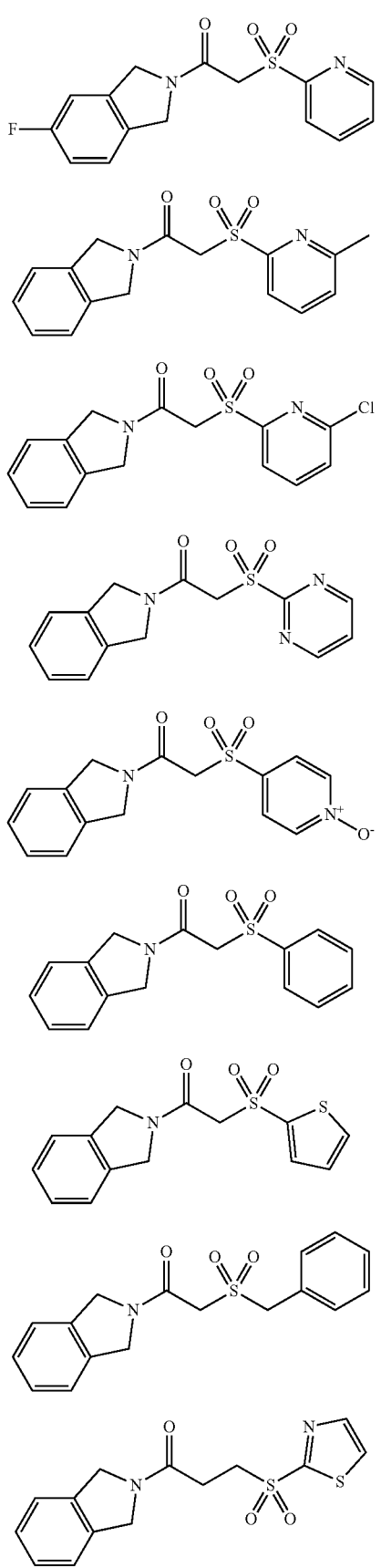
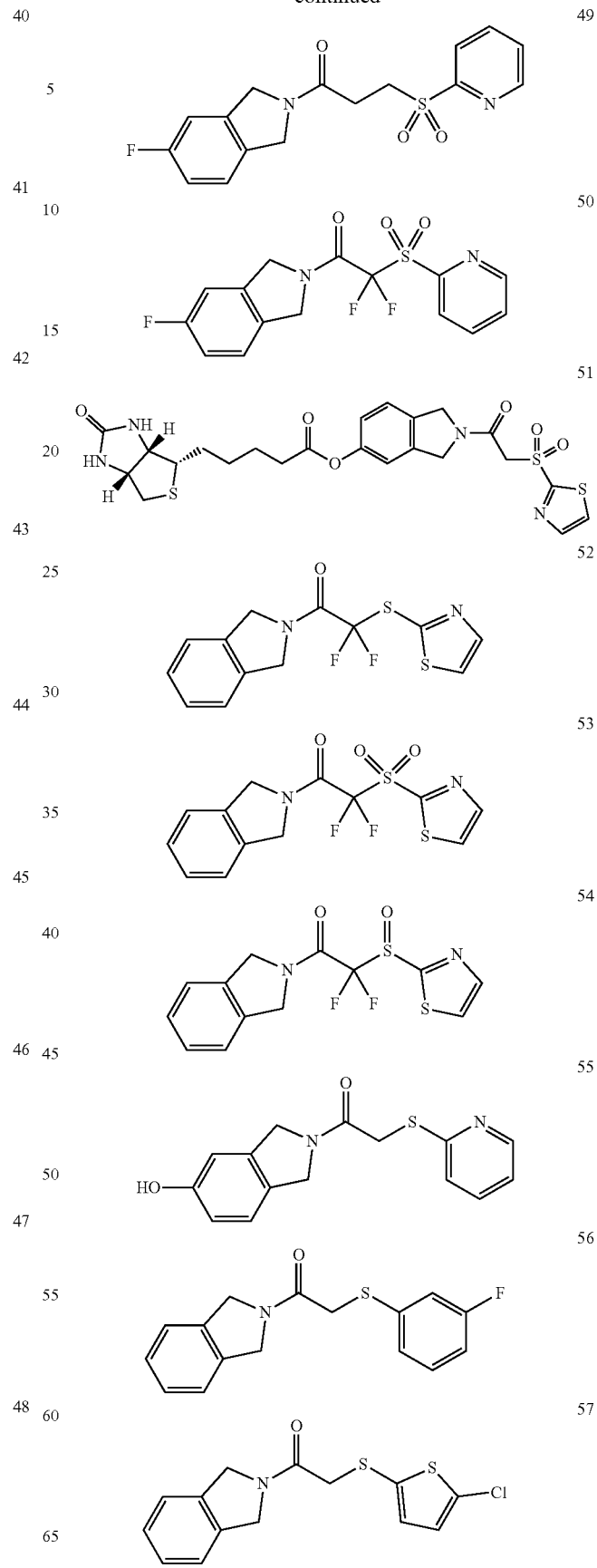

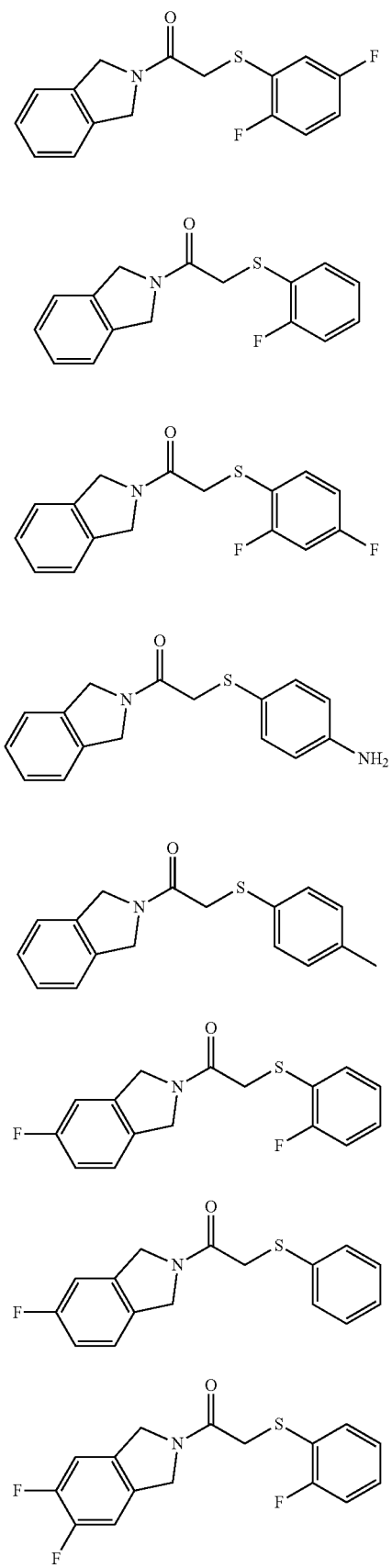
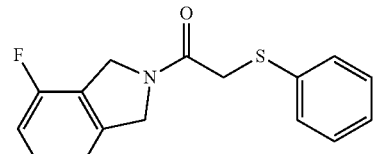
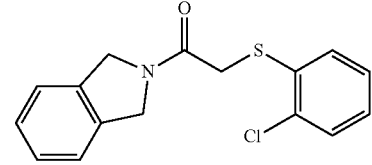
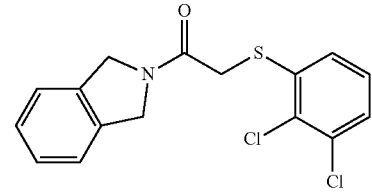
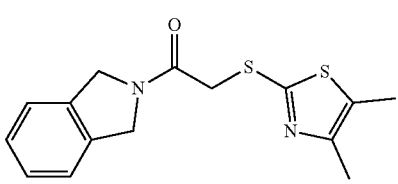
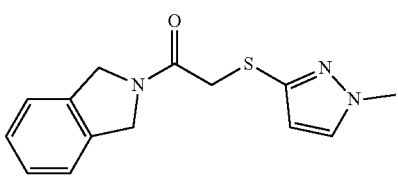
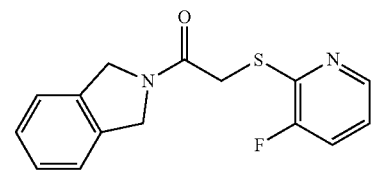
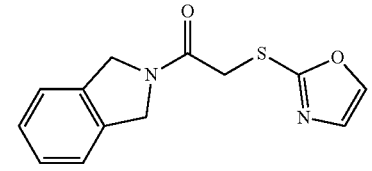
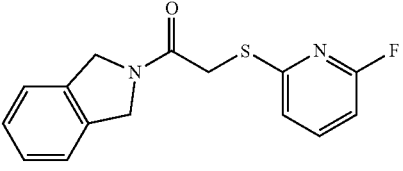
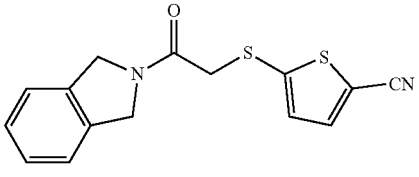

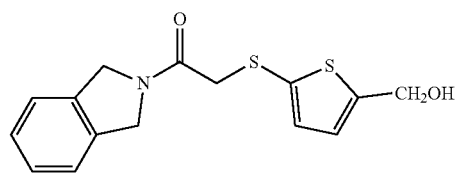 75
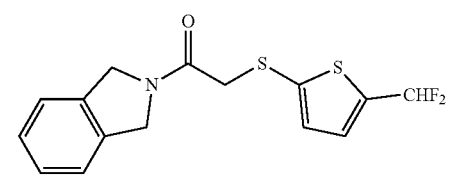 76
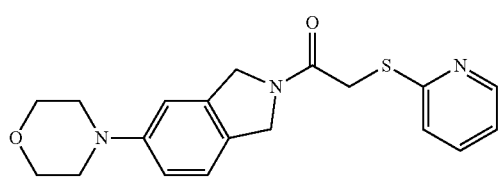 77
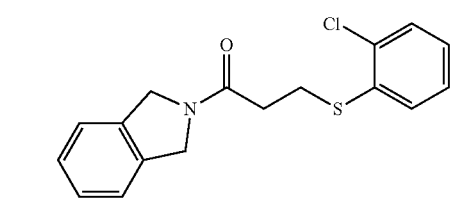 78
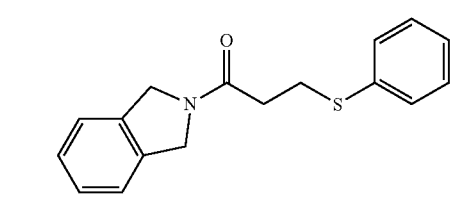 79
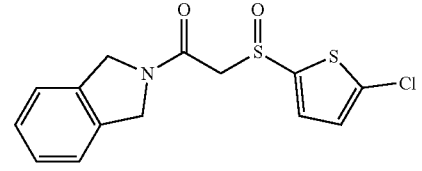 80
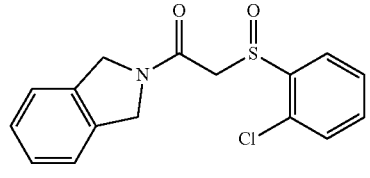 81
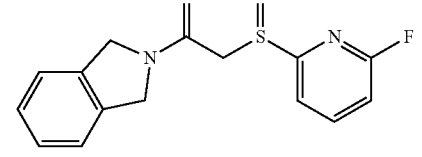 82
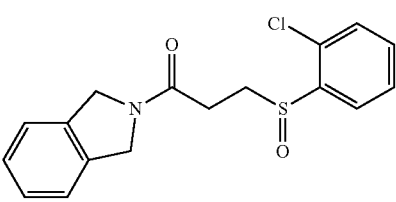 83
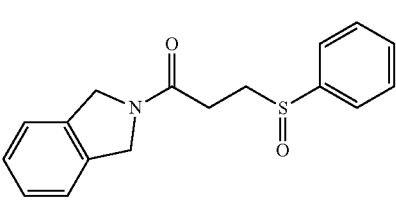 84
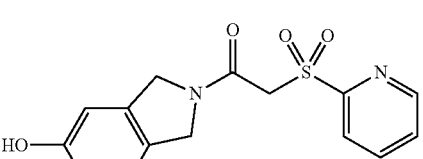 85
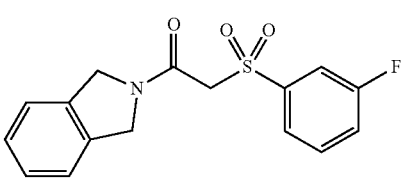 86
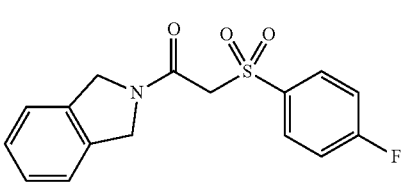 87
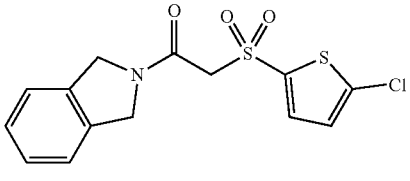 88
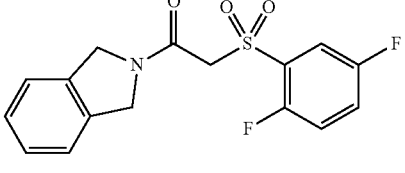 89
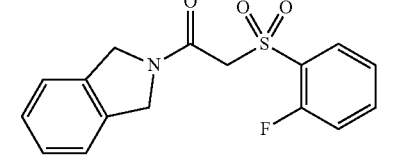 90

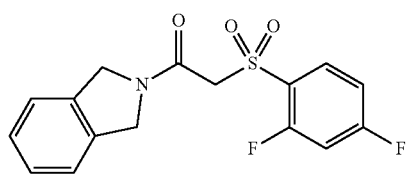
91
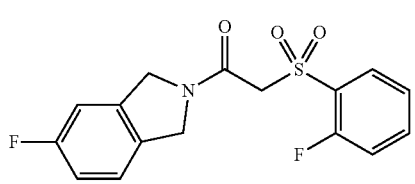
92
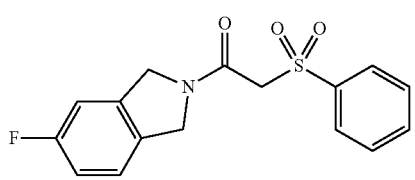
93
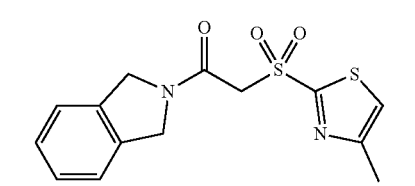
94
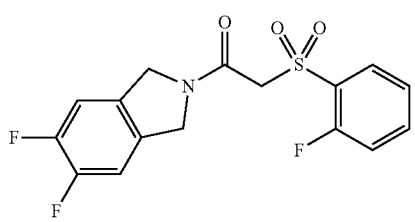
95
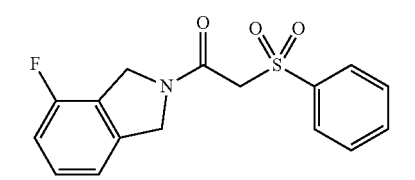
96
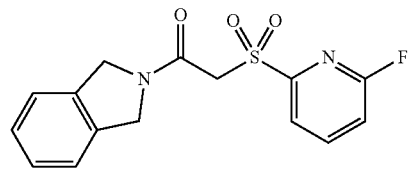
97
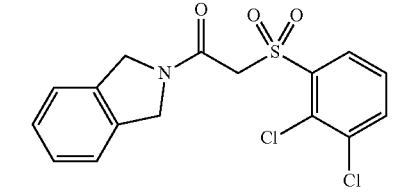
98
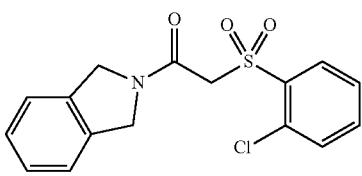
99
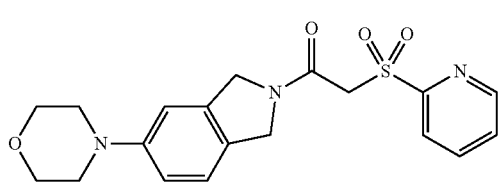
100
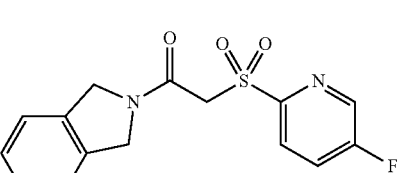
101
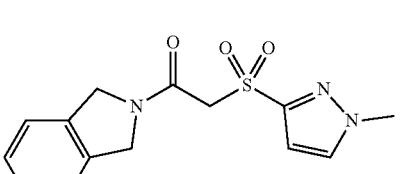
102
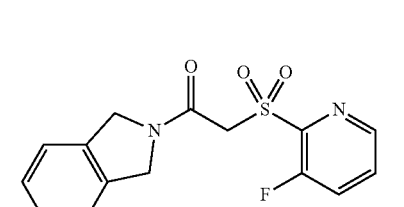
103
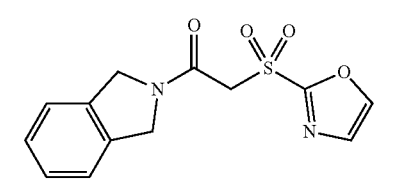
104
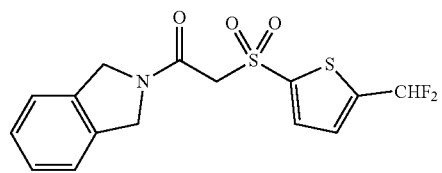
105
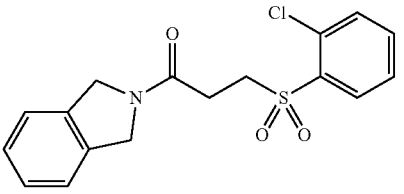
106

-continued

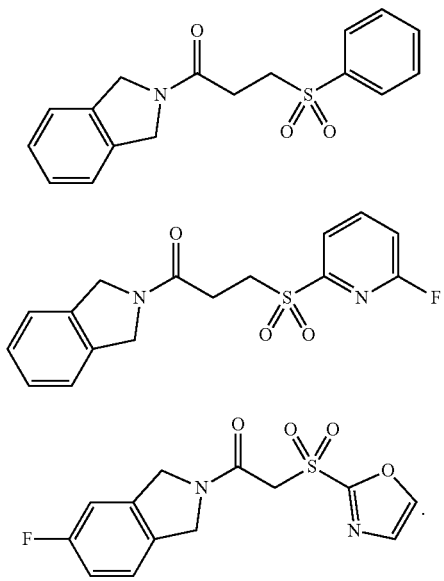

18. The compound of claim 17, wherein the compound is one of Compounds 28-48, 51, 82, 85-105, and 109.

19. A pharmaceutical composition comprising a compound of claim 1 and a pharmaceutically acceptable carrier thereof.

20. A method of treating a Cisd2-insufficiency associated disorder, the method comprising:
   identify a subject suffering from a Cisd2-insufficiency associated disorder, and
   administering to the subject an effective amount of a compound of claim 1.

21. The method of claim 20, wherein the Cisd2-insufficiency associated disorder is nonalcoholic fatty liver disease or nonalcoholic steatohepatitis.

22. A method of protecting a subject against doxorubicin-induced cardiotoxicity comprising administering to the subject an effective amount of a compound of claim 1.

* * * * *

UNITED STATES PATENT AND TRADEMARK OFFICE
CERTIFICATE OF CORRECTION

| | |
|---|---|
| PATENT NO. | : 11,827,629 B2 |
| APPLICATION NO. | : 17/824547 |
| DATED | : November 28, 2023 |
| INVENTOR(S) | : Ting-Fen Tsai et al. |

It is certified that error appears in the above-identified patent and that said Letters Patent is hereby corrected as shown below:

In the Claims

Claim 7, Column 84, Line 10, "in" should read --m--.

Claim 8, Column 84, Line 12, "in" should read --m--.

Signed and Sealed this
Nineteenth Day of March, 2024

Katherine Kelly Vidal
*Director of the United States Patent and Trademark Office*